(12) United States Patent
Ren et al.

(10) Patent No.: US 10,069,082 B2
(45) Date of Patent: Sep. 4, 2018

(54) ORGANIC ELECTROLUMINESCENT COMPOUNDS AND ORGANIC OPTOELECTRONIC DEVICES COMPRISING THE SAME

(71) Applicants: SHANGHAI TIANMA AM-OLED CO., LTD., Shanghai (CN); TIANMA MICRO-ELECTRONICS CO., LTD., Shenzhen (CN)

(72) Inventors: Hongyang Ren, Shanghai (CN); Xiangcheng Wang, Shanghai (CN); Wei He, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 15/198,177

(22) Filed: Jun. 30, 2016

(65) Prior Publication Data
US 2017/0148996 A1    May 25, 2017

(30) Foreign Application Priority Data
Nov. 20, 2015    (CN) .......................... 2015 1 0810708

(51) Int. Cl.
| | | |
|---|---|---|
| H01L 51/00 | (2006.01) |
| C09K 11/02 | (2006.01) |
| C07D 471/04 | (2006.01) |
| C07D 417/14 | (2006.01) |
| C07D 498/04 | (2006.01) |

(Continued)

(52) U.S. Cl.
CPC ........ *H01L 51/0071* (2013.01); *C07D 413/14* (2013.01); *C07D 417/14* (2013.01); *C07D 471/04* (2013.01); *C07D 498/04* (2013.01); *C09K 11/025* (2013.01); *C09K 11/06* (2013.01); *H01L 51/0052* (2013.01); *H01L 51/0061* (2013.01); *H01L 51/0072* (2013.01); *H05B 33/20* (2013.01); *C09K 2211/1007* (2013.01); *C09K 2211/1011* (2013.01); *C09K 2211/1014* (2013.01); *C09K 2211/1033* (2013.01); *C09K 2211/1037* (2013.01);
(Continued)

(58) Field of Classification Search
None
See application file for complete search history.

(56) References Cited

U.S. PATENT DOCUMENTS

| | | | | |
|---|---|---|---|---|
| 2011/0272676 A1* | 11/2011 | Jung | .................... | C07D 235/18 257/40 |
| 2015/0239880 A1* | 8/2015 | Adachi | ................ | C07D 403/10 544/104 |

FOREIGN PATENT DOCUMENTS

| | | | |
|---|---|---|---|
| CN | 10465066 A | | 5/2015 |
| CN | 105481845 A | * | 4/2016 |

(Continued)

OTHER PUBLICATIONS

Machine English translation of Ren et al. (CN 105481845 A). Dec. 19, 2017.*

(Continued)

*Primary Examiner* — Jay Yang
(74) *Attorney, Agent, or Firm* — Kilpatrick Townsend & Stockton LLP

(57) ABSTRACT

The present application provides an organic electroluminescent compound, use thereof in organic optoelectronic device, and an organic photoelectric device comprising the same.

20 Claims, 2 Drawing Sheets

(51) Int. Cl.
*C09K 11/06* (2006.01)
*C07D 413/14* (2006.01)
*H05B 33/20* (2006.01)
*H01L 51/50* (2006.01)

(52) U.S. Cl.
CPC .. *C09K 2211/1044* (2013.01); *H01L 51/5012* (2013.01); *H01L 51/5016* (2013.01)

(56) References Cited

FOREIGN PATENT DOCUMENTS

| TW | 201416411 A | 5/2014 |
| WO | 2012149999 A1 | 11/2012 |
| WO | 2014034535 A1 | 3/2014 |
| WO | WO-2014/034535 A1 * | 3/2014 |
| WO | 2015022835 A1 | 2/2015 |
| WO | 2015175678 A1 | 11/2015 |

OTHER PUBLICATIONS

Ren, Hongyang et al., "Synthesis and solvatochromism of an intramolecular charge transfer phenoxazine derivative", New Chemical Materials, issued in Jul. 2015, 4 pages.

* cited by examiner

ORGANIC ELECTROLUMINESCENT COMPOUNDS AND ORGANIC OPTOELECTRONIC DEVICES COMPRISING THE SAME

CROSS REFERENCE TO RELATED APPLICATIONS

This application claims the benefit of Chinese patent application No. 201510810708.8, filed on Nov. 20, 2015, of which the disclosure is incorporated by reference in its entirety.

TECHNICAL FIELD

The present application relates to the field of organic electroluminescent material, and particularly to an organic electroluminescent material, and application of the material in organic photoelectric device.

BACKGROUND

In recent years, organic light emitting diode (OLED) becomes a very popular new generation display products domestically and abroad due to its advantages of self-illumination, high efficiency, wide color gamut, wide viewing angle, etc. Meanwhile, organic materials for preparing OLED play a crucial role.

Wherein, the material for OLED luminescent layer produces singlet excited state ($S_1$) excitons and triplet excited state ($T_1$) excitons upon electroexcitation, and the numerical ratio of the two excitons is 1:3 according to spin statistics. Depending on different luminescent mechanisms, the materials which can be used in the luminescent layer of organic light emitting diode generally are the following kinds. Fluorescent materials, only utilizing 25% of the singlet state $S_1$ excitons, go back to the ground state $S_0$ by radiative transition, thus the largest external quantum efficiency of OLED applying such materials can not break this limit. The second kind is phosphorescent materials, utilizing not only 25% of the singlet state $S_1$ excitons but also 75% of the triplet state $T_1$ excitons, thus the theoretical internal quantum efficiency can reach 100%, and the luminescent effect when applying to OLED is absolutely better than fluorescent materials. However, since most phosphorescent materials are rare metal complexes, the cost of the materials is higher, and the blue phosphorescent materials always have some problems, such as poor efficiency and lifetime, when being applied in OLED. In 2011, professor Adachi, et al., at Kyushu University in Japan reported that a thermally activated delayed fluorescence (TADF) materials have good luminescence performance. The energy gap between $S_1$ state and $T_1$ state of this material is small, and the lifetime of the $T_1$ state excitons is longer. $T_1$ state excitons can achieve the $T_1 \rightarrow S_1$ process by reverse intersystem crossing (RISC) and then the radiation attenuation from the $S_1$ state to the ground state $S_0$ under a certain temperature. Therefore, the luminescence efficiency of OLED devices using such materials as a luminescent layer can be comparable to that of phosphorescent materials, and rare metal elements are not required and the material cost is low. However, such materials are still rare currently, and there is an urgent need for developing novel high-performance TADF materials.

SUMMARY

The present application aims at providing a novel organic electroluminescent compound having thermally activated delayed fluorescence (TADF) property.

According to one embodiment of the present application, a compound having the structure of Formula (I) is provided

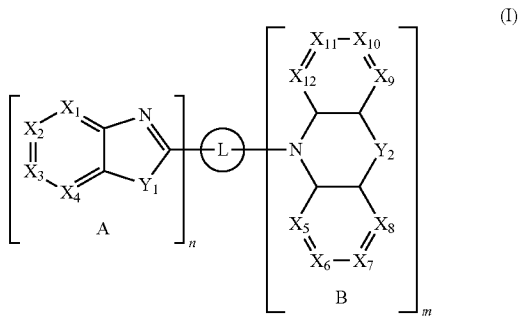

wherein $X_1$ to $X_{12}$ are each independently $CR_1$ or N;

Y1 is O, S or $NR_2$;

$Y_2$ is a single bond, O, S, $CR_3R_4$, $NR_5$ or $SiR_6R_7$;

$R_1$ to $R_7$ are each independently hydrogen, deuterium, $C_{1-30}$ alkyl, $C_{6-30}$ aryl or $C_{2-20}$ heteroaryl;

L is a linking moiety which enables the structure of the Formula (I) to form a conjugated system;

n and m are each independently 1, 2 or 3;

if n is greater than 1, each Moiety A in the Formula (I) is the same as each other or different from each other; and if m is greater than 1, each Moiety B in the Formula (I) is the same as each other or different from each other. According to one embodiment of the present application, use of the above-mentioned compounds in an organic optoelectronic device is provided.

According to one embodiment of the present application, an organic optoelectronic device is provided, the device comprises an anode, a cathode and one or more organic layers located between the anode and cathode, and the organic layers comprise the above-mentioned compound.

DETAILED DESCRIPTION

Figure 1:
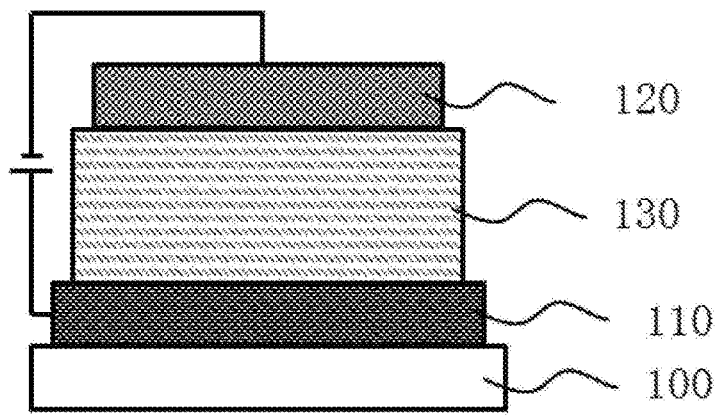
FIG. 1 illustrates an exemplary structure of an organic electroluminescent diode according to a first embodiment of the present invention.

In one embodiment, a compound having the structure of Formula (I) is provided:

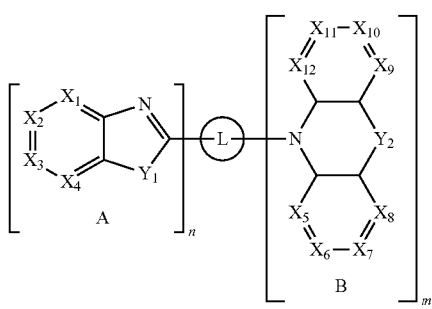

(I)

wherein
X$_1$ to X$_{12}$ are each independently CR$_1$ or N;
Y1 is O, S or NR$_2$;
Y$_2$ is a single bond, O, S, CR$_3$R$_4$, NR$_5$ or SiR$_6$R$_7$;
R$_1$ to R$_7$ are each independently hydrogen, deuterium, C$_{1-30}$ alkyl, C$_{6-30}$ aryl or C$_{2-20}$ heteroaryl;
L is a linking moiety which enables the structure of Formula (I) to form a conjugated system;
n and m are each independently 1, 2 or 3;
if n is greater than 1, each Moiety A in Formula (I) is the same as each other or different from each other; and
if m is greater than 1, each Moiety B in Formula (I) is the same as each other or different from each other.

In the above embodiment, the C$_{1-30}$ alkyl is a C$_{1-20}$ alkyl.
In the above embodiment, the C$_{1-30}$ alkyl is a C$_{1-10}$ alkyl.
In the above embodiment, the C$_{1-30}$ alkyl is a C$_{1-6}$ alkyl.
In the above embodiment, R$_1$ and R$_7$ are each independently hydrogen, deuterium, C$_{1-6}$ alkyl.
In one embodiment, wherein L in the structure of Formula (I) is C$_{6-30}$ aryl or C$_{2-30}$ heteroaryl.
In one embodiment, wherein L in the structure of Formula (I) is C$_{6-16}$ aryl.
In one embodiment, wherein L in the structure of Formula (I) is C$_{6-14}$ aryl.
In one embodiment, wherein L in the structure of Formula (I) is C$_{6-12}$ aryl.
In one embodiment, wherein L in the structure of Formula (I) is selected from the following structures:

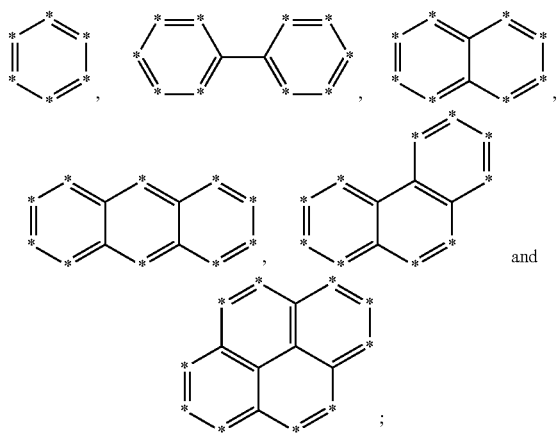

wherein, * represents CR$_8$, N or a site linked to the Moiety A or Moiety B, the R$_8$ is each independently hydrogen, deuterium, C$_{1-6}$ alkyl, C$_{1-16}$ aryl or C$_{2-6}$ heteroaryl. In the above embodiments, the substitution positions of the Moiety A and Moiety B on L are spaced by at least one atom.

In the above embodiment, the Moiety A is selected from the following groups:

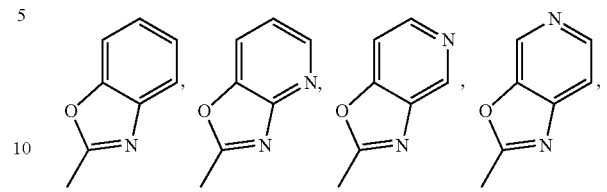

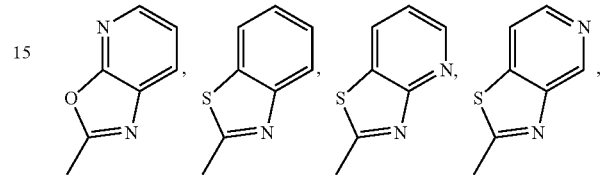

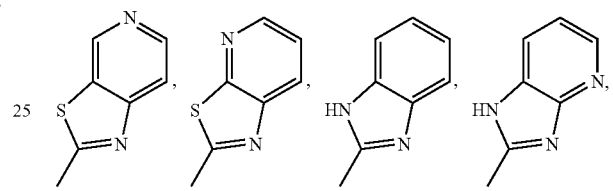

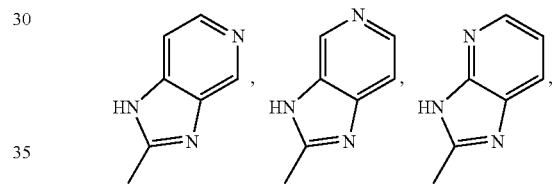

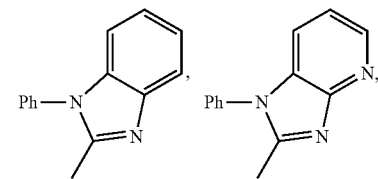

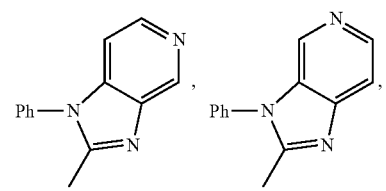

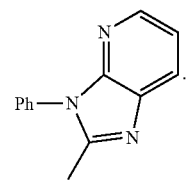

In the above embodiment, Moiety B is selected from the following groups:

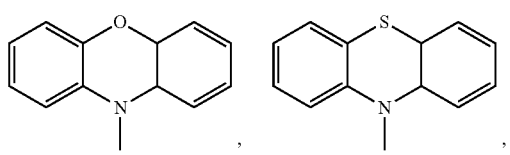

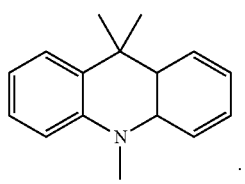

In the above embodiment, the energy gap $\Delta E_{st}$ between the lowest singlet state and the lowest triplet state of the compound is less than or equal to 0.30 eV.

In the above embodiment, the energy gap $\Delta E_{st}$ between the lowest singlet state and the lowest triplet state of the compound is less than or equal to 0.25 eV.

In the above embodiment, the energy gap $\Delta E_{st}$ between the lowest singlet state and the lowest triplet state of the compound is less than or equal to 0.15 eV.

In the above embodiment, the energy gap $\Delta E_{st}$ between the lowest singlet state and the lowest triplet state of the compound is less than or equal to 0.1 eV.

In the above embodiment, the energy gap $\Delta E_{st}$ between the lowest singlet state and the lowest triplet state of the compound is less than or equal to 0.05 eV.

In the above embodiment, the energy gap $\Delta E_{st}$ between the lowest singlet state and the lowest triplet state of the compound is less than or equal to 0.02 eV.

In the above embodiment, the energy gap $\Delta E_{st}$ between the lowest singlet state and the lowest triplet state of the compound is less than or equal to 0.01 eV.

The present application provides the following compounds, and the structure and number of the compounds are shown in the table below.

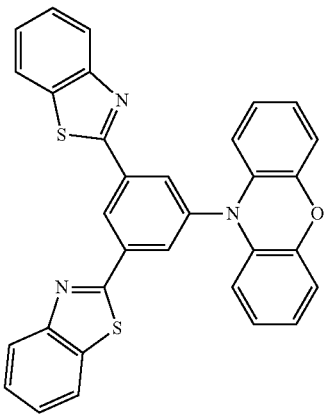

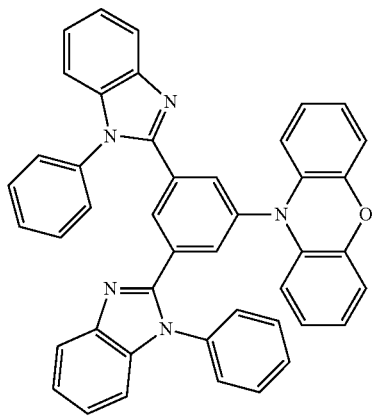

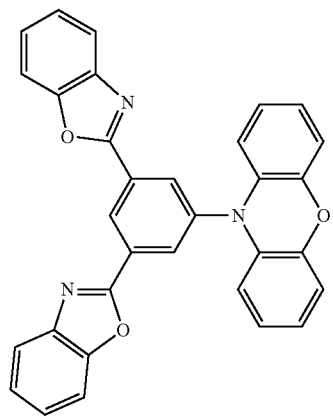

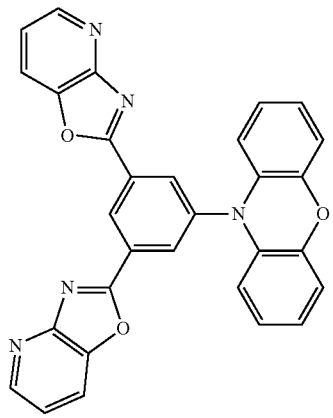

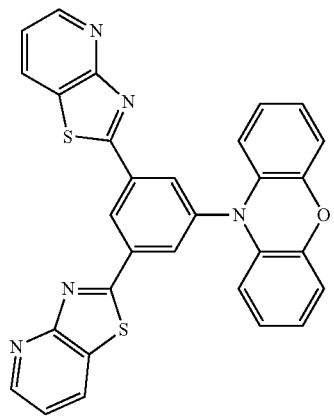
5
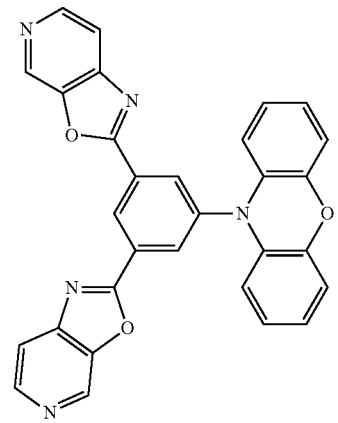
8
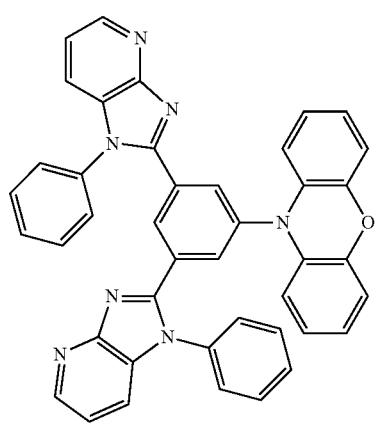
6
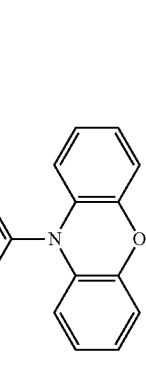
9
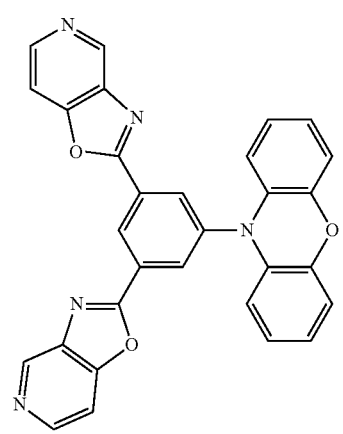
7
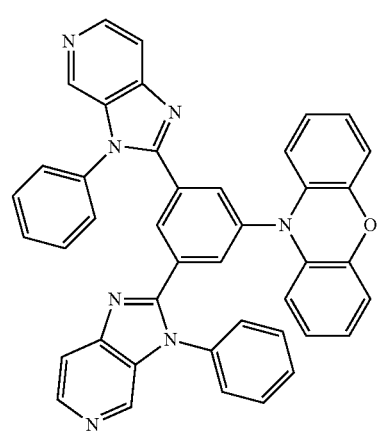
10

11
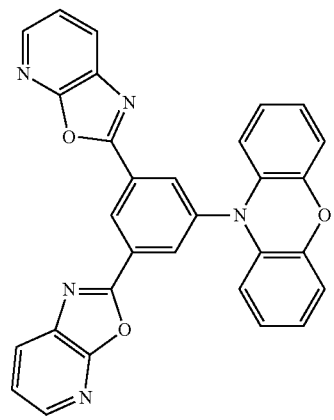
12
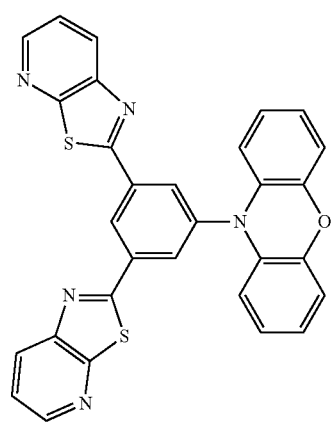
13
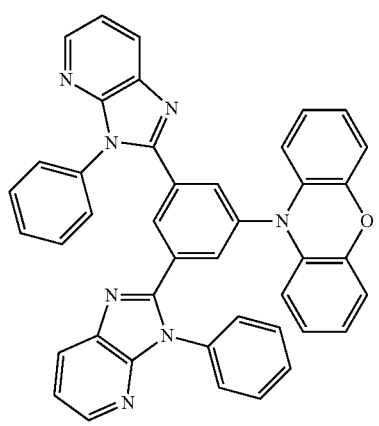
14
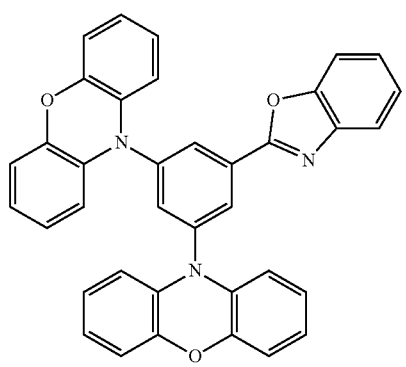
15
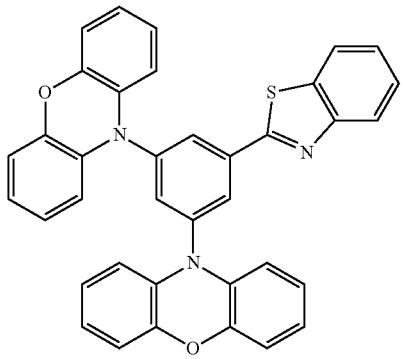
16
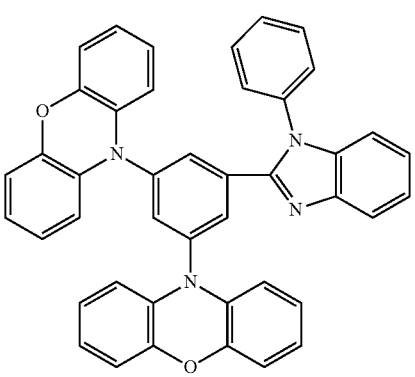
17
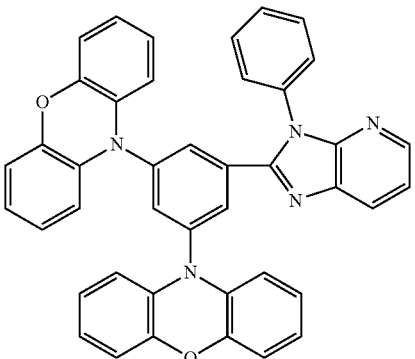
18
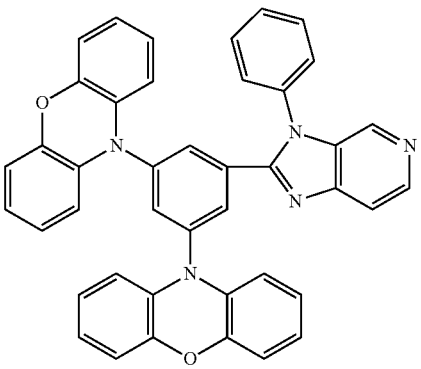

19
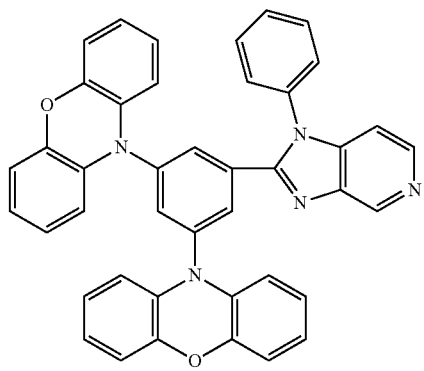
20
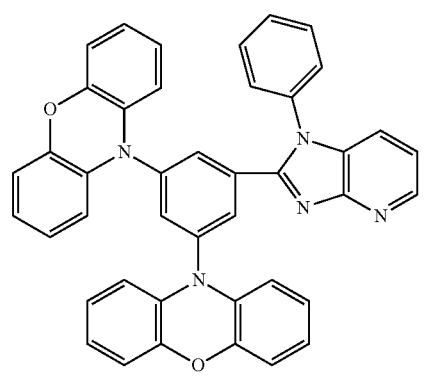
21
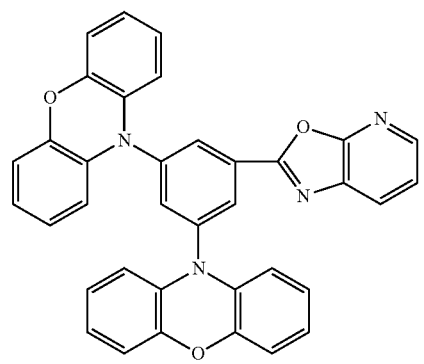
22
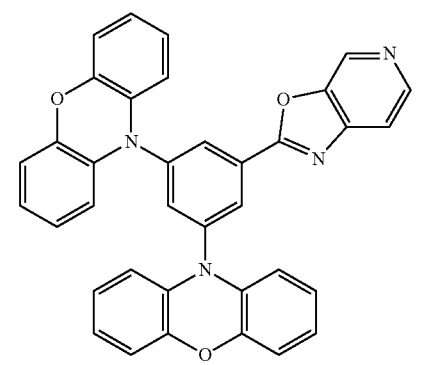
23
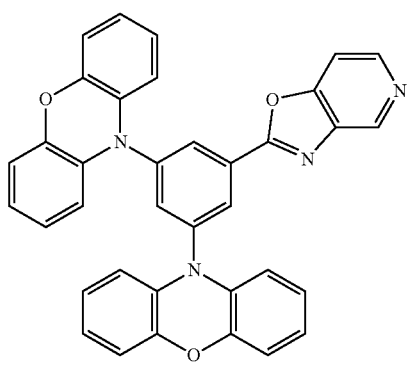
24
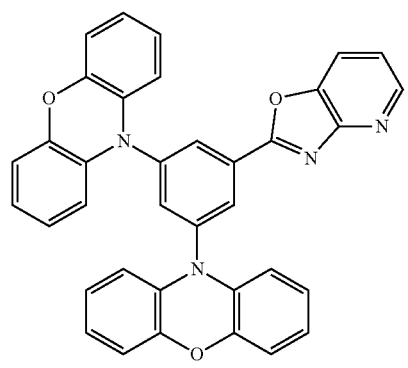
25
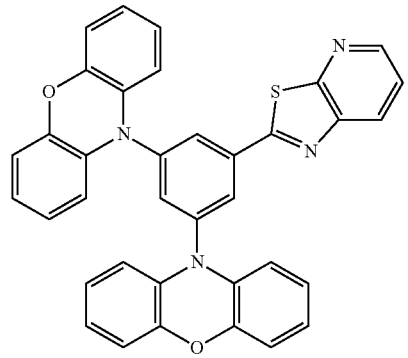
26
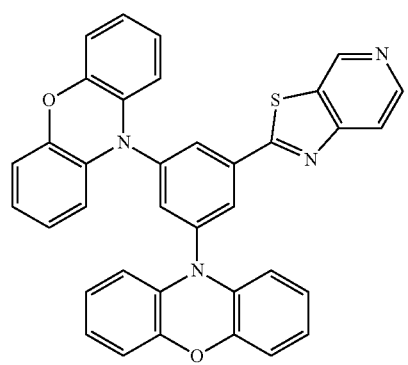

27
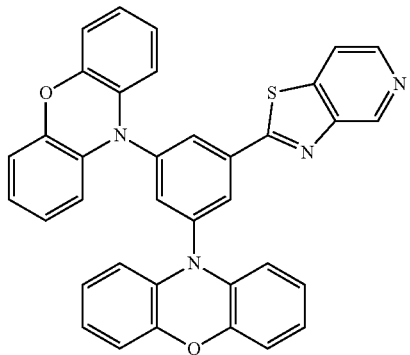
28
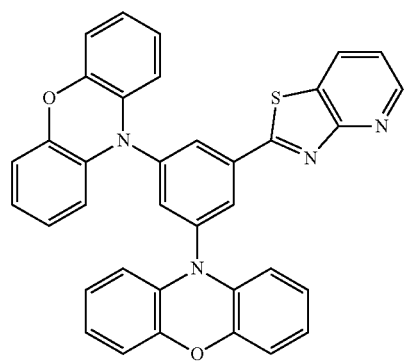
29
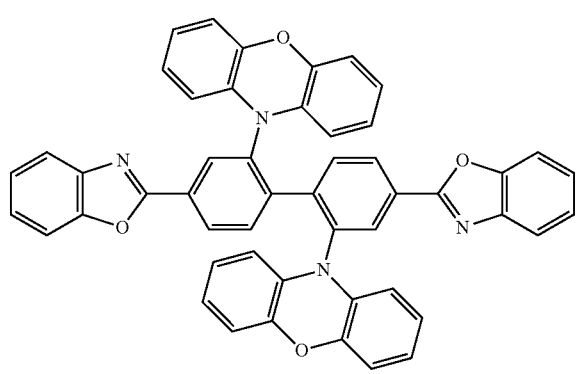
30
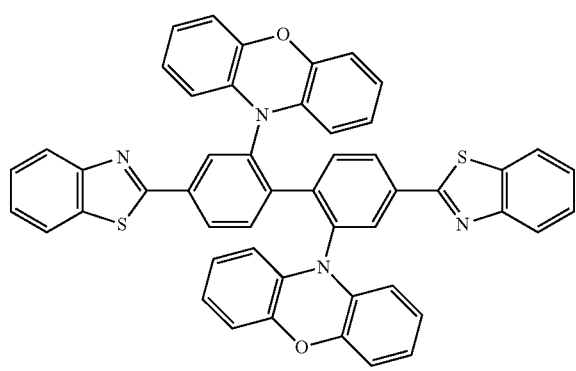
31
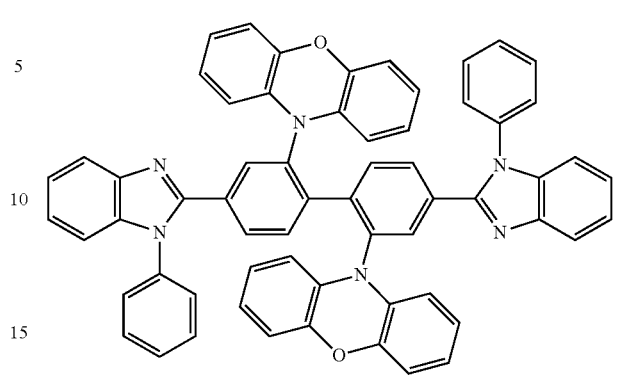
32
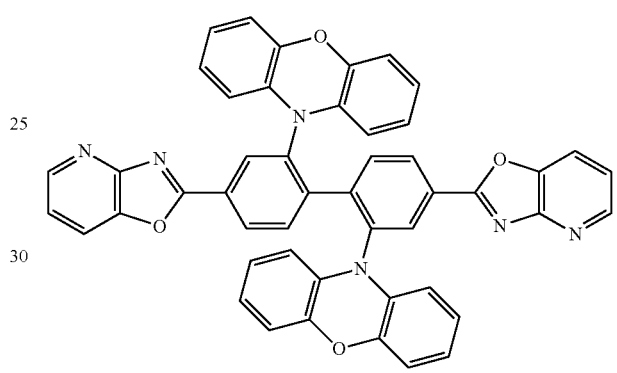
33
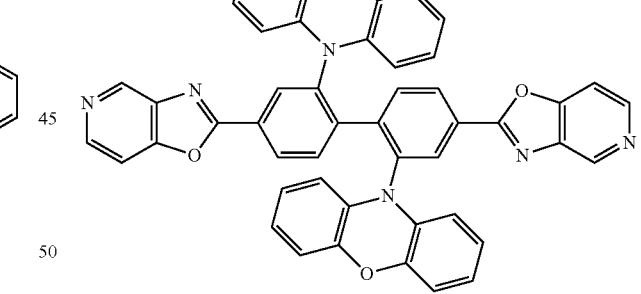
34
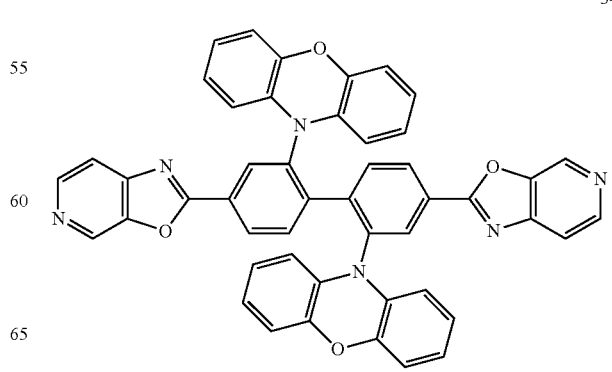

35
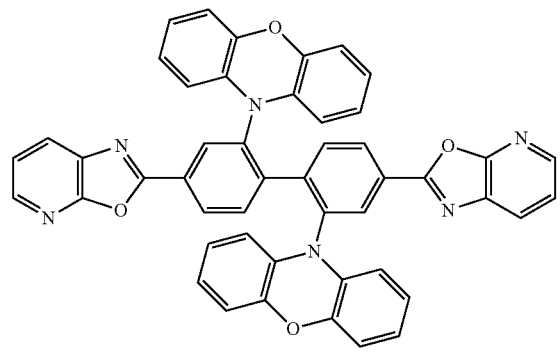
36
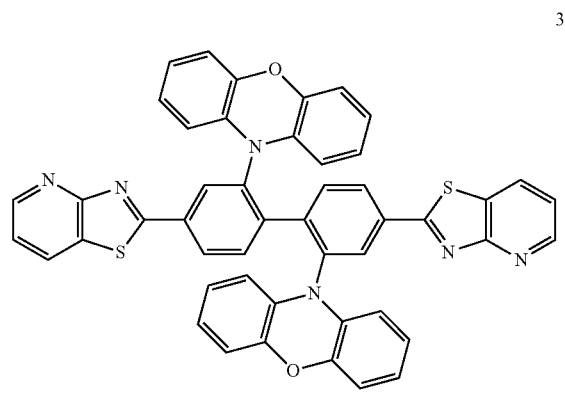
37
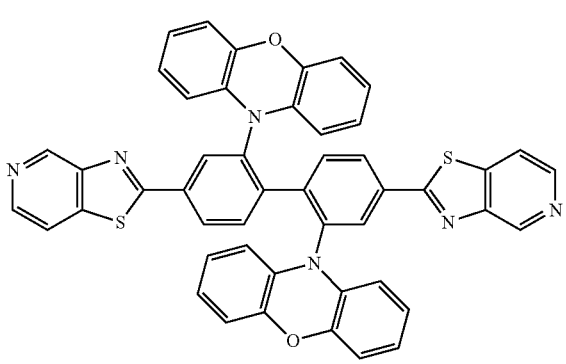
38
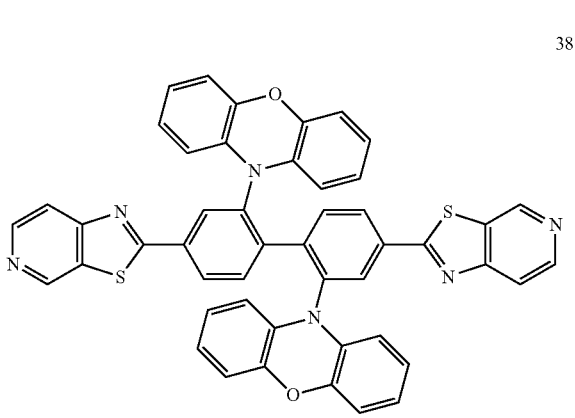
39
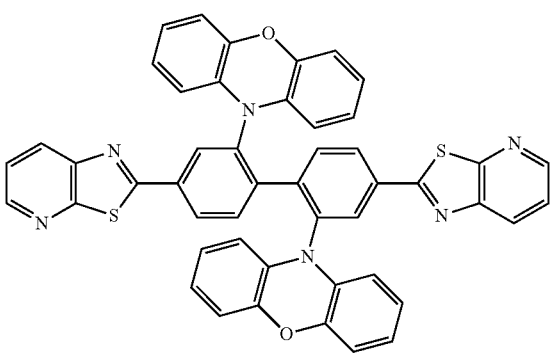
40
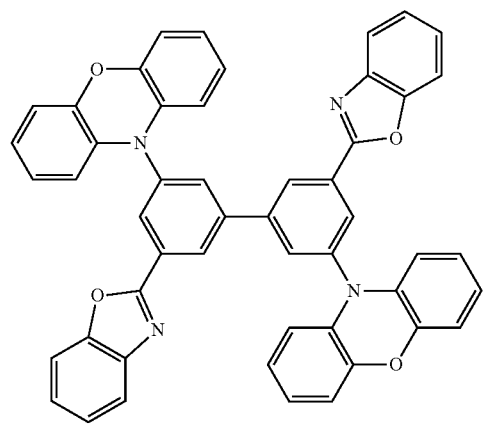
41
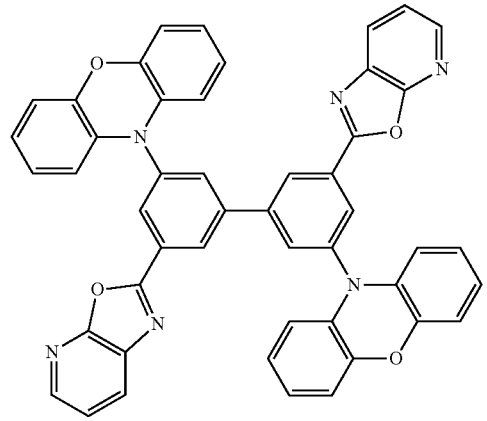

42
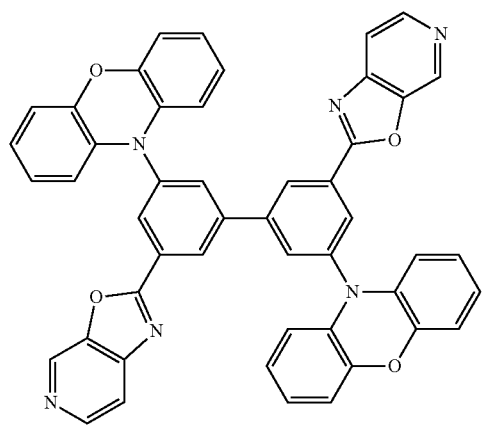
43
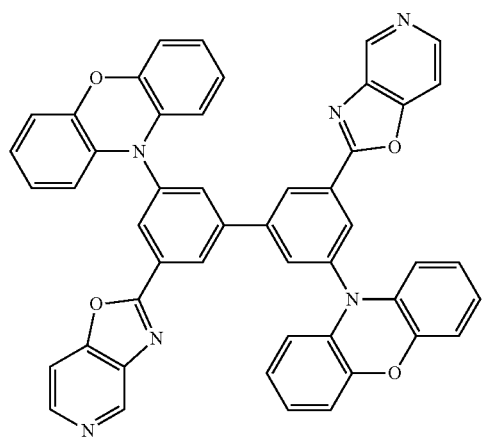
44
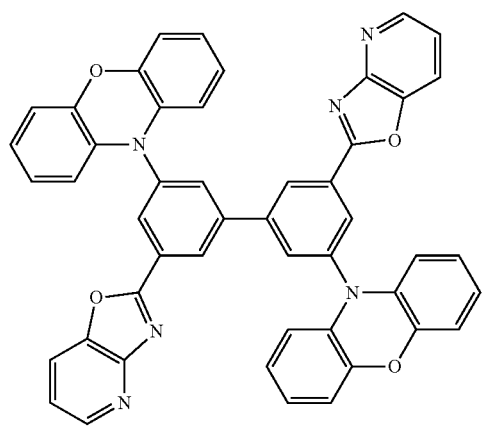
45
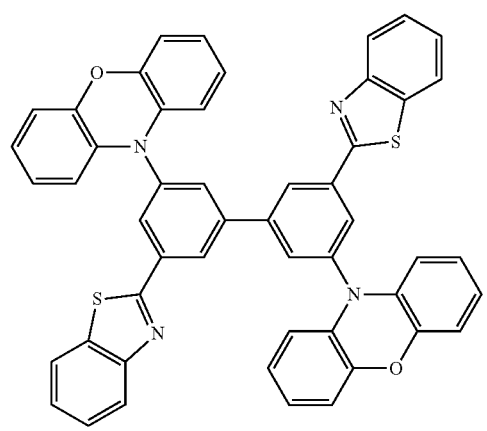
46
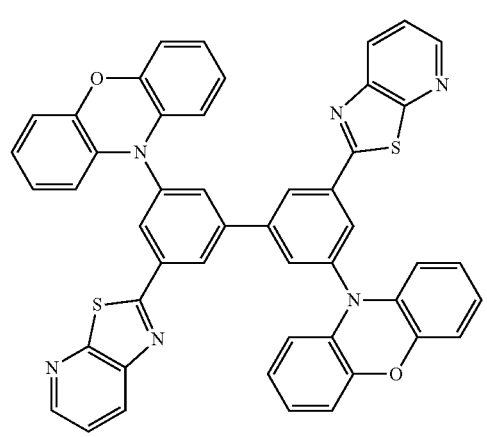
47
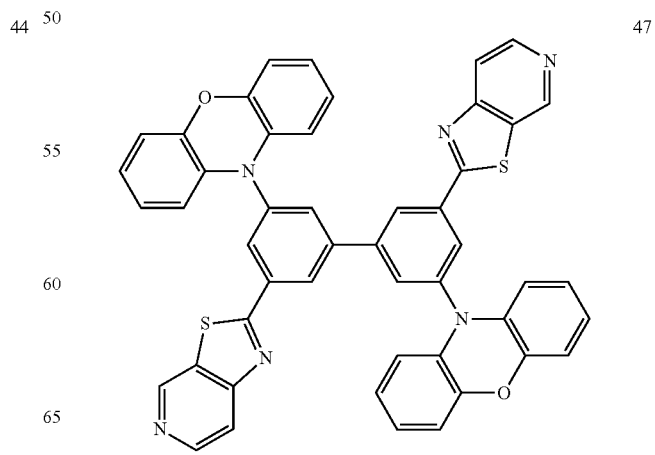

48
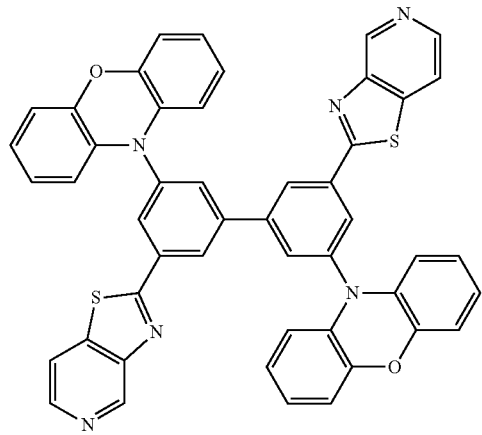
51
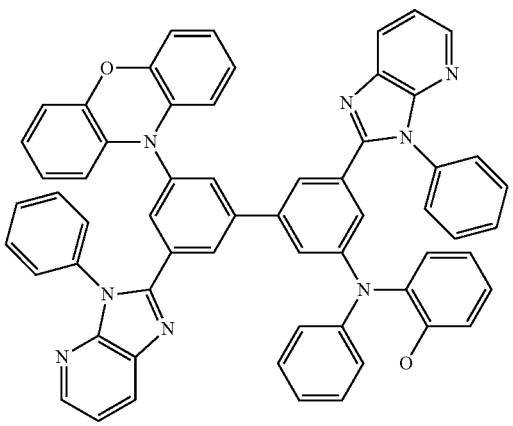
49
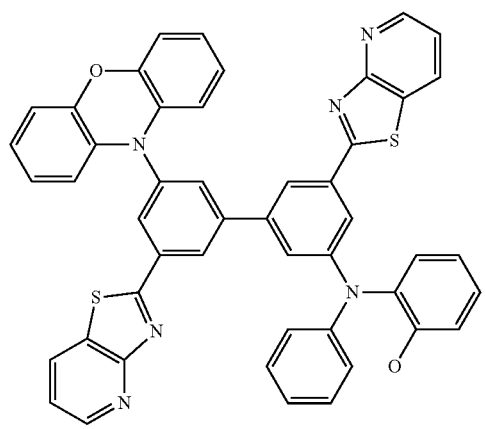
52
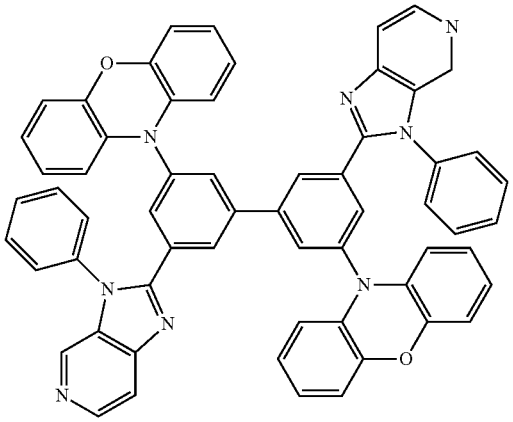
50
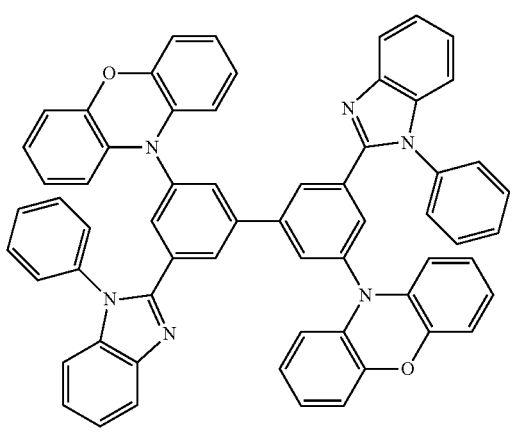
53
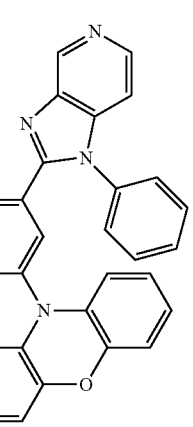

54
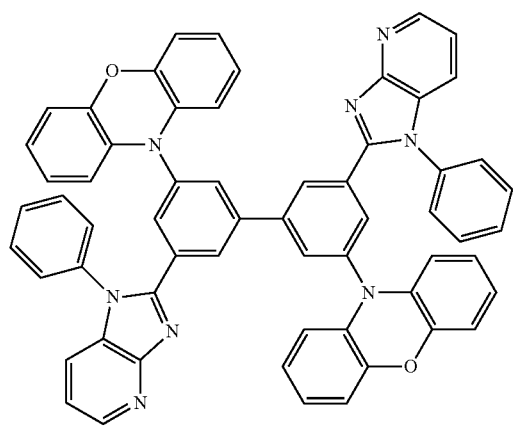
55
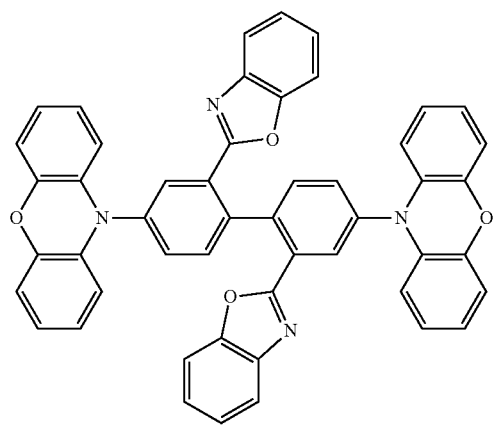
56
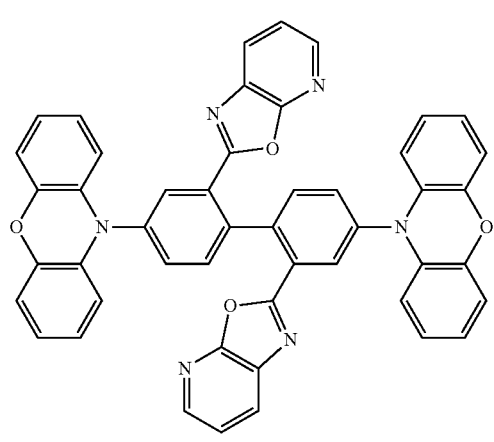
57
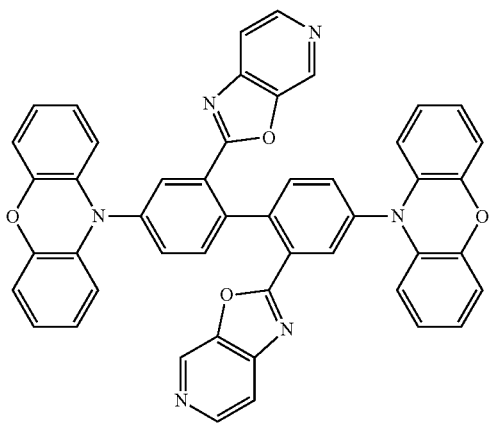
58
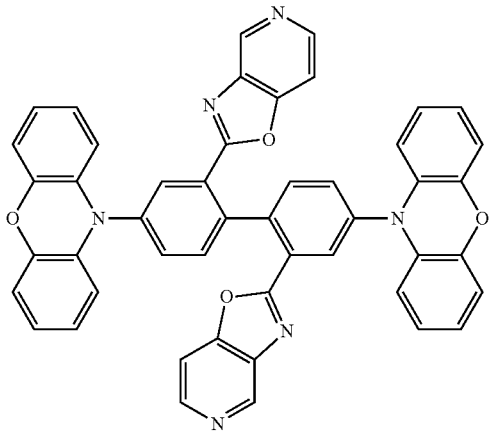
59
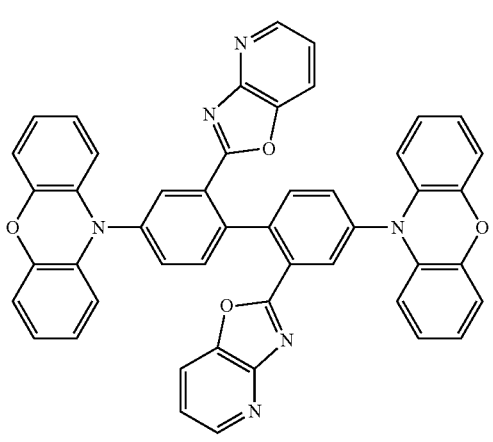

60
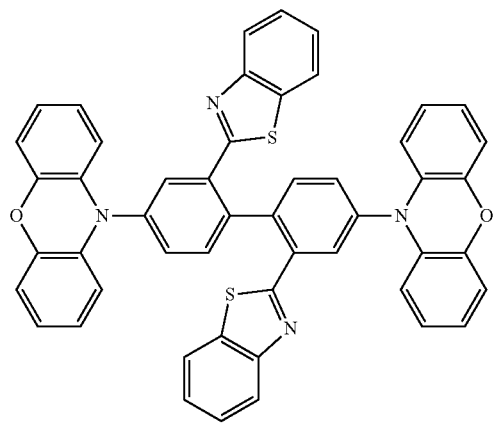
63
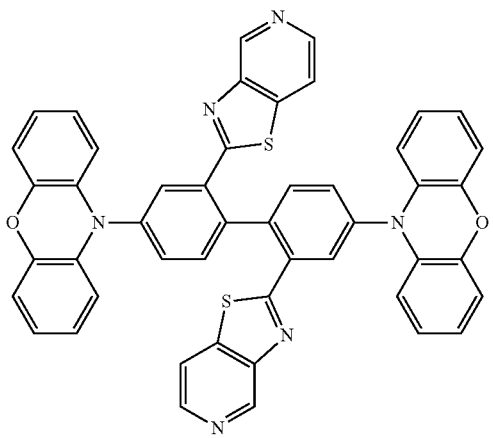
61
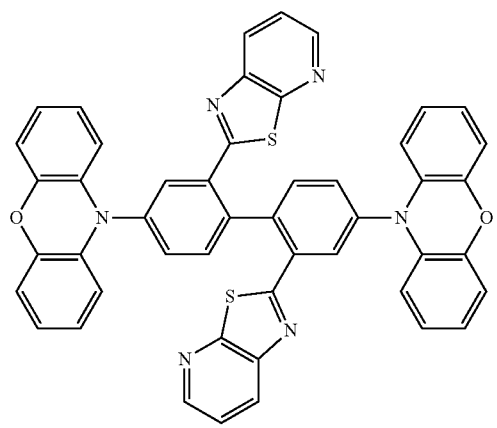
64
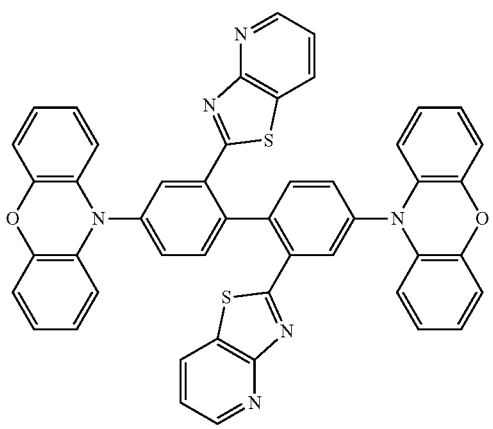
62
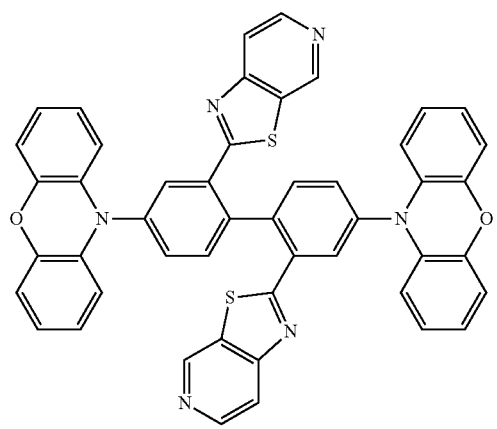
65
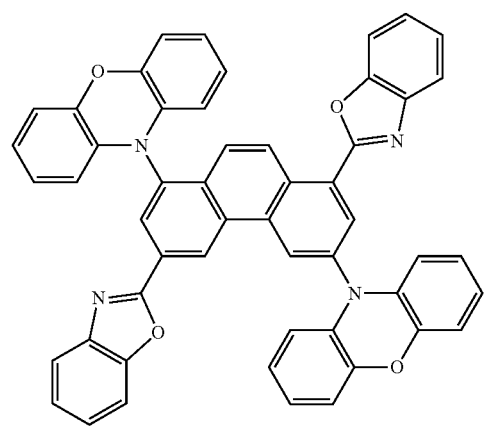

25
-continued
66
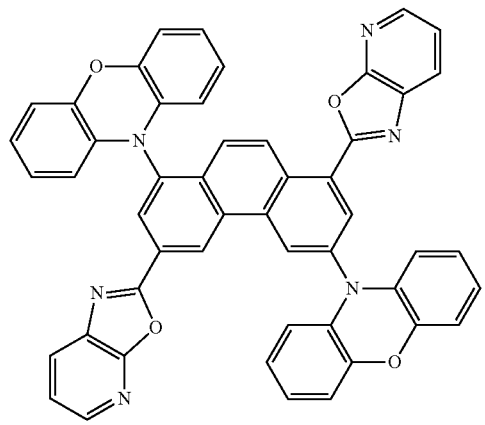
67
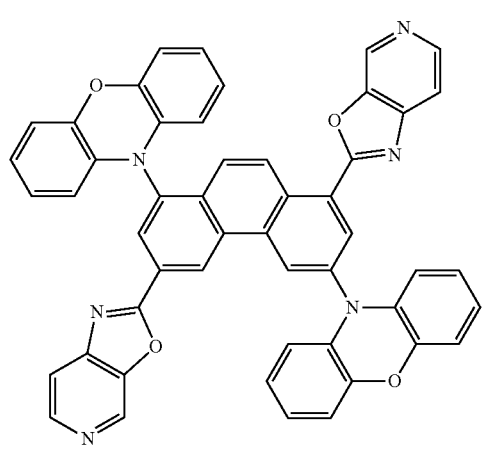
68
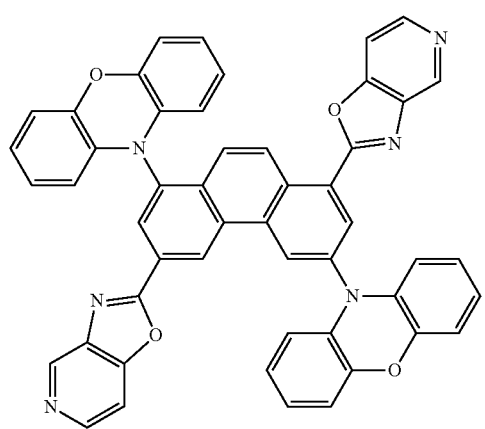
26
-continued
69
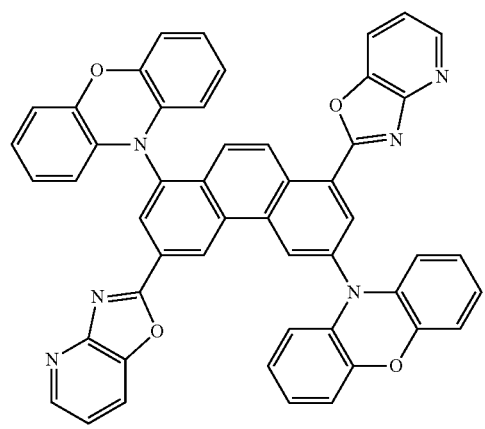
70
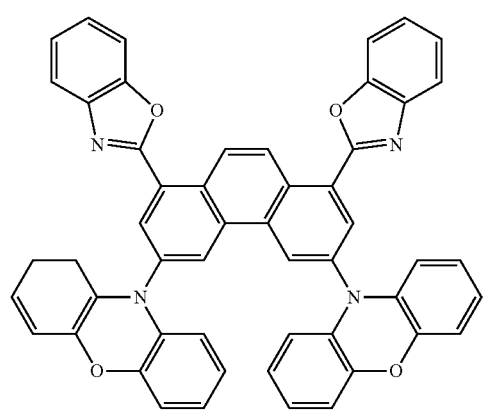
71
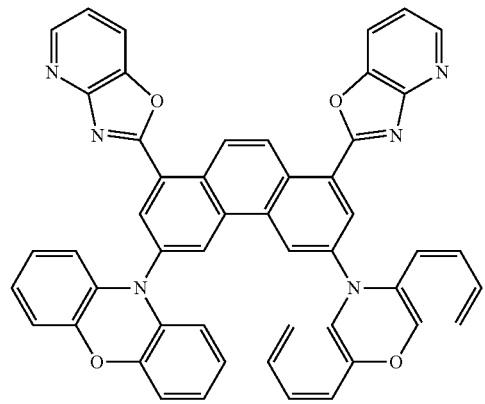
72

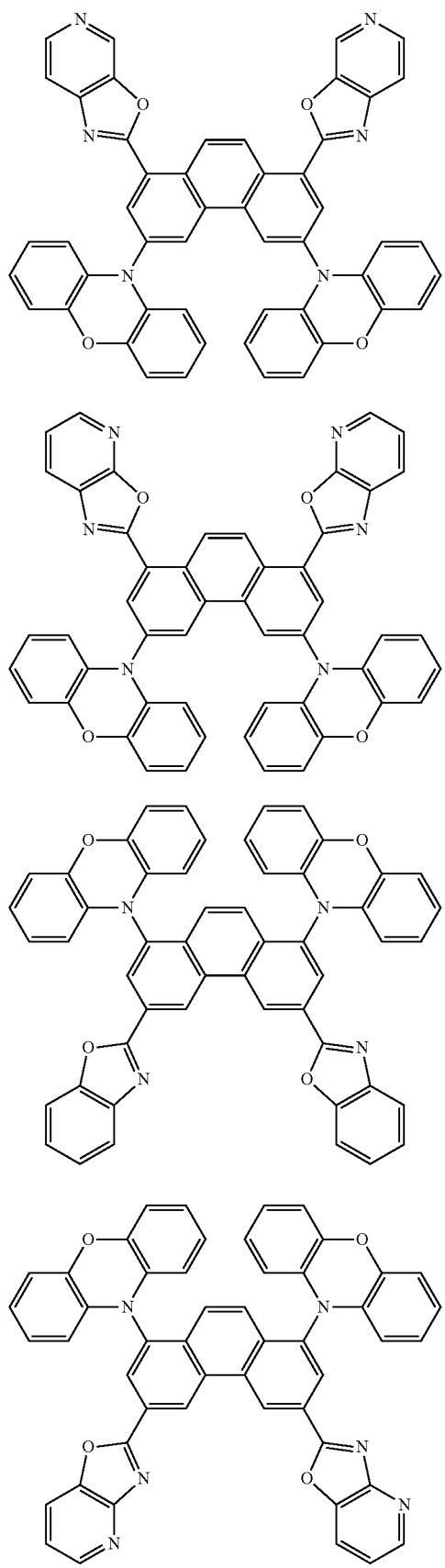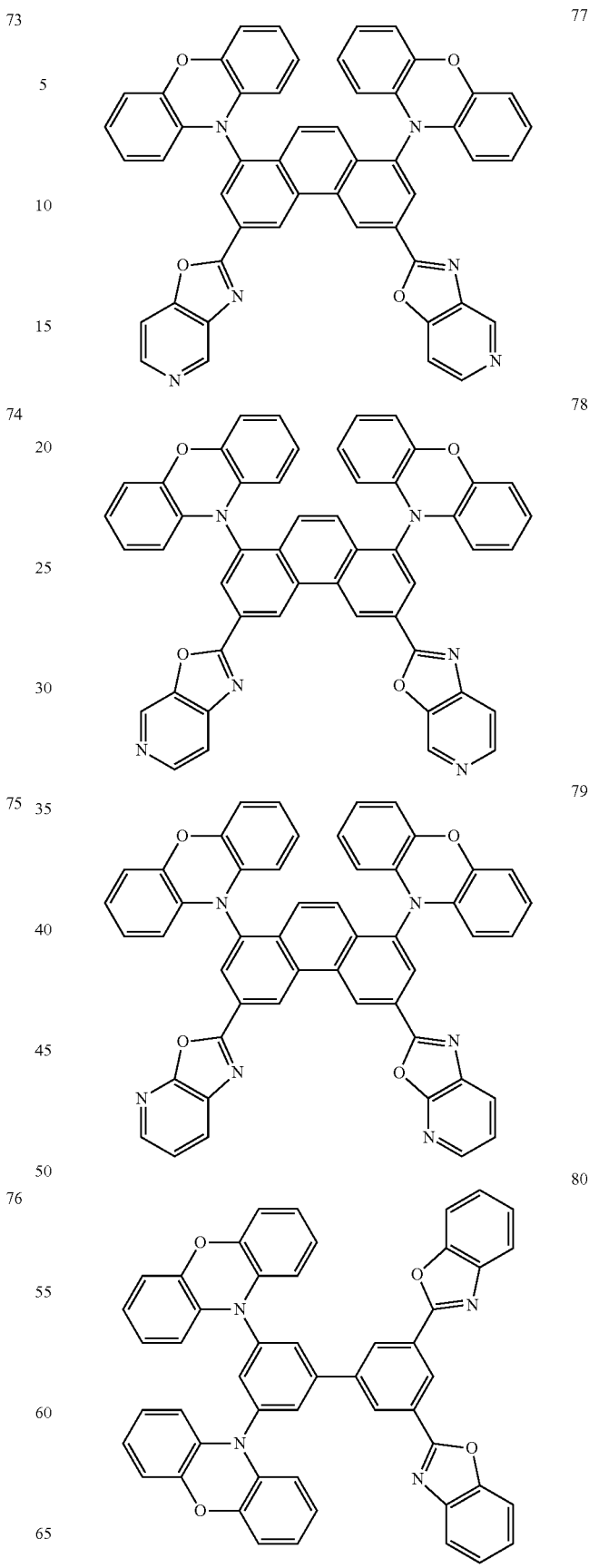

81
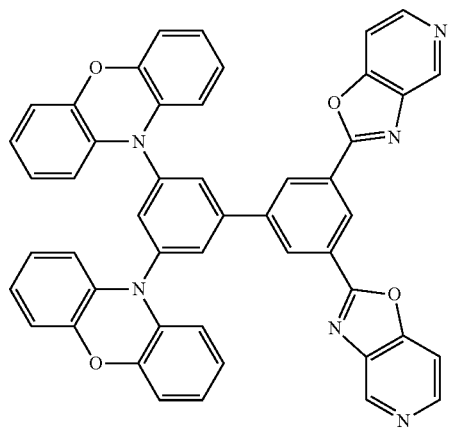
82
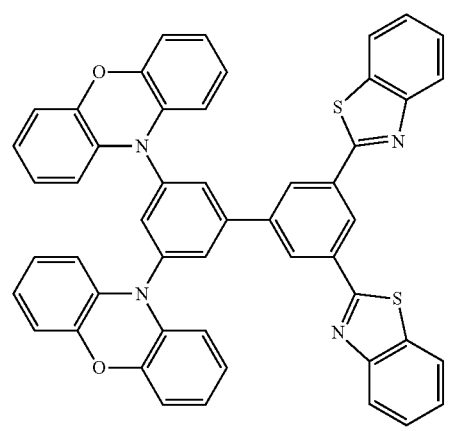
83
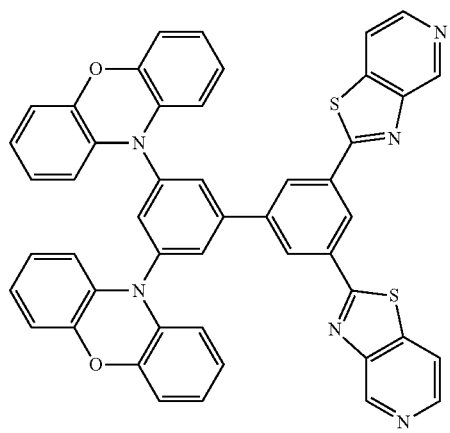
84
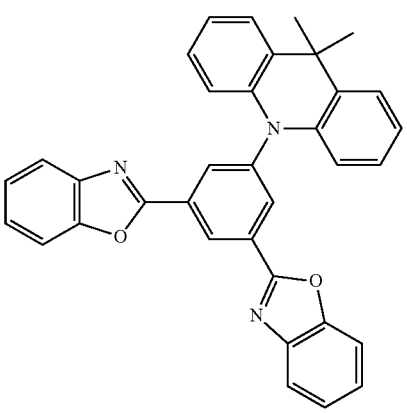
85
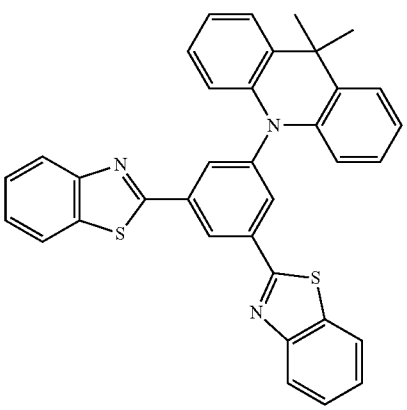
86
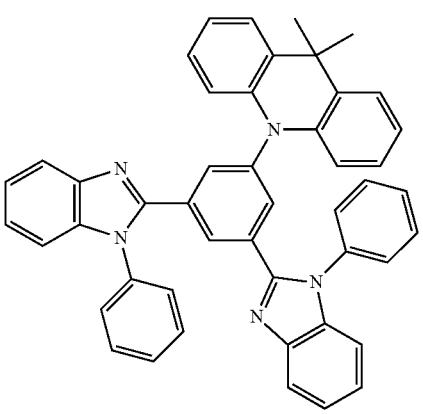
87
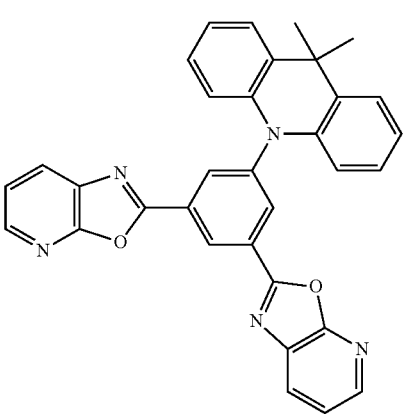

89
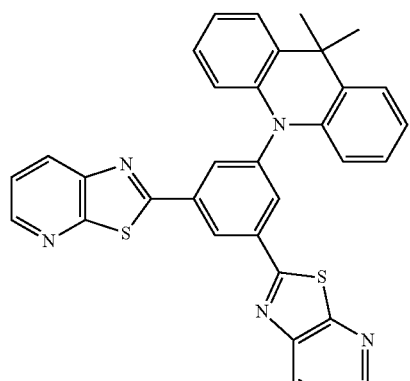
90
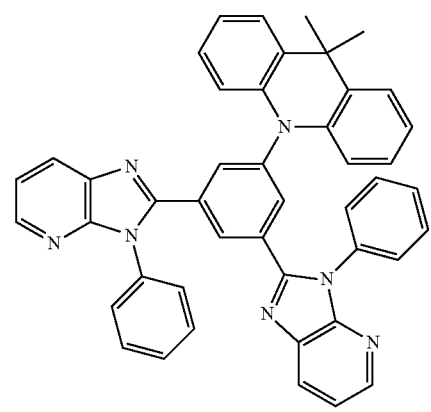
91
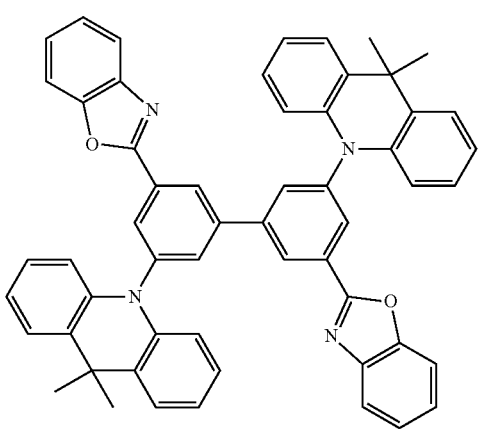
92
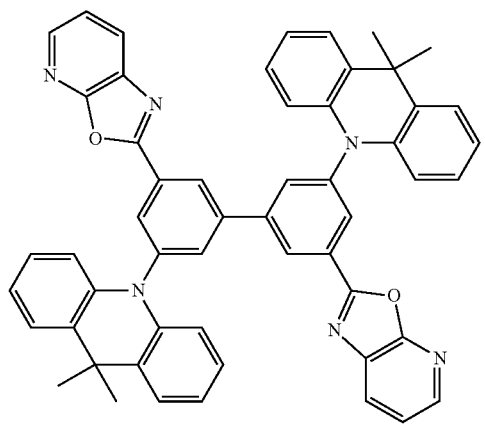
93
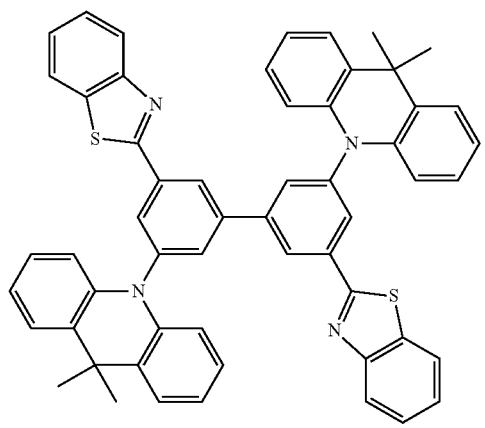
94
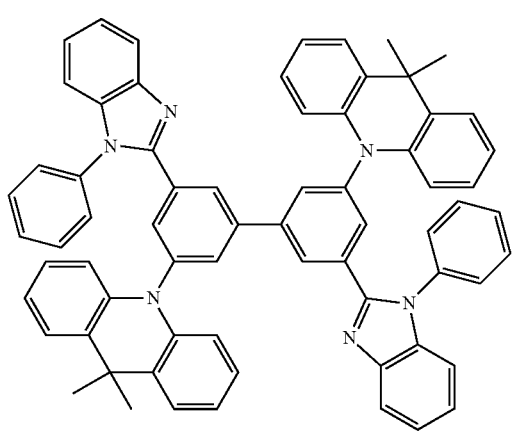

95
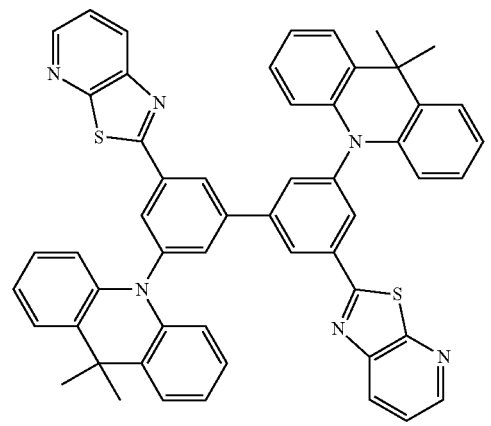
96
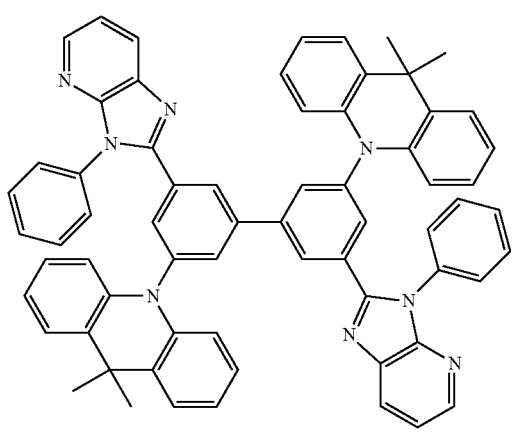
97
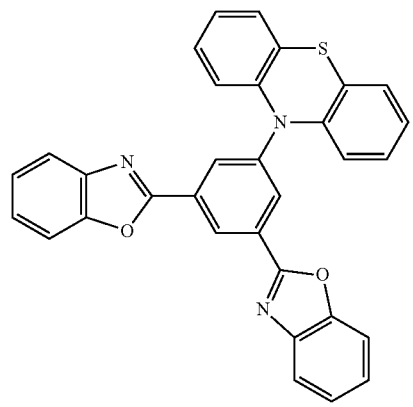
98
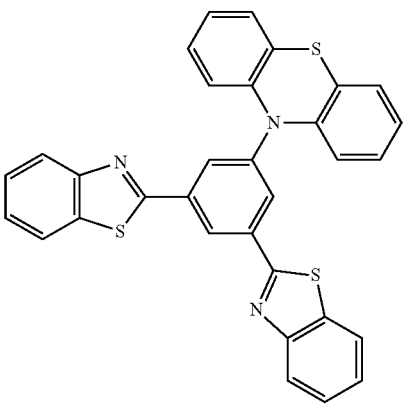
99
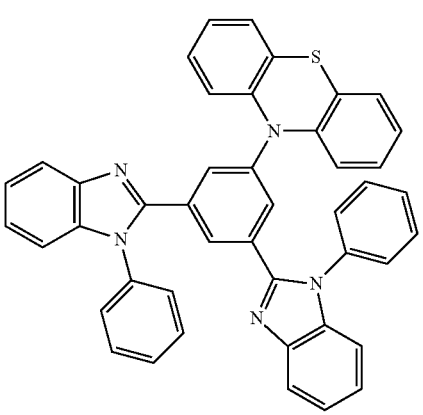
100
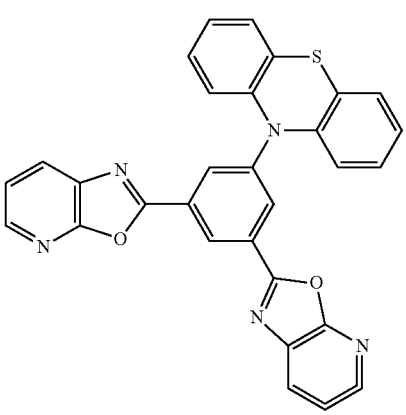
101
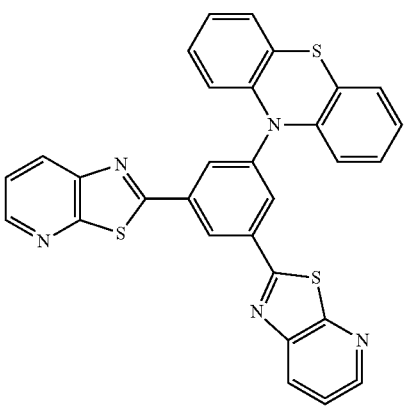

35
-continued
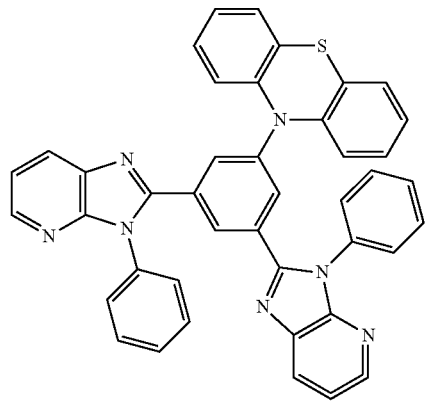
102
36
-continued
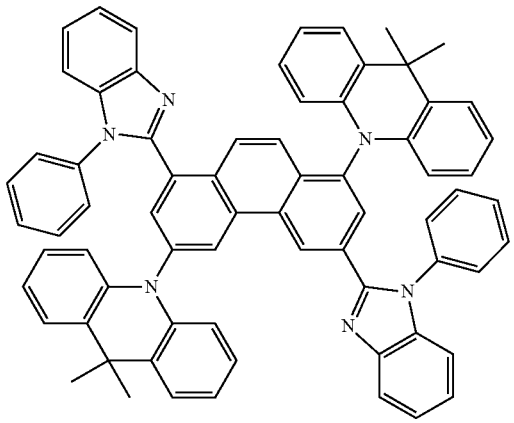
105
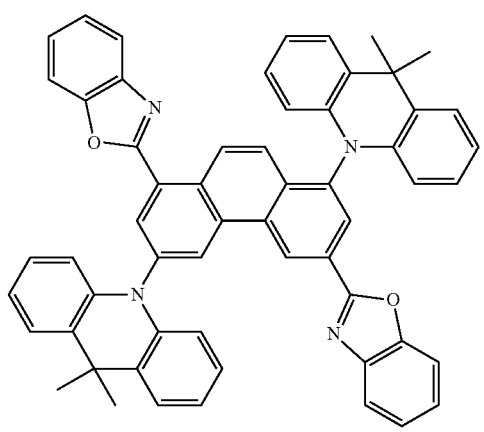
103
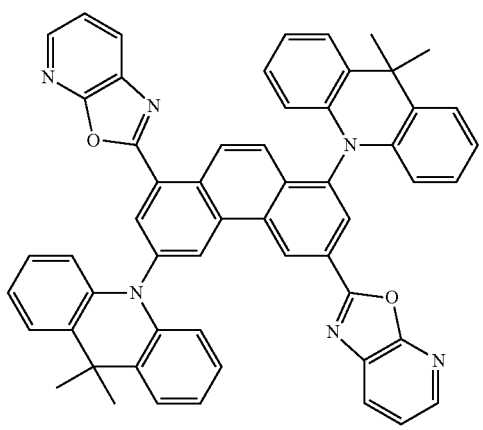
106
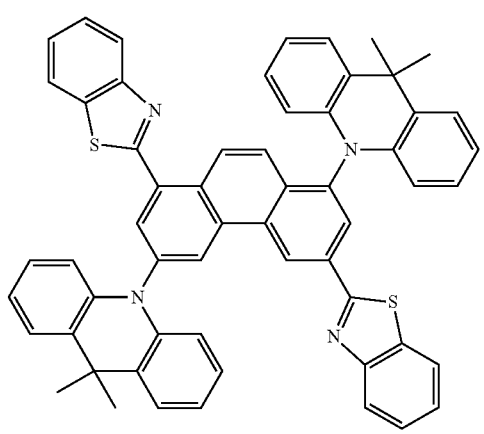
104
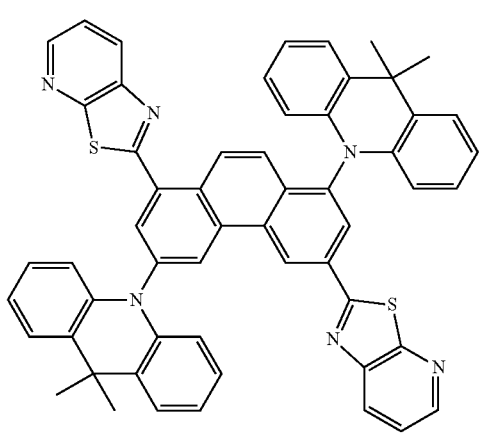
107

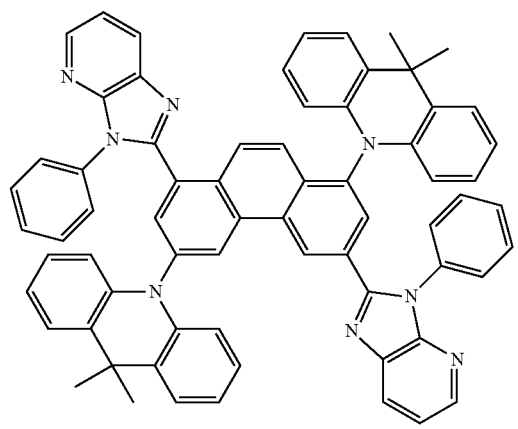
108
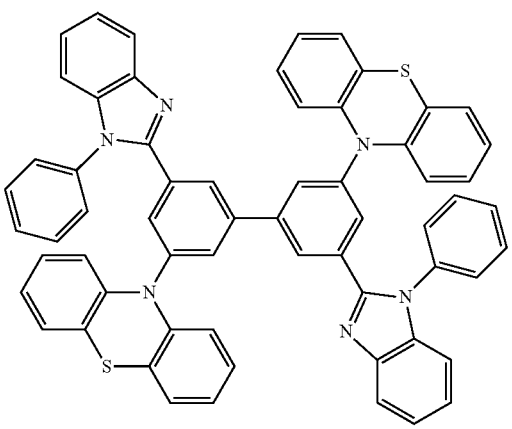
111
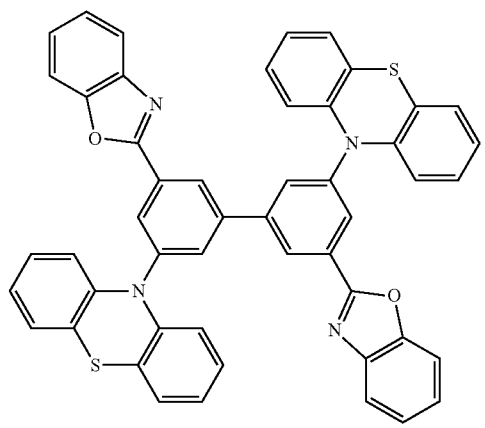
109
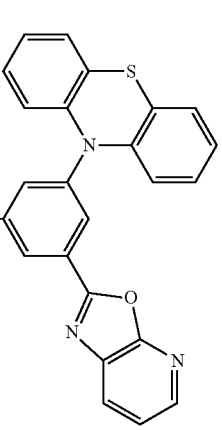
112
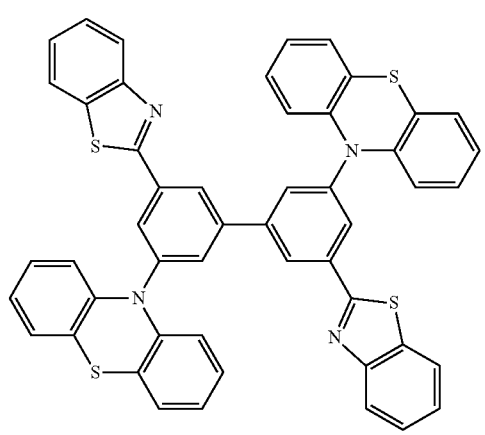
110
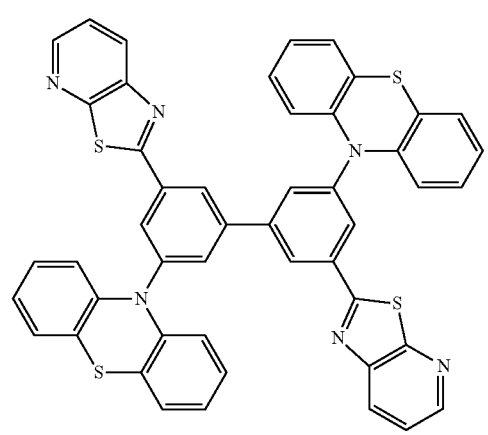
113

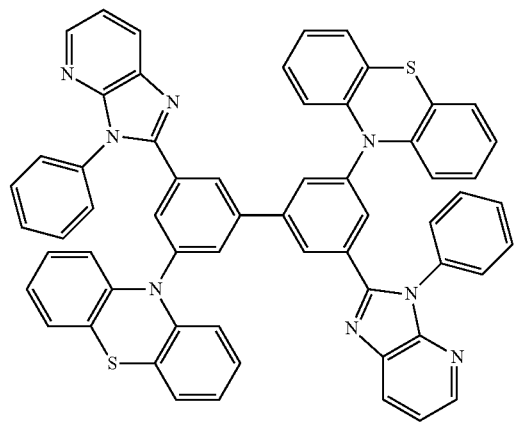
114
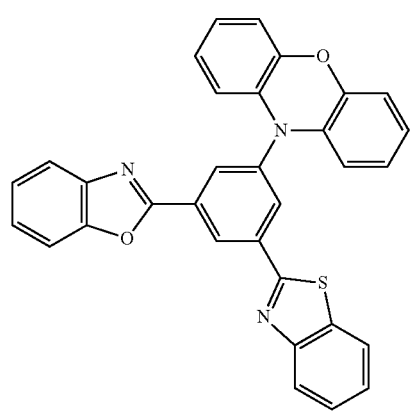
115
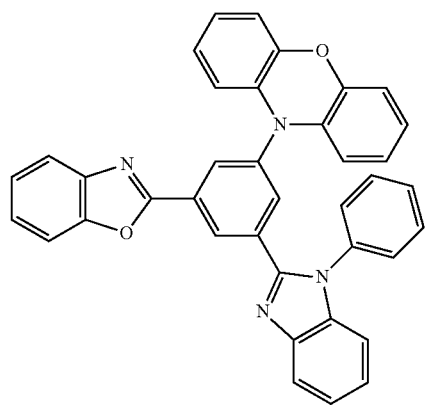
116
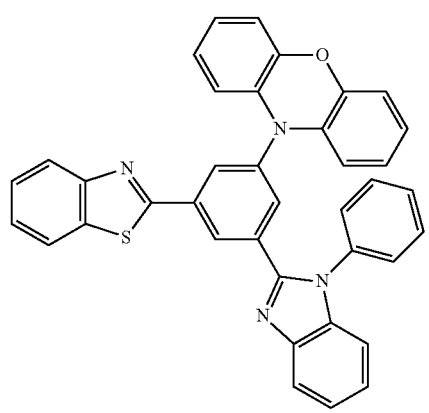
117
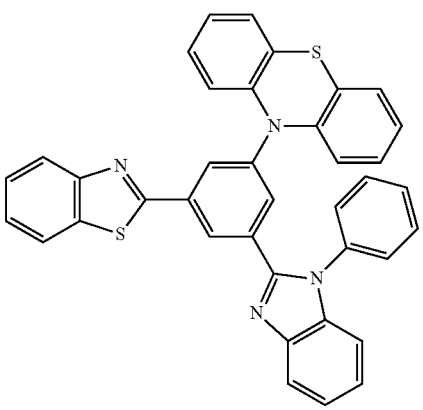
118
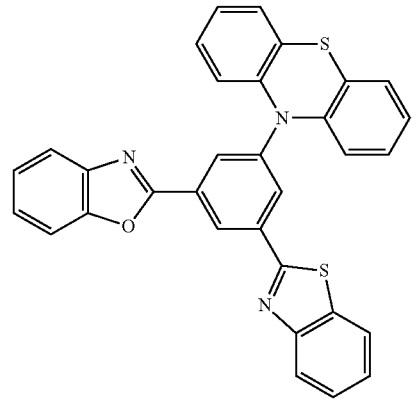
119
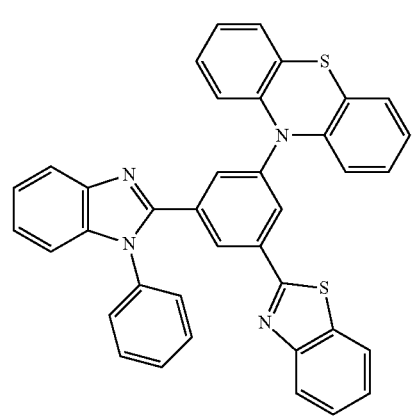
120
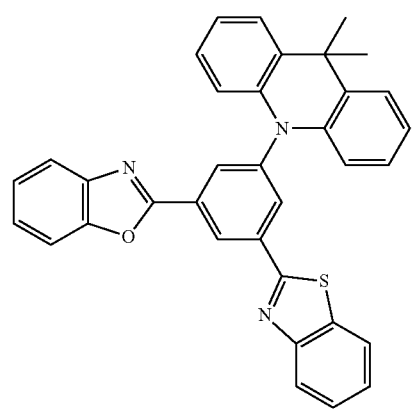
121

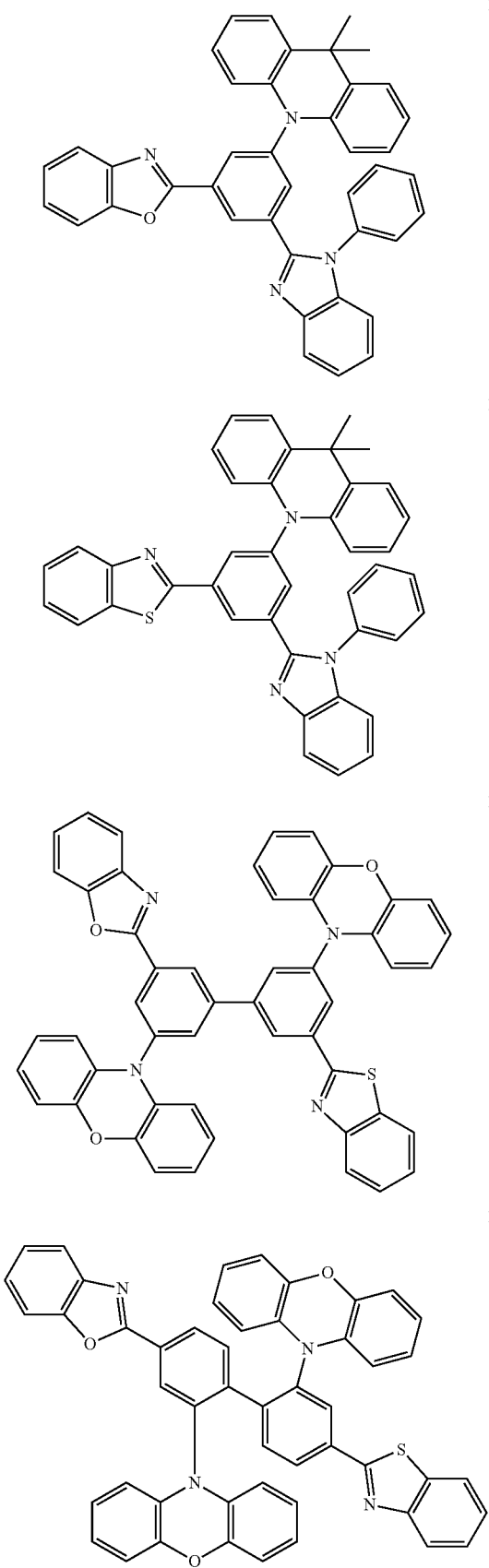
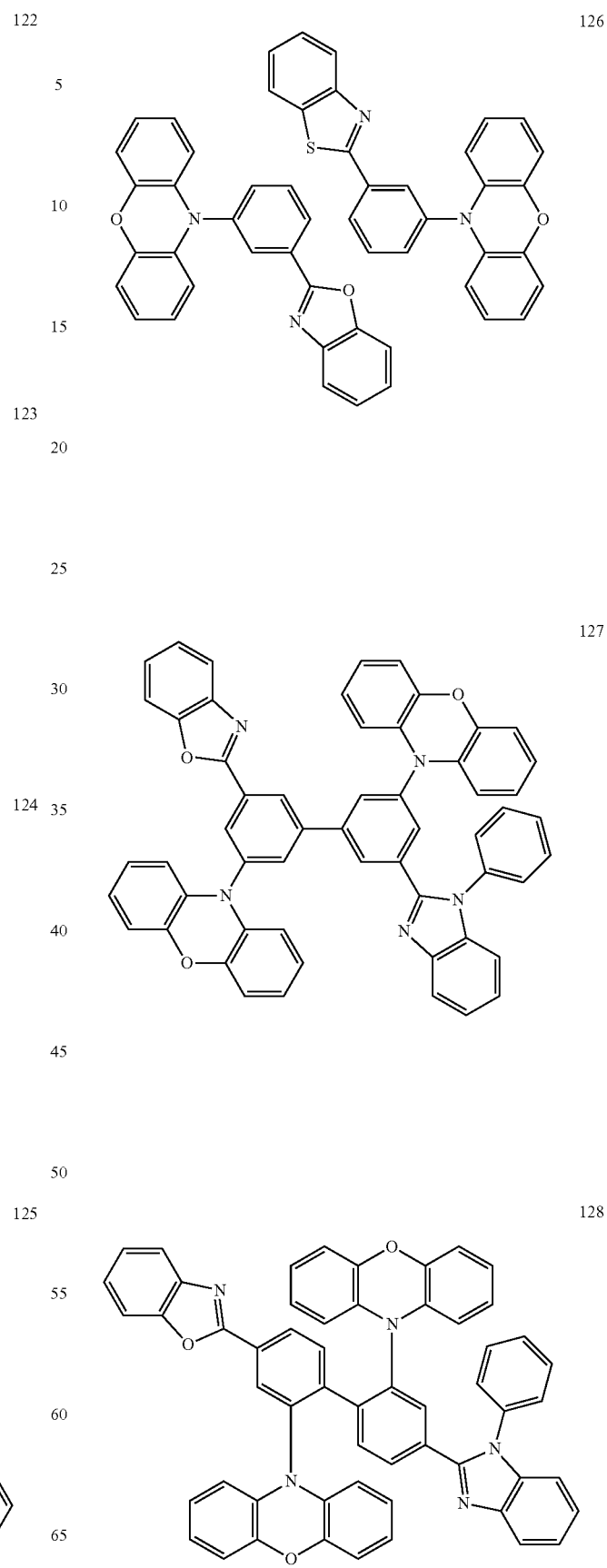

129
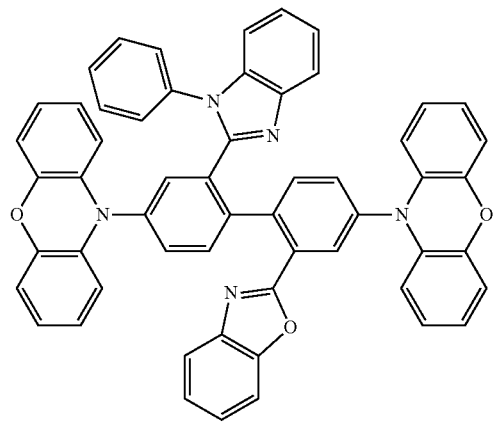
130
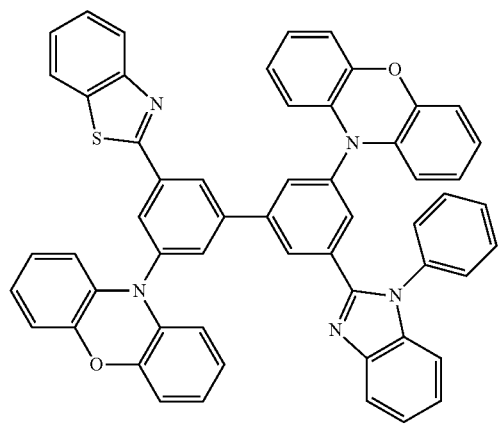
131
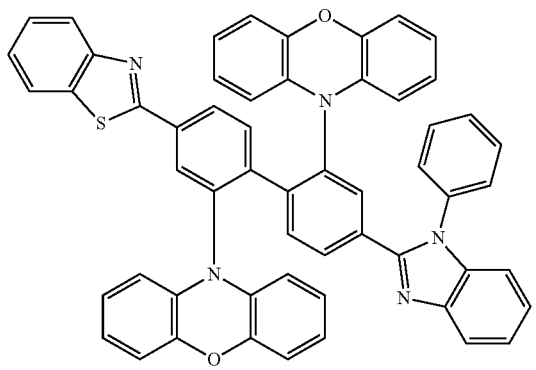
132
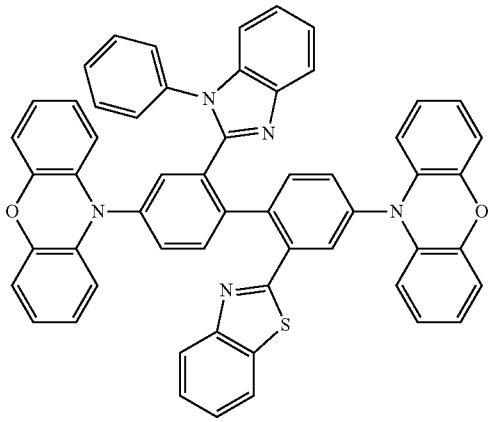
133
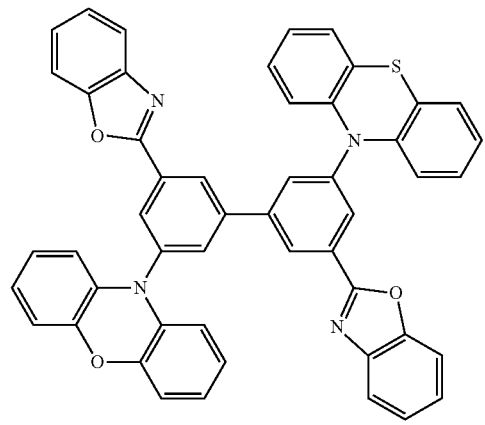
134
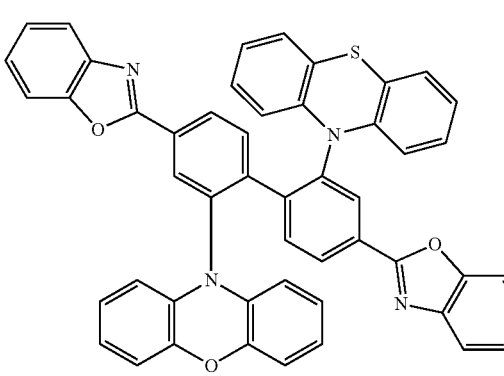
135
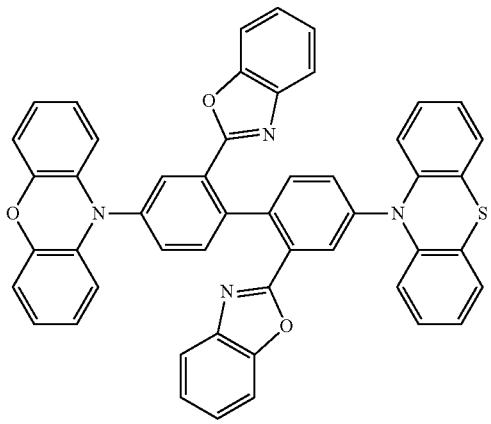

-continued
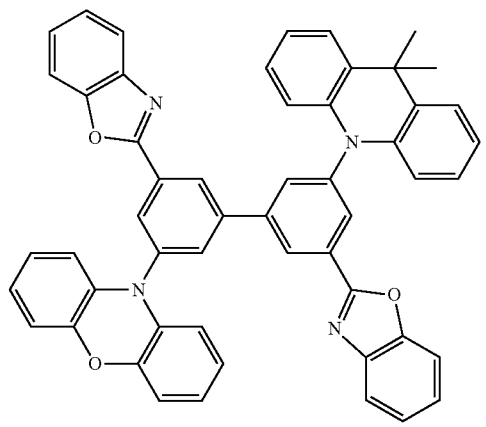
136
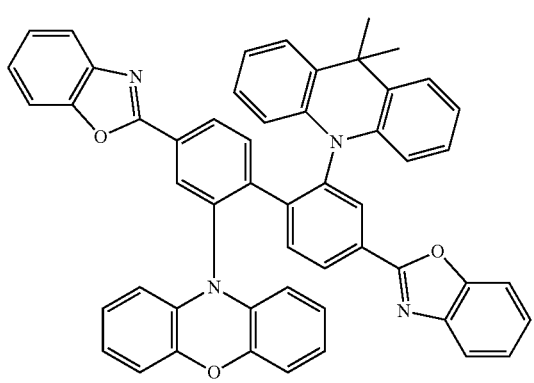
137
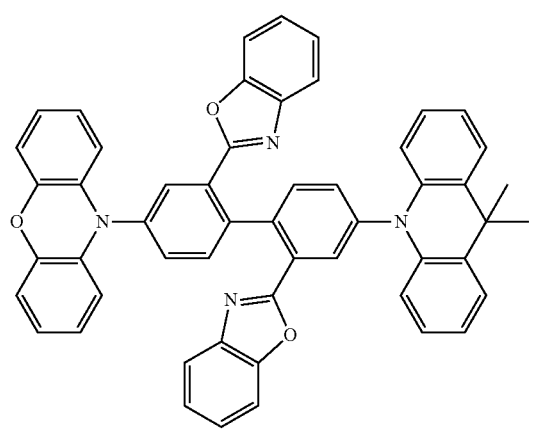
138
-continued
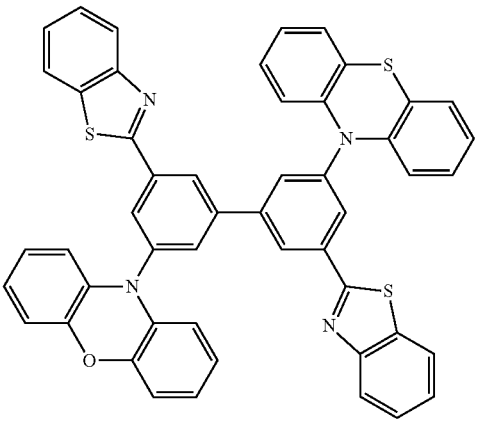
139
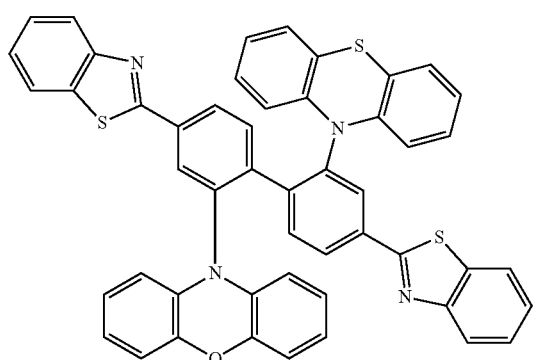
140
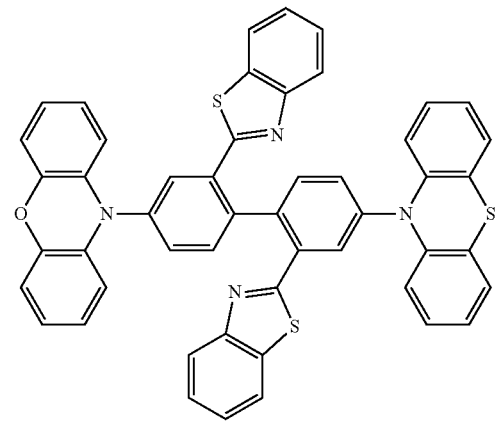
141
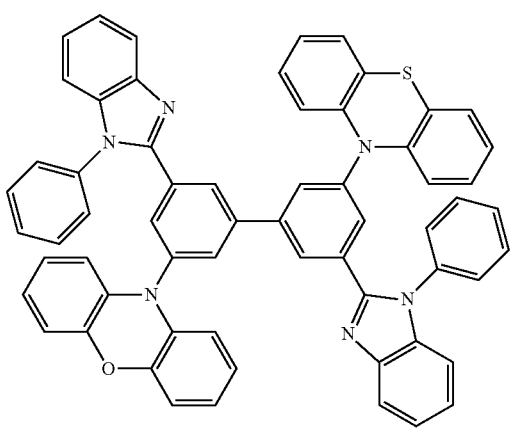
142

143
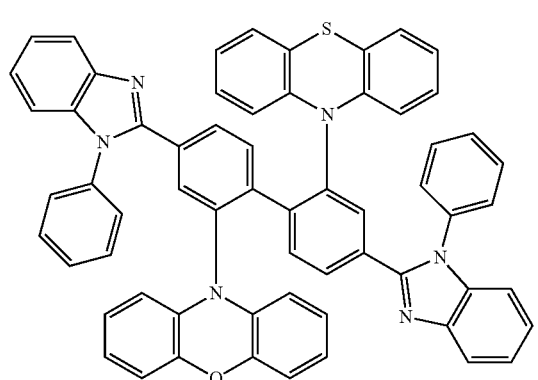
144
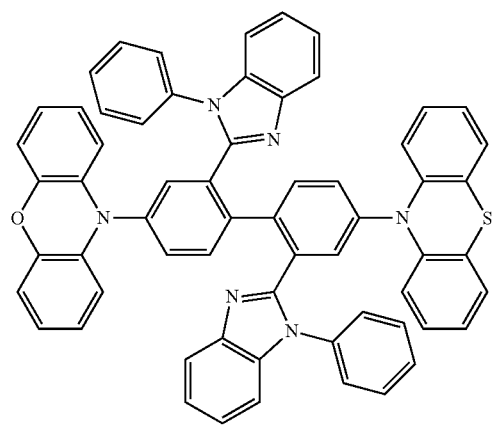
145
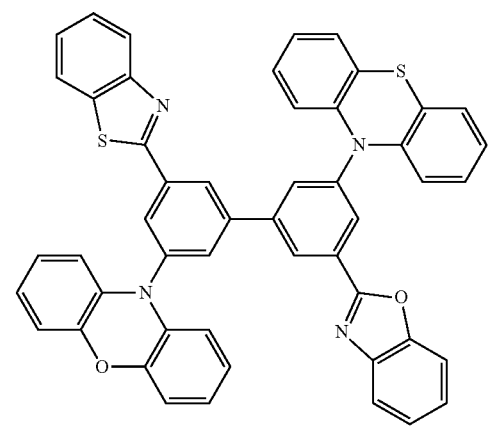
146
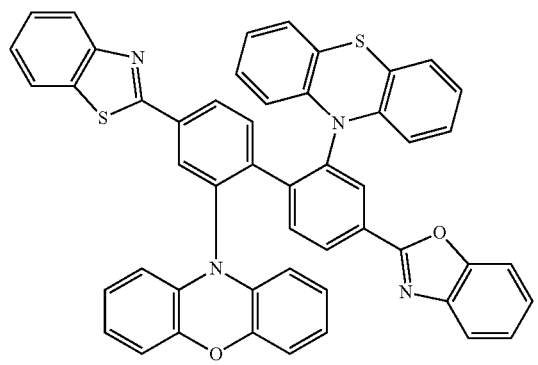
147
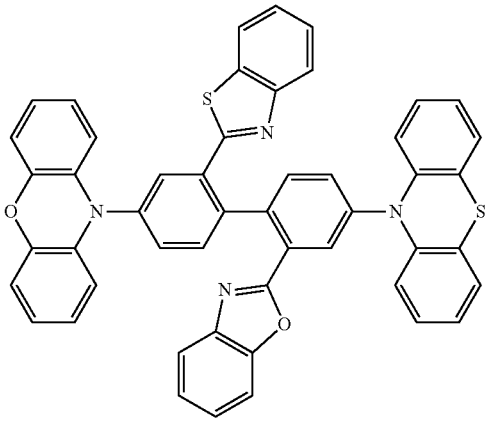
148
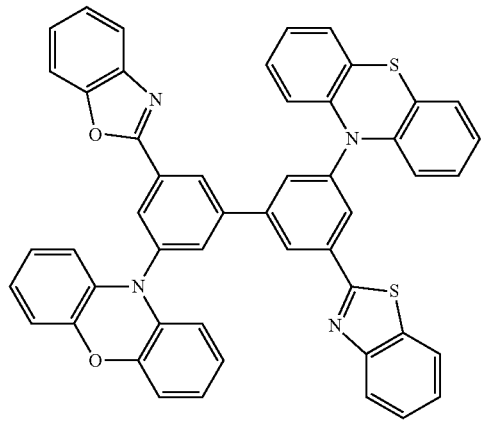
149
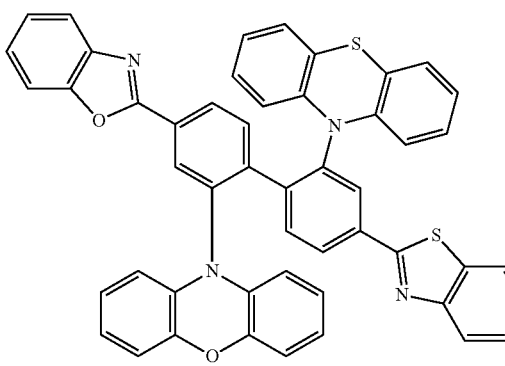

150 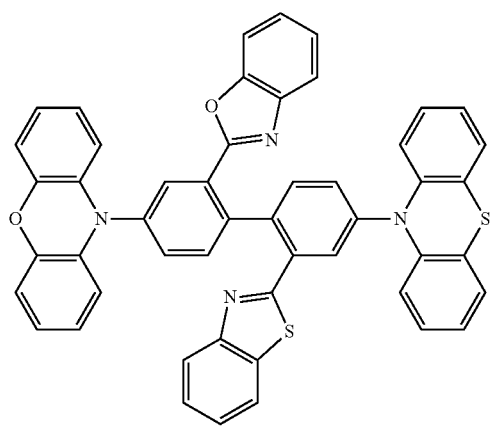
151 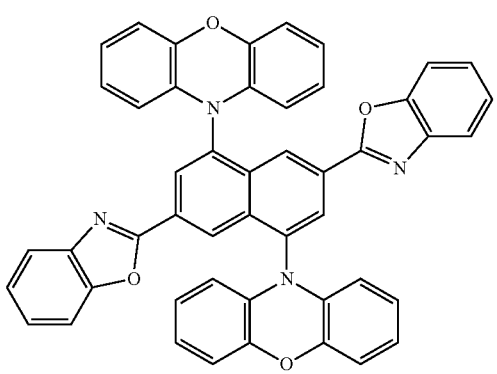
152 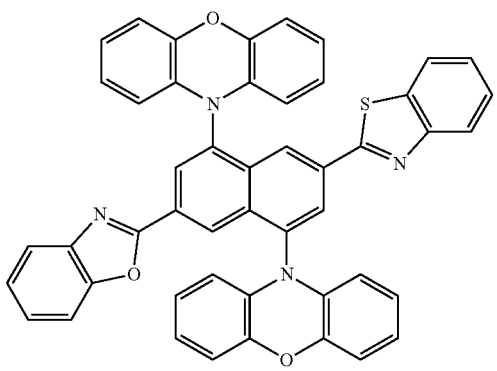
153 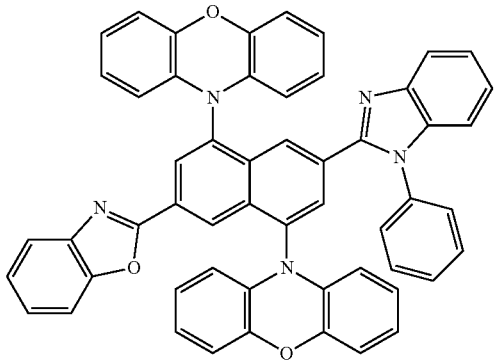
154 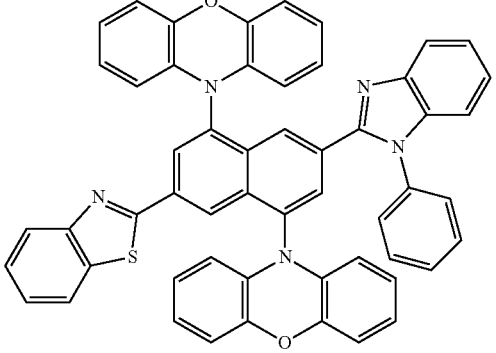
155 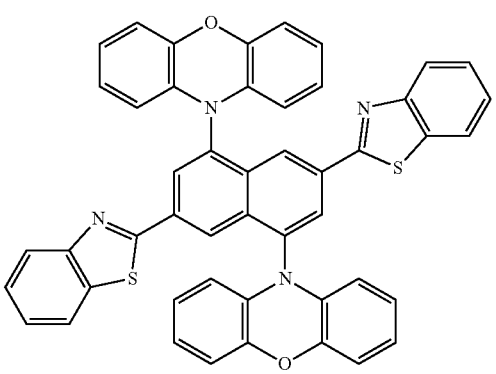
156 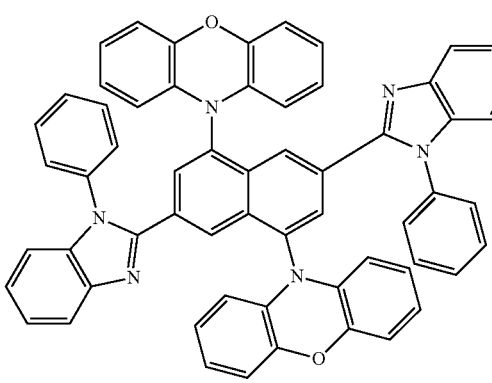
157 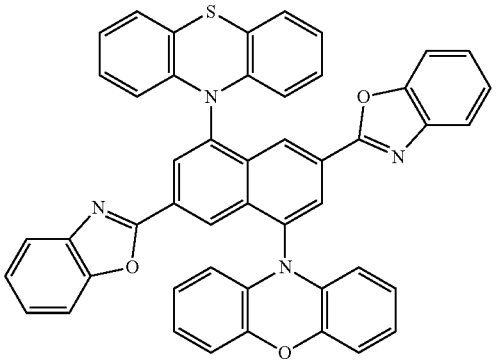

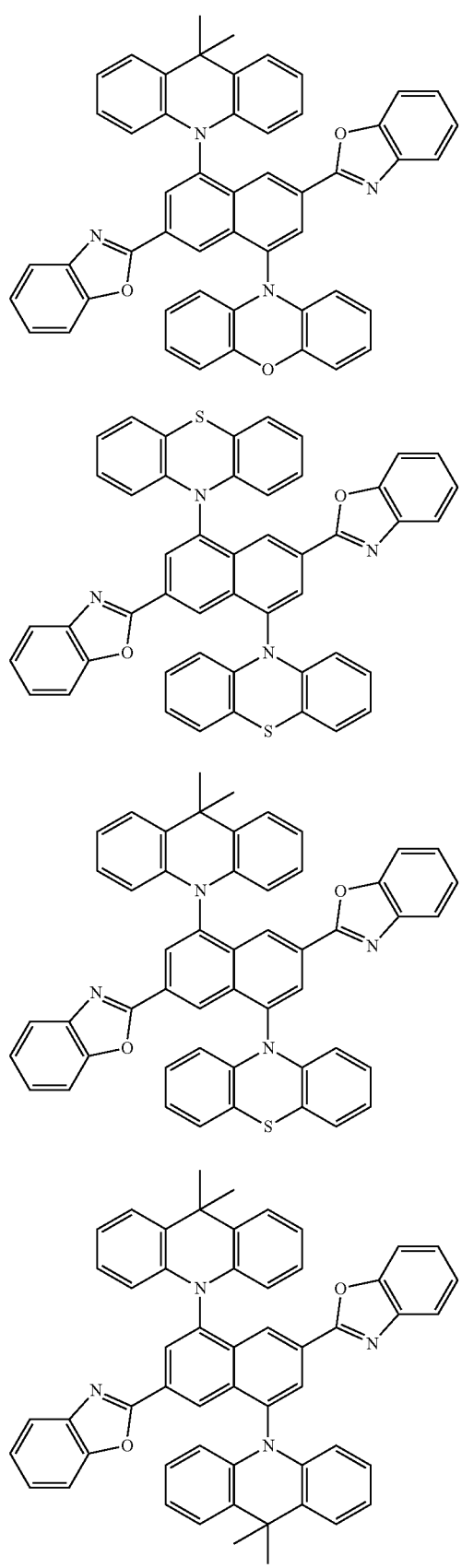
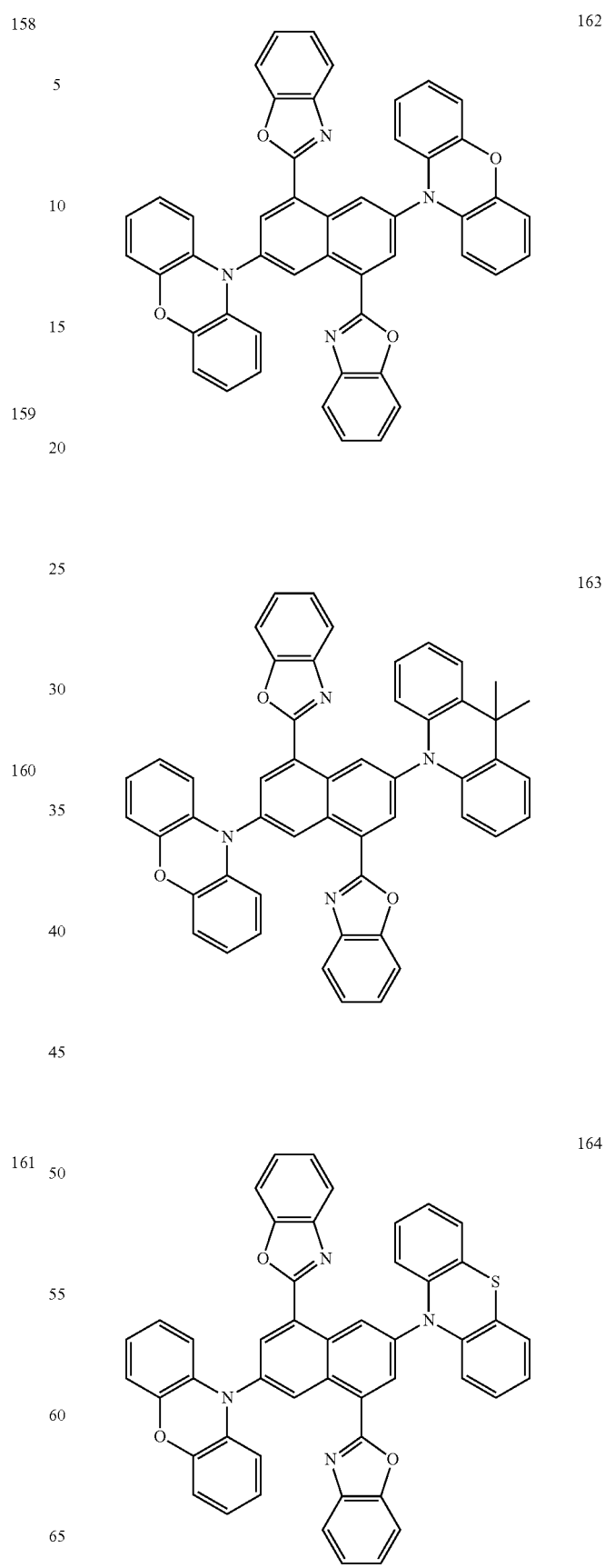

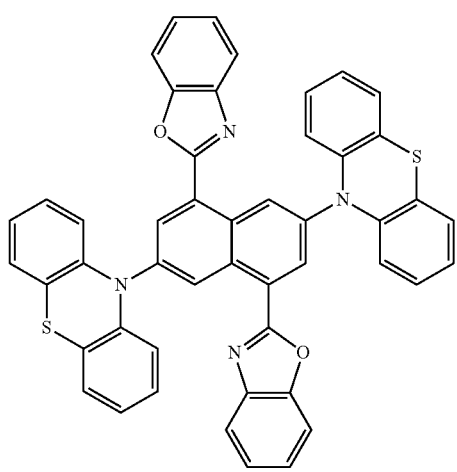

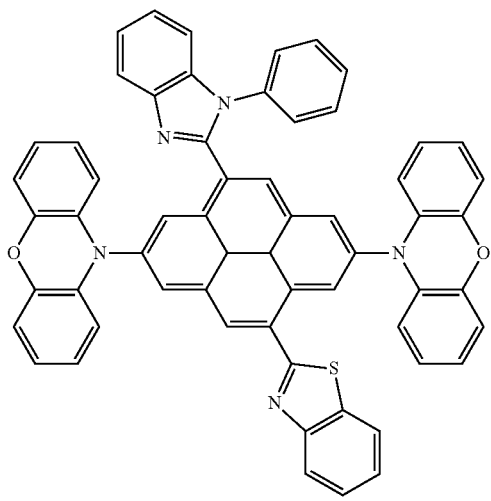

171

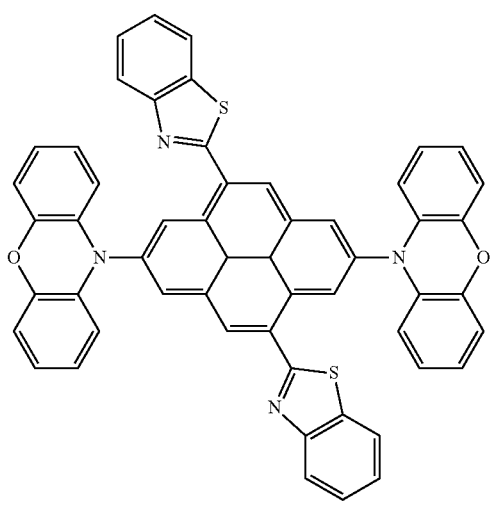

172

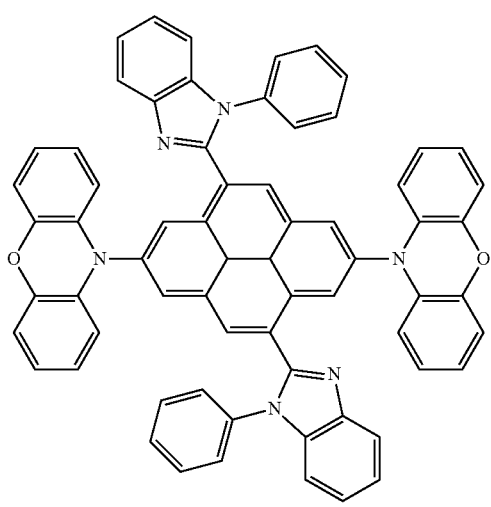

173

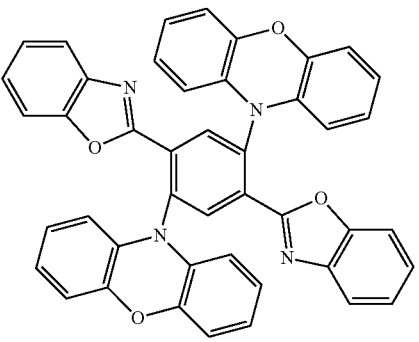

174

In one embodiment, use of the above-mentioned compounds in an organic optoelectronic device is provided.

In one embodiment, an organic optoelectronic device is provided, the device comprises an anode, a cathode and one or more organic layers located between the anode and the cathode, and at least one layer of the organic layers comprises one or more compounds in the table above.

In one embodiment, at least one layer of the organic layers is a luminescent layer, and the luminescent layer comprises the above-mentioned compound.

In one embodiment, the organic layer further comprises a hole transport layer, a hole injection layer, an electron blocking layer, a hole blocking layer, an electron transport layer, an electron injection layer or a combination thereof.

In one embodiment, materials for manufacture of the anode comprise the following materials: metals such as copper, gold, silver, iron, chromium, nickel, manganese, palladium, platinum, or a mixture thereof; an alloy of copper, gold, silver, iron, chromium, nickel, manganese, palladium, or platinum; metal oxides such as indium oxide, zinc oxide, indium tin oxide (ITO), indium zinc oxide (IZO), or a mixture thereof; conductive polymers such as polyaniline, polypyrrole, poly(3-methylthiophene), or a mixture thereof.

In one embodiment, materials for manufacture of the cathode comprise the following materials: metals such as aluminum, magnesium, silver, indium, tin, titanium, calcium, sodium, potassium, lithium, ytterbium, lead or a mixture thereof; multilayer metallic materials such as LiF/Al, Liq(8-hydroxyquinoline)/Al or a mixture thereof.

In one embodiment, the above-mentioned compounds are present in the luminescent layer as a doped material or a co-doped material or a host material.

Definitions

Unless otherwise specified, the technical and scientific terms used in the present application have the same meaning as commonly understood by one of ordinary skill in the art. As to the terms which are defined in the present application, the definitions in the application shall prevail.

"Alkyl" refers to a fully saturated (no double or triple bonds) hydrocarbyl which may be straight-chain or branched-chain. Alkyl may contain 1-30 carbon atoms, 1-20 carbon atoms, 1-10 carbon atoms, or 1-6 carbon atoms. For example, the numerical range of "1-30" refers to all the integers in the range, including 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. For example, the alkyl may be selected from methyl, ethyl, propyl, isopropyl, n-butyl, isobutyl, sec-butyl, tert-butyl, pentyl and hexyl, etc. An alkyl may be substituted or unsubstituted. "Aryl" refers to a carbocyclic ring (all atoms are carbon atoms) having a completely delocalized π-electron system throughout all the rings, which includes monocyclic aryl or multicyclic aryl. The multicyclic aryl is a system containing two or more aromatic rings such as benzene ring, the two or more aromatic rings may be linked to each other by a single bond or fused to each other by a common bond. The number of carbon atoms in the aryl group is variable. For example, the aryl group may contain 6-30 carbon atoms. For example, the numerical range of "6-30" refers to all integers in the range, including 6, 7, 8, 9, 10, 11, 12, 13, 14, 15, 16, 17, 18, 19, 20, 21, 22, 23, 24, 25, 26, 27, 28, 29 or 30. Examples of the aryl group include, but are not limited to, phenyl, biphenyl, naphthyl, anthryl, phenanthryl or pyrenyl. The aryl group may be substituted or unsubstituted. "Heteroaryl" refers to a monocyclic or multicyclic aromatic ring system containing one or more heteroatoms, in which the heteroatom is an element other than carbon, including but not limited to, nitrogen, oxygen and sulfur. The number of carbon atoms in the heteroaryl ring can vary. For example, the heteroaryl group may contain 1-20 carbon atoms in the ring, the numerical range such as "1-20" refers to all integers in the range, including 1, 2, 3, 4, 5, 6, 7, 8, 9, 10, 11, 12, 13, 14, 15, 16, 17, 18, 19 or 20. For another example, the heteroaryl group may contain 1-30 cyclic backbone atoms in the ring, the numerical range such as "1-30" refers to all integers in the range, including 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. Moreover, the term "Heteroaryl" comprises fused ring system, in which two rings (e.g., at least one aryl ring and at least one heteroaryl ring or at least two heteroaryl rings) share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

Organic Optoelectronic Device

The organic optoelectronic device in the present application comprises an organic electroluminescent diode, an organic solar cell, an organic photoelectric sensor, an organic memory device and the like. The organic electroluminescent diode will be explained below.

The organic electroluminescent diode comprises an anode, a cathode, and one or more organic layers located between the anode and the cathode. At least one layer of the organic layers is a luminescent layer, and the luminescent layer comprises the compounds of the present application. The organic electroluminescent diode further comprises a hole transport layer (HTL), a hole injection layer (HIL), an electron blocking layer (EBL), a hole blocking layer (HBL), an electron transport layer (ETL), an electron injection layer (EIL), or a combination thereof, and at least one layer of these layers comprises the organic compounds described in the present application. The compounds are present in the luminescent layer as a doped material, a co-doped material or a host material.

FIGS. 1 to 5 are structure schematic drawings of the organic electroluminescent diode comprising the compounds of the present application, wherein:

100, substrate;
110, anode;
120, cathode;
130, luminescent layer;
140, hole transport layer;
150, electron transport layer;
160, hole injection layer;
170, electron injection layer;
180, electron blocking layer;
190, hole blocking layer.

According to FIGS. 1 to 5, the structure of the organic electroluminescent diode comprises an anode layer 110 and a cathode layer 120 on the substrate layer 100. At least a luminescent layer 130 is comprised between the anode layer 110 and the cathode layer 120.

According to FIG. 1, the organic electroluminescent diode only comprises a luminescent layer 130 between the anode layer 110 and the cathode layer 120. Electrons and holes excite the luminescent layer to emit light after the luminescent layer is combined.

Figure 2:
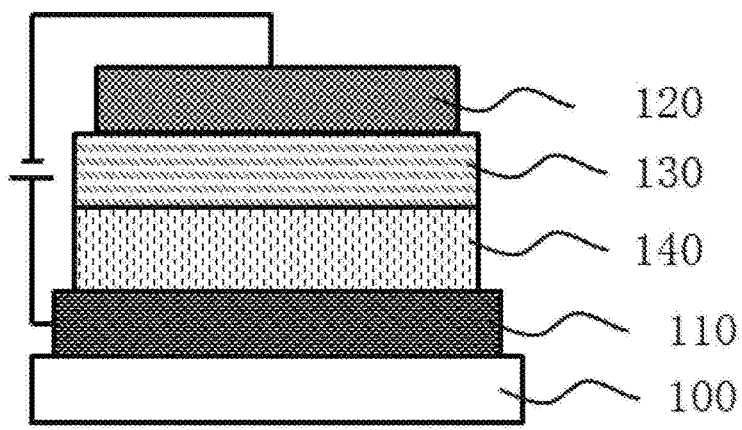
FIG. 2 illustrates an exemplary structure of an organic electroluminescent diode according to a second embodiment of the present invention.

According to FIG. 2, the organic electroluminescent diode comprises a hole transport layer (HTL) 140 and a luminescent layer 130 between the anode layer 110 and the cathode layer 120. The hole transport layer mainly plays a role of transferring the holes to the luminescent layer.

Figure 3:
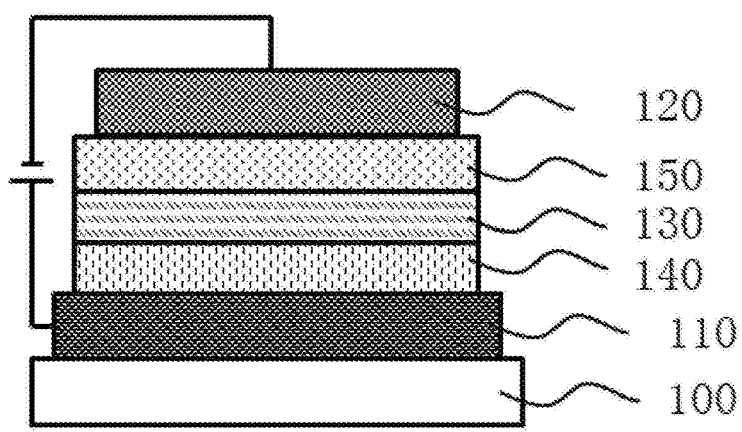
FIG. 3 illustrates an exemplary structure of an organic electroluminescent diode according to a third embodiment of the present invention.

According to FIG. 3, the organic electroluminescent diode comprises a hole transport layer (HTL) 140, a luminescent layer 130 and an electron transport layer (ETL) 150 between the anode layer 110 and the cathode layer 120. The electron transport layer mainly plays a role of transferring the electrons to the luminescent layer.

Figure 4:
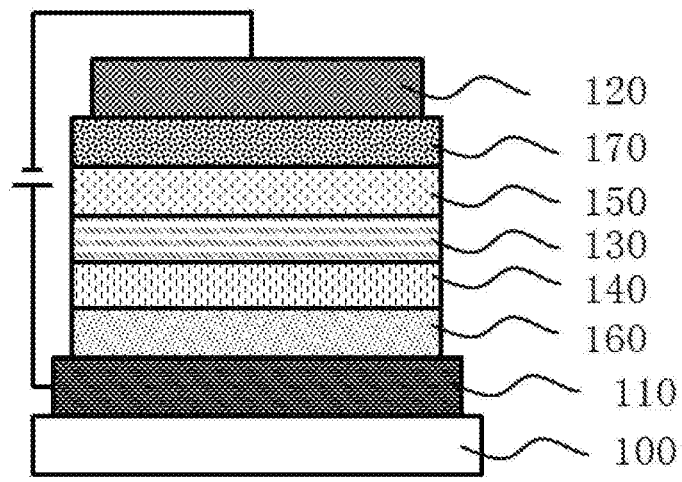
FIG. 4 illustrates an exemplary structure of an organic electroluminescent diode according to a fourth embodiment of the present invention.

According to FIG. 4, the organic electroluminescent diode comprises a hole injection layer (HIL) 160, a hole transport layer (HTL) 140, a luminescent layer 130, an electron transport layer (ETL) 150 and an electron injection layer (EIL) 170 between the anode layer 110 and the cathode layer 120. The hole injection layer mainly improves the ability to transferring the holes to the organic layer from the anode, and the electron injection layer mainly improves the ability to transferring the electrons to the organic layer from the cathode, so as to reduce the driving voltage of the diode.

Figure 5:
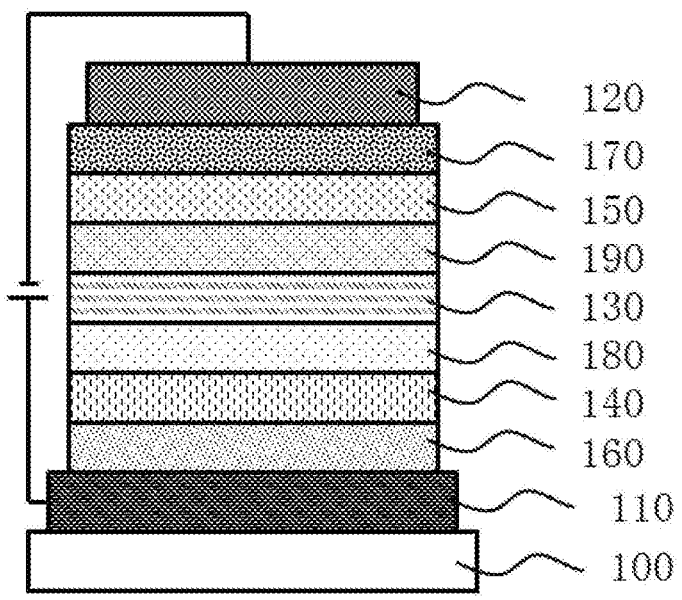
FIG. 5 illustrates an exemplary structure of an organic electroluminescent diode according to a fifth embodiment of the present invention.

According to FIG. 5, the organic electroluminescent diode comprises a hole injection layer (HIL) 160, a hole transport layer (HTL) 140, an electron blocking layer (EBL) 180, a luminescent layer 130, a hole blocking layer (HBL) 190 and an electron transport layer (ETL) 150 between the anode layer 110 and the cathode layer 120.

The materials of each layer are illustrated by examples below, and thus are not limited to the materials below.

The anode layer 110 can use electrode materials having a large work function. The materials which can be used as the anode may comprise: metals such as copper, gold, silver, iron, chromium, nickel, manganese, palladium, platinum, or a mixture thereof; an alloy of copper, gold, silver, iron, chromium, nickel, manganese, palladium, or platinum and the like; metal oxides such as indium oxide, zinc oxide, indium tin oxide (ITO), indium zinc oxide (IZO), or a mixture thereof; conductive polymers such as polyaniline, polypyrrole, poly(3-methylthiophene), or a mixture thereof. Preferably, indium tin oxide (ITO) is used in the examples comprising the organic compounds of the present application as the material of the anode layer.

The cathode layer 120 can use electrode materials having a low work function. The materials which can be used as the cathode may comprise: metals such as aluminum, magnesium, silver, indium, tin, titanium, calcium, sodium, potassium, lithium, ytterbium, lead or a mixture thereof; multilayer metallic materials comprising LiF/Al, Liq(8- hydroxyquinoline)/Al or a mixture thereof. Preferably, magnesium-silver alloy or LiF/Al bilayer material was used in the examples comprising the organic compounds of the present application as the material of the cathode layer.

The hole injection layer (HIL) 160 can use materials which benefit to increase the hole injection of the interface between the anode the organic layer and have good binding property with ITO anode surface. The materials which can be used as the hole injection layer may include: polymeric porphyrin compounds, such as copper phthalocyanine (CuPc); stellate triphenylamine derivatives containing naphthylenediamine, such as 4,4',4''-tris-N-naphthyl-N-phenylamino-triphenylamine (TNATA); polymer materials in which HOMO energy level matches the work function of ITO, such as poly(3,4-ethylenedioxythiophene): polystyrene sulfonate (PEDOT:PSS); electron-withdrawing nitrogen-containing heterocyclic compounds and the like, such as 2,3,6,7,10,11-hexacyano-1,4,5,8,9,12-hexaazatriphenylene (HATCN).

The hole transport layer (HTL) 140 and electron blocking layer (EBL) 180 can use materials having a high glass transition temperature and hole mobility. The materials which can be used as the hole transport layer and electron blocking layer comprise: biphenyldiamine derivatives, such as diphenyl naphthyl diamine (NPD); cross-structure diaminebiphenyl derivatives, such as 2,2',7,7'-tetrakis(diphenylamino)-9,9'-spirobifluorene (spiro-TAD); stellate triphenylamine derivatives and the like, such as 4,4',4''-tris(N-carbazolyl)triphenylamine (TCTA).

The hole blocking layer (HBL) 190 and electron transport layer (ETL) 150 can use materials having a low HOMO level and a high electron mobility. The materials which can be used as the hole blocking layer and electron transport layer include: quinoline-based metal complexes, such as bis(8-hydroxy-2-methylquinoline)-aluminum diphenolate (BAlq), tris(8-hydroxyquinoline) aluminum (Alq) and 8-hydroxyquinolinatolithium; phenanthroline derivatives, such as 4,7-diphenyl-1,10-phenanthroline (Bphen); imidazole derivatives, such as 1,3,5-tris(N-phenyl-benzimidazol-2-yl) benzene (TPBI); triazine derivatives, such as 2,4,6-tricarbazolyl-1,3,5-triazine.

The manufacture method of the organic electroluminescent diode is as follows: forming an anode on a transparent or opaque smooth substrate, forming an organic layer on the anode, and forming a cathode on the organic layer. The organic layer can be formed using well-known film forming method, such as vapor deposition, sputtering, spin coating, dipping, ion plating, etc.

Hereinafter, the present application will be explained in detail by the following examples in order to better understand the various aspects and advantages of the present application. However, it should be understood that the following examples are non-limiting and merely used to illustrate certain embodiments of the present application.

Examples

Simulation Calculation of the Compounds

The simulation calculation of the energy gap between the singlet state and triplet state of the organic material was accomplished by Guassian 09 software (Guassian Inc.). The specific simulation method of the energy gap $\Delta E_{st}$ refers to J. Chem. Theory Comput., 2013, DOI: 10.1021/ct400415r, molecular structure optimization and excitation was accomplished using TD-DFT method "B3LYP" and basis set "6-31g (d)".

Example 1

Compound 29 was simulated according to the above simulation scheme.

Example 2

Compound 30 was simulated according to the above simulation scheme.

Example 3

Compound 55 was simulated according to the above simulation scheme.

Example 4

Compound 40 was simulated according to the above simulation scheme.

Example 5

Compound 174 was simulated according to the above simulation scheme.

Example 6

Compound 1 was simulated according to the above simulation scheme.

Example 7

Compound 65 was simulated according to the above simulation scheme.

Example 8

Compound 70 was simulated according to the above simulation scheme.

Example 9

Compound 33 was simulated according to the above simulation scheme.

Example 10

Compound 80 was simulated according to the above simulation scheme.

Example 11

Compound 168 was simulated according to the above simulation scheme.

Example 12

Compound 151 was simulated according to the above simulation scheme.

Example 13

Compound 84 was simulated according to the above simulation scheme.

Example 14

Compound 91 was simulated according to the above simulation scheme.

Example 15

Compound 103 was simulated according to the above simulation scheme.

The simulation calculation results are shown in Table 1.

TABLE 1

|  | Compound | S1(eV) | T1(eV) | $\Delta E_{st}$(eV) |
| --- | --- | --- | --- | --- |
| Example 1 | 29 | 2.55 | 2.53 | 0.02 |
| Example 2 | 30 | 2.51 | 2.45 | 0.06 |
| Example 3 | 55 | 2.80 | 2.66 | 0.14 |
| Example 4 | 40 | 2.66 | 2.61 | 0.05 |
| Example 5 | 174 | 2.02 | 2.00 | 0.02 |
| Example 6 | 1 | 2.55 | 2.52 | 0.03 |
| Example 7 | 65 | 2.29 | 2.26 | 0.03 |
| Example 8 | 70 | 2.34 | 2.28 | 0.06 |
| Example 9 | 33 | 2.46 | 2.44 | 0.02 |
| Example 10 | 80 | 2.91 | 2.61 | 0.30 |
| Example 11 | 168 | 2.07 | 1.85 | 0.22 |
| Example 12 | 151 | 2.07 | 2.06 | 0.03 |
| Example 13 | 84 | 2.77 | 2.62 | 0.15 |
| Example 14 | 91 | 2.90 | 2.69 | 0.21 |
| Example 15 | 103 | 2.56 | 2.26 | 0.30 |

According to the results shown in Table 1, energy gap $\Delta E_{st}$ between the singlet state and triplet state in Examples 1-15 are small. This suggests that the compounds in Table 1 can achieve efficient reverse intersystem crossing and have TADF performance.

Preparation of the Compounds

Example 16: Synthesis of Compound 29

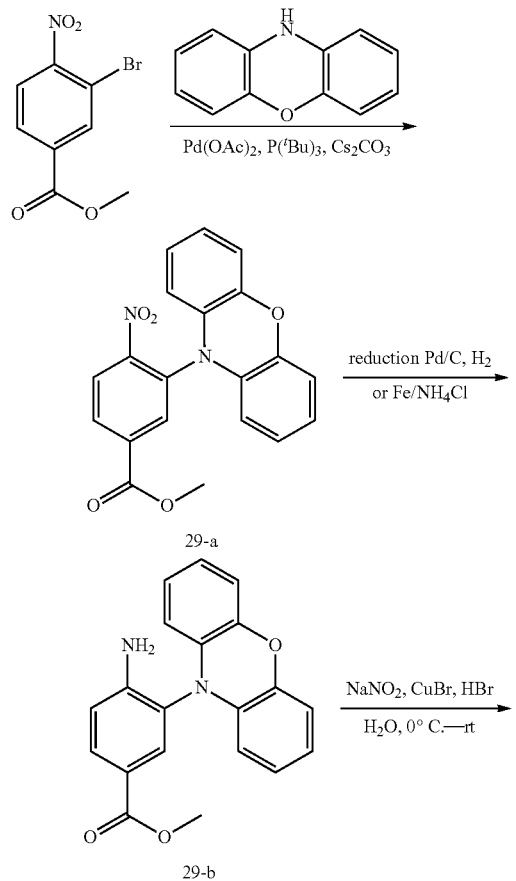

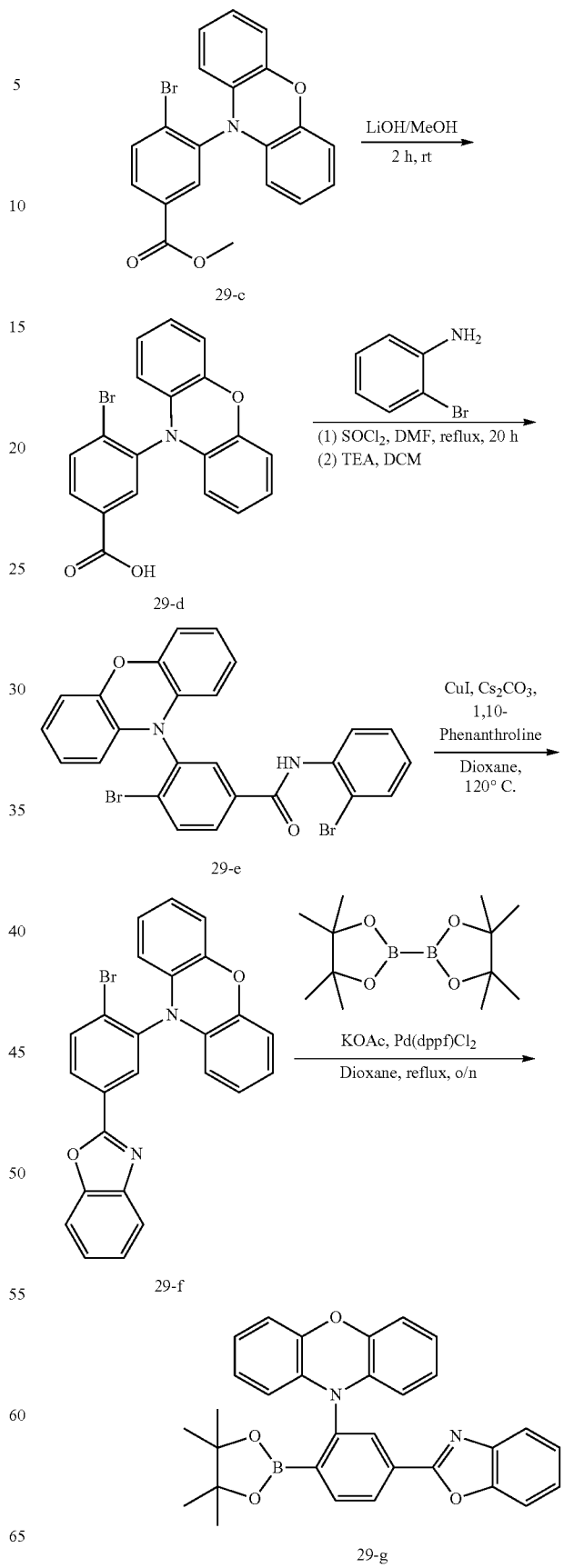

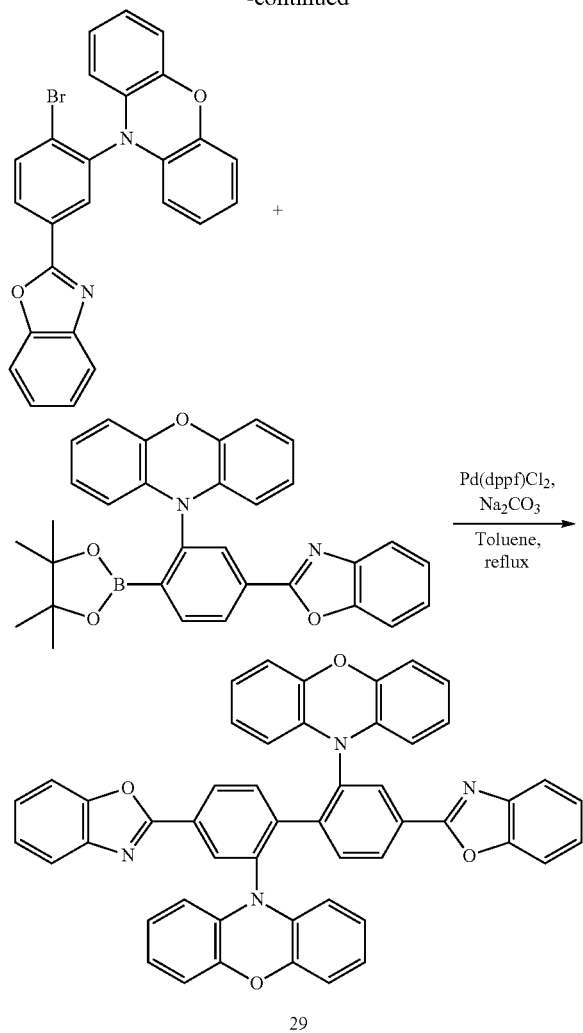

Step 1: Synthesis of Compound 29-a

Methyl 3-bromo-4-nitrobenzoate (20 g, 76.9 mmol), phenoxazine (14.1 g, 76.9 mmol), palladium acetate (0.8 g, 3.8 mmol), t-butyl phosphine (1.1 g, 5.8 mmol) and cesium carbonate (37.5 g, 115.4 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 29-a (15.6 g, yield of 56%).

Step 2: Synthesis of Compound 29-b

The above intermediate 29-a (15.6 g, 43.1 mmol) was dissolved in methanol, and 3 g Pd/C was added slowly under argon protection. The reaction was kept under a hydrogen atmosphere for 20 hours after the gas in the reaction vessel was replaced with hydrogen. After filtration and evaporation of the solvent, an intermediate 29-b (13.3 g, yield of 93%) was obtained.

Step 3: Synthesis of Compound 29-c

Sodium nitrite (7.5 g, 108.7 mmol) was dissolved in 10 mL of water, and the solution was slowly added dropwise into the mixture of the intermediate 29-b (12.0 g, 36.1 mmol) and 11 mL of 48% hydrobromic acid (approximately 91.0 mmol) under an ice bath (0° C.), and stirred for 1 hour. To the above mixture was added 10 mL of cuprous bromide (5.4 g, 37.9 mmol) solution in hydrobromic acid under an ice bath. The mixture was reacted for 1 hour under an ice bath, and then heated to 60° C. for 2 hours. After being cooled, the resulting mixture was extracted with 50 mL of ethyl acetate. The organic layer was washed with water for several times, dried over anhydrous magnesium sulfate and filtered. After evaporation of the solvent, an intermediate 29-c (10.3 g, yield of 72%) was obtained.

Step 4: Synthesis of Compound 29-d 29-c (10.3 g, 26.0 mmol) was dissolved in 30 mL of methanol, to this solution was added LiOH (3.1 g, 130.0 mmol), and stirred for 2 hours at room temperature. The methanol was evaporated, and the resulting mixture was extracted with 50 mL of ethyl acetate and 20 mL of water. The organic phase was washed with water for several times, dried over anhydrous magnesium sulfate and filtered. After evaporation of the solvent, an intermediate 29-d (8.4 g, yield of 85%) was obtained.

Step 5: Synthesis of Compound 29-e

The intermediate 29-d (8.4 g, 22.1 mmol) was dissolved in 100 mL of thionyl chloride. A few drops of DMF was added dropwise as catalyst, and heated to reflux for 20 hours. After the residual thionyl chloride was evaporated off in vacuo, the resulting mixture was dissolved in 300 mL of dichloromethane. 2-bromoaniline (7.6 g, 44.2 mmol) was added when being cooled in an ice bath, and 15 mL of triethylamine was slowly added dropwise. After completion of the addition, the mixture was stirred overnight at room temperature. The reaction suspension was filtered, and washed with dichloromethane twice to give the intermediate 29-e (10.6 g, yield of 73%).

Step 6: Synthesis of Compound 29-f

The above Compound 29-e (8.7 g, 16.1 mmol), cuprous iodide (0.3 g, 1.7 mmol), cesium carbonate (10.5 g, 32.2 mmol), and 1,10-phenanthroline (0.7 g, 3.3 mmol) were dissolved in 200 mL of dioxane under an argon stream protection, and reacted overnight at a constant temperature of 120° C. The resulting mixture was diluted with 300 mL of ethyl acetate and 500 mL of water after being cooled to room temperature. The suspension was filtered and washed with water and ethanol to give the intermediate 29-f (5.7 g, yield of 78%).

Step 7: Synthesis of Compound 29-g

Palladium catalyst Pd(dppf)Cl$_2$ (0.2 g, 0.3 mmol), potassium acetate (0.3 g, 3.0 mmol), bis(pinacolato)diboron (2.3 g, 8.9 mmol) were mixed into a reaction flask under a nitrogen stream. The intermediate 29-f (2.5 g, 5.5 mmol) solution dissolved in 150 mL of dioxane was added to the reaction flask and refluxed for 10 hours. After being cooled, the resulting mixture was extracted with toluene, washed with water for several times, and dried over anhydrous magnesium sulfate. After filtration and evaporation of the solvent, purification was carried out by silica gel chromatography column to give the intermediate 29-g (1.4 g, yield of 49%).

Step 8: Synthesis of Compound 29

The intermediate 29-g (1.4 g, 2.7 mmol), intermediate 29-f (1.2 g, 2.7 mmol), Pd(dppf)Cl$_2$ (0.04 g, 0.05 mmol), and 10 mL of 2M Na$_2$CO$_3$ aqueous solution were mixed into 100 mL of toluene under an argon stream, and heated to reflux for 10 hours. The resulting mixture was extracted with dichloromethane after being cooled. The organic phase was washed with water for several times, dried over anhydrous magnesium sulfate and filtered. After evaporation, purification was carried out by silica gel chromatography column to give a solid Compound 29 (0.7 g, yield of 33%).

ESI-MS(m/z) was obtained by Liquid Chromatograph-Mass Spectrometer analysis: 751.2[M+H]$^+$.

Example 17: Synthesis of Compound 30

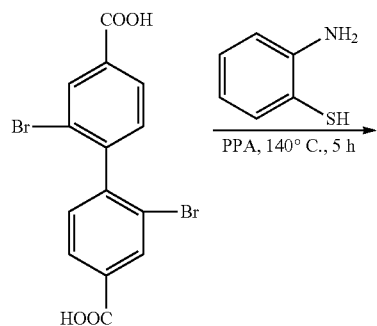

100.0 ml of deionized water was slowly added for full hydrolyzation. After filtration, the filter residue was fully dissolved with dichloromethane and filtered. Then the filtrate was pumped to remove the solvent under vacuum and purified using silica gel chromatography column to give the intermediate 30-a (12.7 g, yield of 44%).

Step 2: Synthesis of Compound 30

The above intermediate 30-a (12.7 g, 22.0 mmol), phenoxazine (8.1 g, 44.0 mmol), palladium acetate (0.5 g, 2.2 mmol), t-butyl phosphine (0.7 g, 3.3 mmol) and cesium carbonate (21.5 g, 66.0 mmol) were dissolved in toluene, and heated to reflux for 10 hours under a nitrogen atmosphere. The solvent was evaporated off in vacuo. To the residue was added pentane and stirred. The resulting mixture

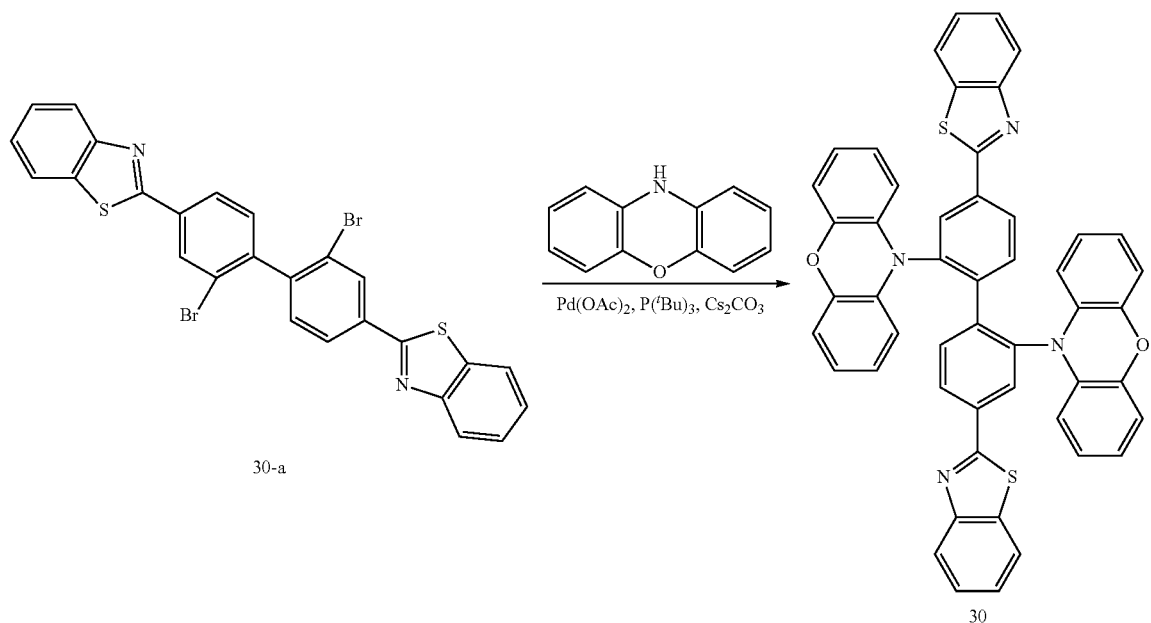

2,2'-dibromo-4,4'-dicarboxybiphenyl (20 g, 50.0 mmol), 2-aminothiophnol (12.5 g, 100.0 mmol) and 100.0 g of polyphosphoric acid (PPA) were heated at 140° C. for 5 h with stirring, and then naturally cooled to room temperature.

was filtered and purified by silica gel chromatography column to give a solid Compound 30 (4.8 g, yield of 28%). ESI-MS (m/z) was obtained by Liquid Chromatograph-Mass Spectrometer analysis: 783.1[M+H]$^+$.

Example 18: Synthesis of Compound 55

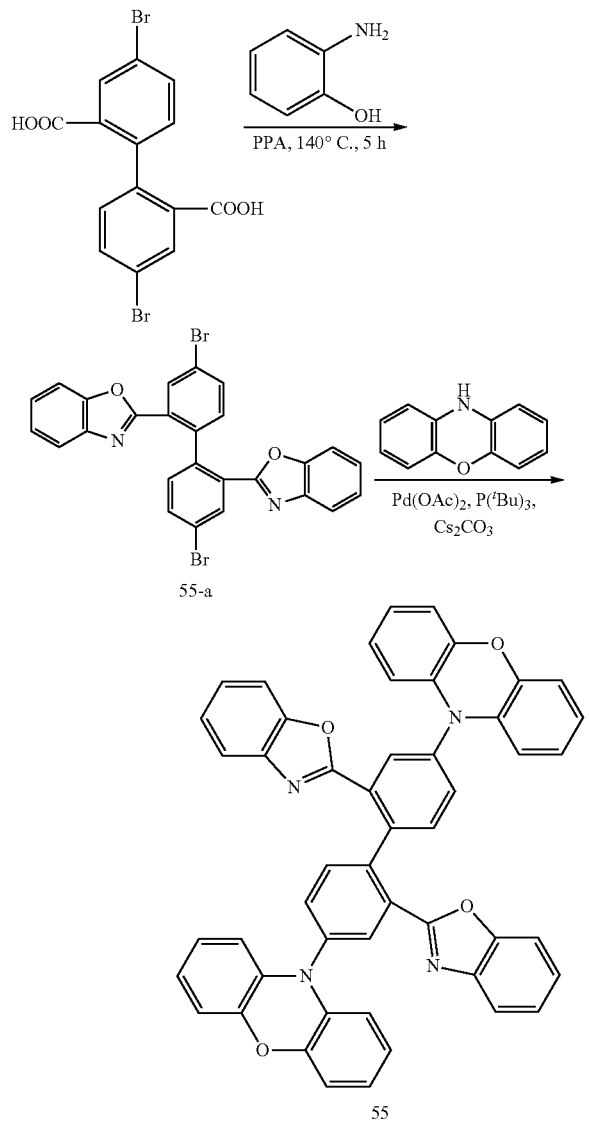

Step 1: Synthesis of Compound 55-a

A mixture of 2,2'-dicarboxy-4,4'-dibromobiphenyl (20 g, 50.0 mmol), 2-hydroxyaniline (10.9 g, 100.0 mmol) and 100.0 g of polyphosphoric acid (PPA) was heated at 140° C. for 5 h with stirring, and then naturally cooled to room temperature. 100.0 mL of deionized water was slowly added for full hydrolyzation. After filtration, the filter residue was fully dissolved with dichloromethane and filtered. Then the filtrate was pumped to remove the solvent under vacuum and purified using silica gel chromatography column to give the intermediate 55-a (6.8 g, yield of 25%).

Step 2: Synthesis of Compound 55

The above intermediate 55-a (6.8 g, 12.5 mmol), phenoxazine (4.6 g, 25.0 mmol), palladium acetate (0.3 g, 1.3 mmol), t-butyl phosphine (0.4 g, 1.9 mmol) and cesium carbonate (12.2 g, 37.5 mmol) were dissolved in toluene, and heated to reflux for 10 hours under a nitrogen atmosphere. The solvent was evaporated off in vacuo. To the residue was added pentane and stirred. The resulting mixture was filtered and purified by silica gel chromatography column to give a solid Compound 55 (2.9 g, yield of 31%). ESI-MS (m/z) was obtained by Liquid Chromatograph-Mass Spectrometer analysis: 751.2[M+H]$^+$.

Example 19: Synthesis of Compound 40

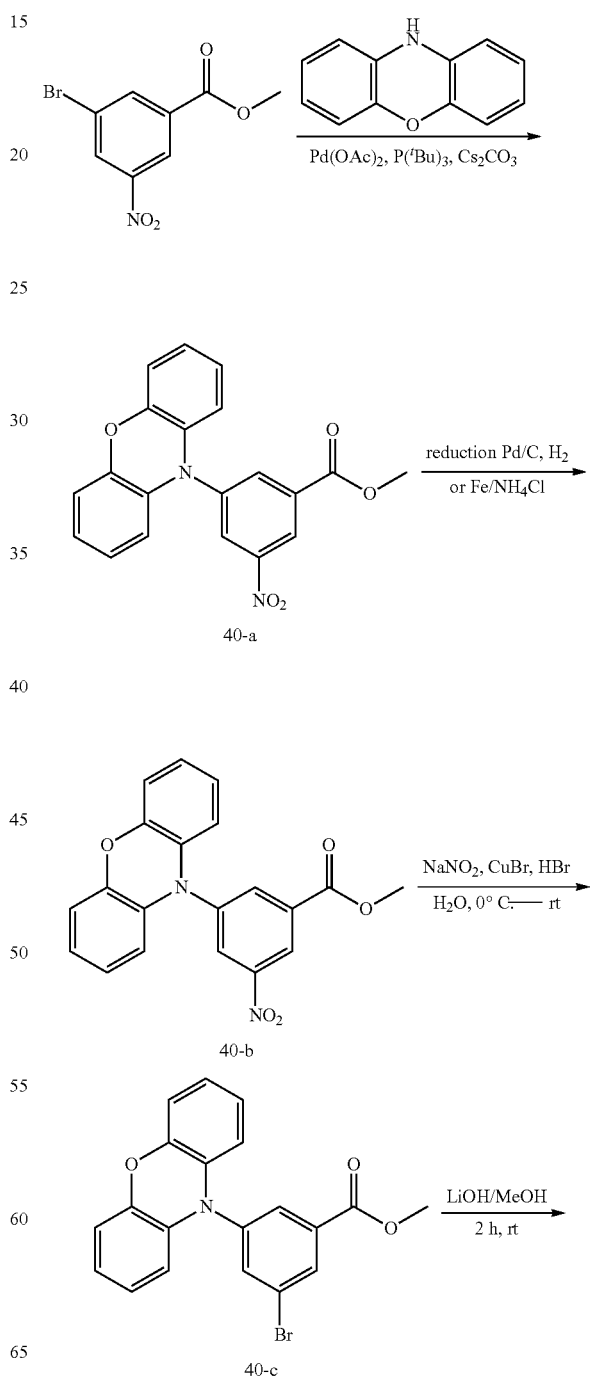

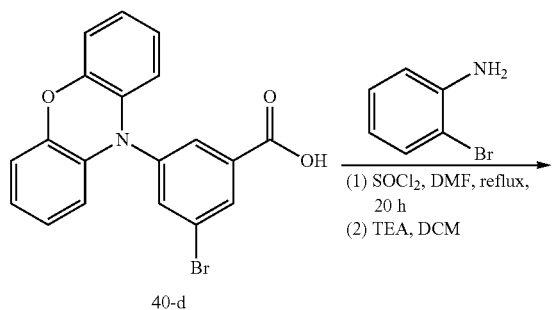

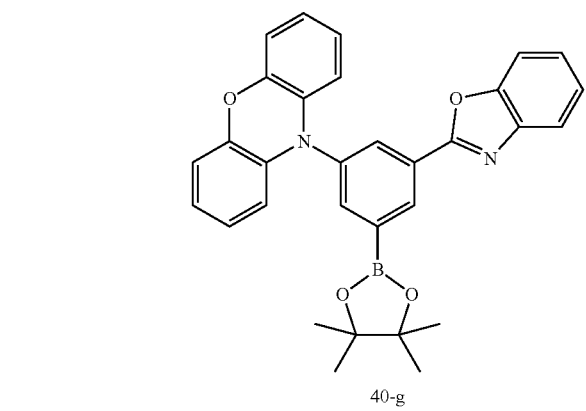

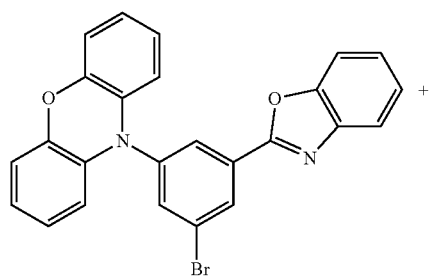

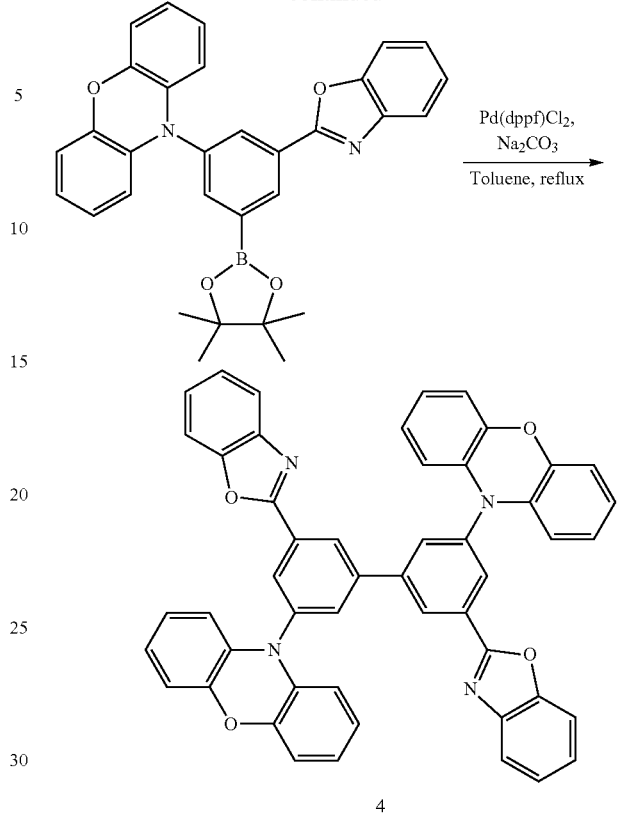

Step 1: Synthesis of Compound 40-a 3-bromo-5-nitrobenzoate (20 g, 76.9 mmol), phenoxazine (14.1 g, 76.9 mmol), palladium acetate (0.8 g, 3.8 mmol), t-butyl phosphine (1.1 g, 5.8 mmol) and cesium carbonate (37.5 g, 115.4 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 40-a (14.5 g, yield of 52%).

Step 2: Synthesis of Compound 40-b

The above intermediate 40-a (14.5 g, 40.0 mmol) was dissolved in methanol, and 3 g Pd/C was added slowly under argon protection. The reaction was kept under a hydrogen atmosphere for 20 hours after the gas in the reaction vessel was replaced with hydrogen. After filtration and evaporation of the solvent, an intermediate 40-b (12.0 g, yield of 90%) was obtained.

Step 3: Synthesis of Compound 40-c

Sodium nitrite (7.5 g, 108.7 mmol) was dissolved in 10 mL of water, and this solution was slowly added dropwise into the mixture of the intermediate 40-b (12.0 g, 36.1 mmol) and 11 mL of 48% hydrobromic acid (approximately 91.0 mmol) under an ice bath (0° C.), and stirred for 1 hour. To the above mixture was added 10 mL of cuprous bromide (5.4 g, 37.9 mmol) solution in hydrobromic acid under an ice bath. The mixture was reacted for 1 hour under an ice bath, and then heated to 60° C. for 2 hours. After being cooled, the resulting mixture was extracted with 50 mL of ethyl acetate. The organic layer was washed with water for several times, dried over anhydrous magnesium sulfate and filtered. After evaporation of the solvent, an intermediate 40-c (11.3 g, yield of 79%) was obtained.

Step 4: Synthesis of Compound 40-d

The intermediate 40-c (11.3 g, 28.5 mmol) was dissolved in 30 mL of methanol, to this solution was added LiOH (3.4 g, 142.5 mmol), and stirred for 2 hours at room temperature. The methanol was evaporated, and the resulting mixture was extracted with 50 mL of ethyl acetate and 20 mL of water. The organic phase was washed with water for several times, dried over anhydrous magnesium sulfate and filtered. After evaporation of the solvent, an intermediate 40-d (9.7 g, yield of 89%) was obtained.

Step 5: Synthesis of Compound 40-e

The intermediate 40-d (9.7 g, 25.4 mmol) was dissolved in 100 mL of thionyl chloride. A few drops of DMF was added dropwise as catalyst, and heated to reflux for 20 hours. After the residual thionyl chloride was evaporated off in vacuo, the resulting mixture was dissolved in 300 mL of dichloromethane. 2-bromoaniline (8.7 g, 50.8 mmol) was added when being cooled in an ice bath, and 15 mL of triethylamine was slowly added dropwise. After completion of the addition, the mixture was stirred overnight at room temperature. The reaction suspension was filtered, and washed with dichloromethane twice to give the intermediate 40-e (10.6 g, yield of 78%).

Step 6: Synthesis of Compound 40-f

The above Compound 40-e (10.6 g, 19.8 mmol), cuprous iodide (0.4 g, 2.1 mmol), cesium carbonate (12.9 g, 39.6 mmol), and 1,10-phenanthroline (0.8 g, 4.0 mmol) were dissolved in 200 mL of dioxane under an argon stream protection, and reacted overnight at a constant temperature of 120° C. The resulting mixture was diluted with 300 mL of ethyl acetate and 500 mL of water after being cooled to room temperature. The suspension was filtered and washed with water and ethanol to give the intermediate 40-f (7.5 g, yield of 83%).

Step 7: Synthesis of Compound 40-g

Catalyst Pd(dppf)Cl$_2$ (0.2 g, 0.3 mmol), potassium acetate (0.3 g, 3.0 mmol), bis(pinacolato)diboron (2.3 g, 8.9 mmol) were mixed into a reaction flask under a nitrogen stream. The intermediate 40-f (3.7 g, 8.1 mmol) solution dissolved in 150 mL of dioxane was added to the reaction flask and refluxed for 10 hours. After being cooled, the resulting mixture was extracted with toluene, washed with water for several times, and dried over anhydrous magnesium sulfate. After filtration and evaporation of the solvent, purification was carried out by silica gel chromatography column to give the intermediate 40-g (2.2 g, yield of 53%).

Step 8: Synthesis of Compound 40

The intermediate 40-g (2.2 g, 4.3 mmol), intermediate 40-f (2.0 g, 4.3 mmol), Pd(dppf)Cl$_2$ (0.06 g, 0.09 mmol), and 20 mL of 2M Na$_2$CO$_3$ aqueous solution were mixed into 100 mL of toluene under an argon stream, and heated to reflux for 10 hours. The resulting mixture was extracted with dichloromethane after being cooled. The organic phase was washed with water for several times, dried over anhydrous magnesium sulfate and filtered. After evaporation, purification was carried out by silica gel chromatography column to give a solid Compound 40 (1.2 g, yield of 36%). ESI-MS (m/z) was obtained by Liquid Chromatograph-Mass Spectrometer analysis: 751.1[M+H]$^+$.

Example 20: Synthesis of Compound 1

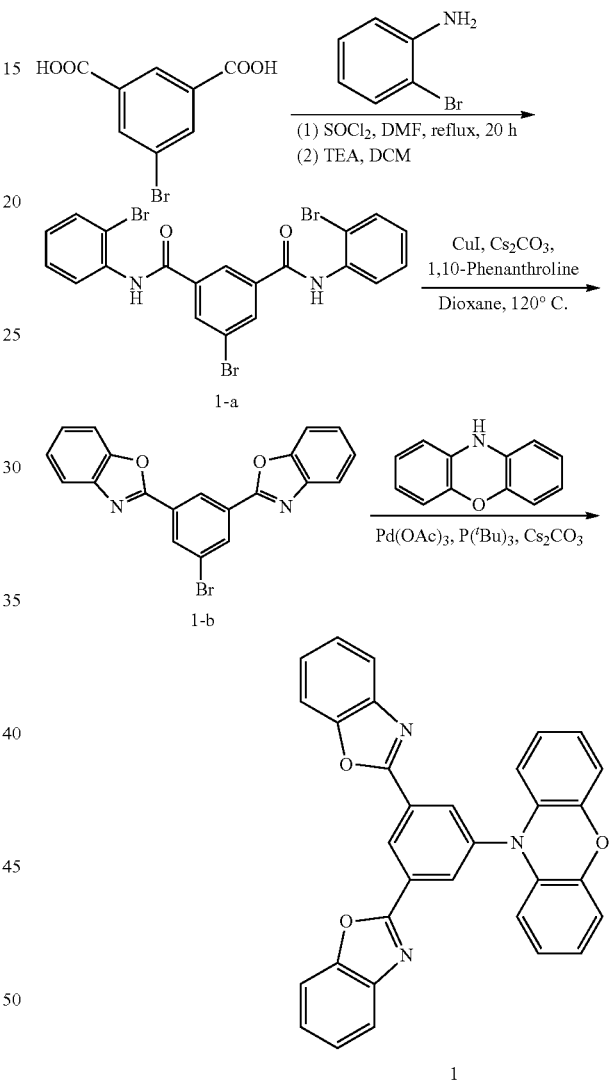

Step 1: Synthesis of Compound 1-a 5-bromoisophthalic acid (20 g, 81.6 mmol) was dissolved in 100 mL of thionyl chloride. A few drops of DMF was added dropwise as catalyst, and heated to reflux for 20 hours. After the residual thionyl chloride was evaporated off in vacuo, the resulting mixture was dissolved in 300 mL of dichloromethane. After cooling in an ice bath, 2-bromoaniline (28.1 g, 163.2 mmol) was added, and 30 mL of triethylamine was slowly added dropwise. The mixture was stirred overnight at room temperature after the addition. The reaction suspension was filtered, and washed with dichloromethane twice to give the intermediate 1-a (38.4 g, yield of 85%).

Step 2: Synthesis of Compound 1-b

The above Compound 1-a (38.4 g, 69.4 mmol), cuprous iodide (1.3 g, 6.9 mmol), cesium carbonate (45.2 g, 138.7 mmol), and 1,10-phenanthroline (2.5 g, 13.9 mmol) were dissolved in 300 mL of dioxane under an argon stream protection, and reacted overnight at a constant temperature of 120° C. The resulting mixture was diluted with 500 mL of ethyl acetate and 700 mL of water after being cooled to room temperature. The suspension was filtered and washed with water and ethanol to give a white solid intermediate 1-b (19.8 g, yield of 73%).

Step 3: Synthesis of Compound 1

The above intermediate 1-b (19.8 g, 50.6 mmol), phenoxazine (9.3 g, 50.6 mmol), palladium acetate (0.6 g, 2.7 mmol), t-butyl phosphine (0.8 g, 3.8 mmol) and cesium carbonate (24.7 g, 75.9 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 1 (8.1 g, yield of 31%).

ESI-MS (m/z) was obtained by Liquid Chromatograph-Mass Spectrometer analysis: 494.1[M+H]$^+$.

Example 21: Synthesis of Compound 70

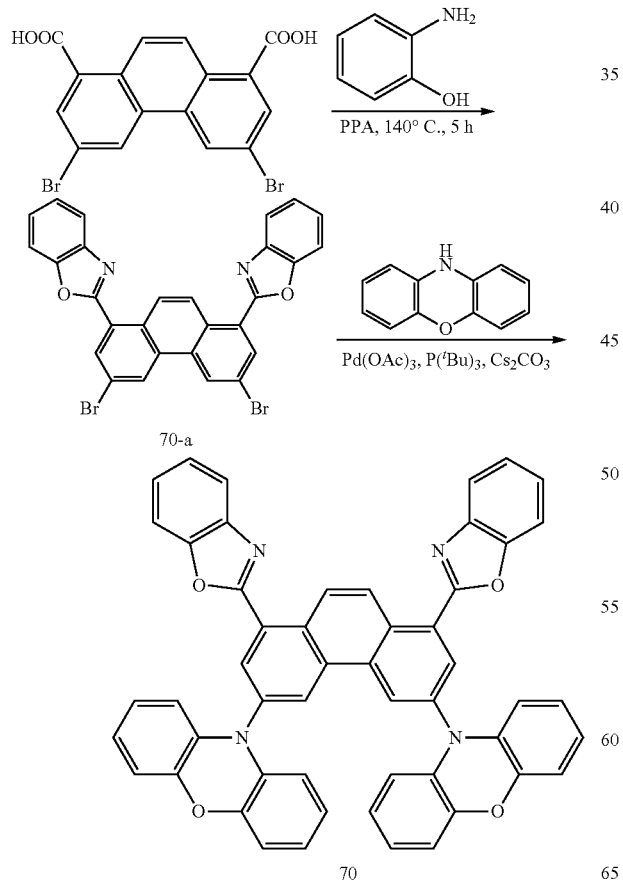

Step 1: Synthesis of Compound 70-a 2,9-dibromophenanthrene-4,7-dicarboxylic acid (20 g, 47.2 mmol), 2-hydroxyaniline (10.4 g, 94.4 mmol) and 100.0 g of polyphosphoric acid (PPA) were heated at 140° C. for 5 h with stirring, and then naturally cooled to room temperature. 100.0 mL of deionized water was slowly added for full hydrolyzation. After filtration, a gray-green filter residue was obtained. The filter residue was fully dissolved with dichloromethane and filtered to obtain an orange-red clear filtrate. Then the solvent was pumped away under vacuum, and purification was carried out using silica gel chromatography column to give the intermediate 70-a (19.4 g, yield of 72%).

Step 2: Synthesis of Compound 70

The above intermediate 70-a (19.4 g, 34.0 mmol), phenoxazine (12.5 g, 68.0 mmol), palladium acetate (0.4 g, 1.8 mmol), t-butyl phosphine (0.5 g, 2.5 mmol) and cesium carbonate (16.6 g, 51.0 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 70 (9.9 g, yield of 39%). ESI-MS (m/z) was obtained by Liquid Chromatograph-Mass Spectrometer analysis: 775.1[M+H]$^+$.

Example 22: Synthesis of Compound 33

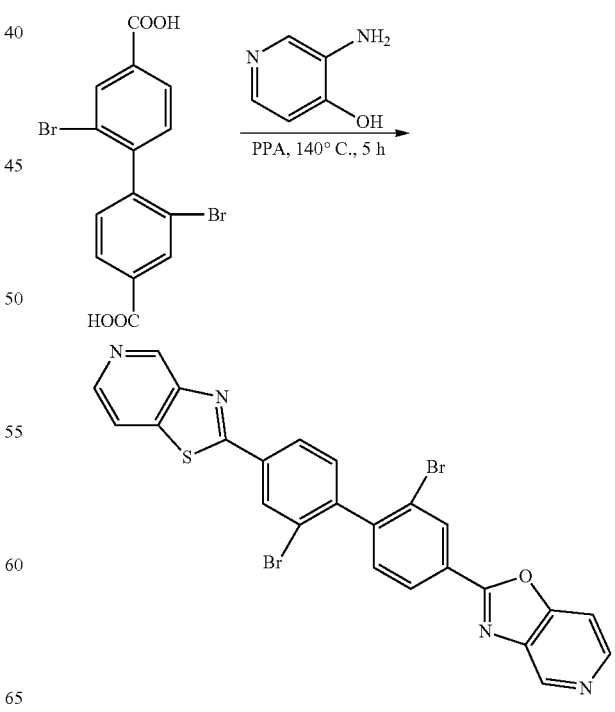

-continued

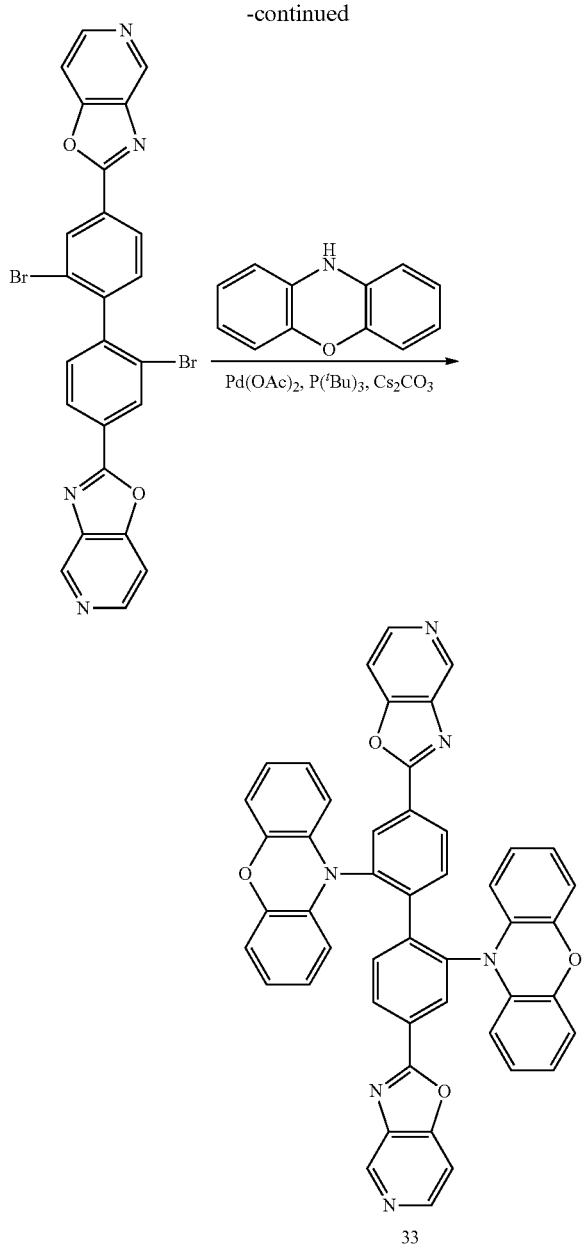

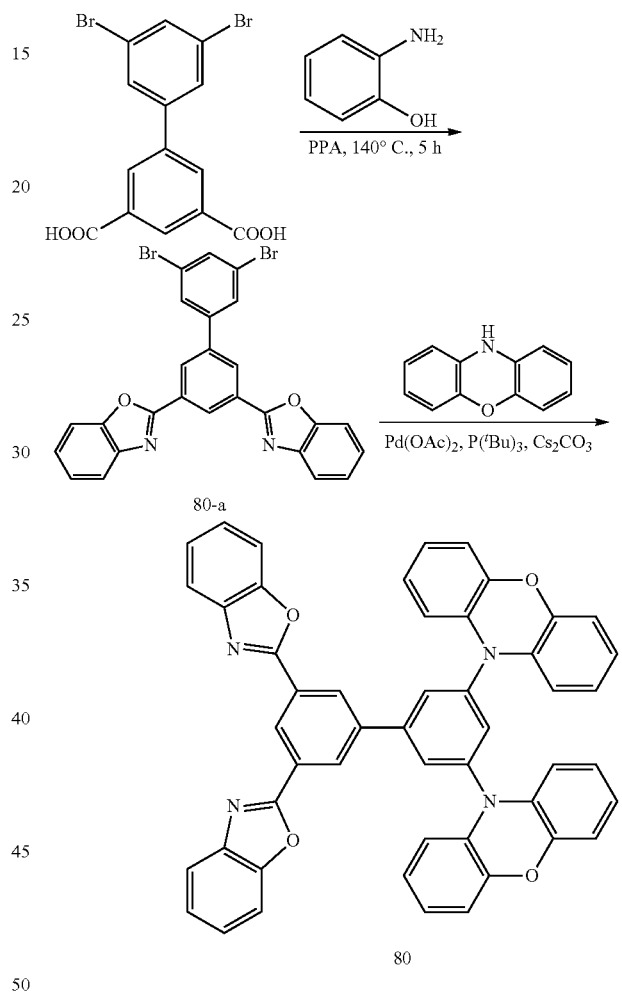

mmol), t-butyl phosphine (0.5 g, 2.5 mmol) and cesium carbonate (16.9 g, 51.9 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 33 (8.8 g, yield of 34%). ESI-MS (m/z) was obtained by Liquid Chromatograph-Mass Spectrometer analysis: 753.1[M+H]$^+$.

Example 23: Synthesis of Compound 80

Step 1: Synthesis of Compound 33-a 2,2'-dibromo-4,4'-dicarboxybiphenyl (20 g, 50.0 mmol), 3-amino-4-hydroxypyridine (11.0 g, 100.0 mmol) and 100.0 g of polyphosphoric acid (PPA) were heated at 140° C. for 5 h with stirring, and then naturally cooled to room temperature. 100.0 mL of deionized water was slowly added for full hydrolyzation. After filtration, the filter residue was fully dissolved with dichloromethane and filtered. Then the filtrate was pumped to remove the solvent under vacuum and purified using silica gel chromatography column to give the intermediate 33-a (18.9 g, yield of 69%).

Step 2: Synthesis of Compound 33

The above intermediate 33-a (18.9 g, 34.5 mmol), phenoxazine (12.6 g, 69.0 mmol), palladium acetate (0.4 g, 1.8

Step 1: Synthesis of Compound 80-a 3,5-dibromo-3',5'-dicarboxybiphenyl (20 g, 50.0 mmol), 2-hydroxyaniline (10.9 g, 100.0 mmol) and 100.0 g of polyphosphoric acid (PPA) were heated at 140° C. for 5 h with stirring, and then naturally cooled to room temperature. 100.0 mL of deionized water was slowly added for full hydrolyzation. After filtration, the filter residue was fully dissolved with dichloromethane and filtered. Then the filtrate was pumped to remove the solvent under vacuum and purified using silica gel chromatography column to give the intermediate 80-a (10.4 g, yield of 38%).

Step 2: Synthesis of Compound 80

The above intermediate 80-a (10.4 g, 19.0 mmol), phenoxazine (7.0 g, 38.0 mmol), palladium acetate (0.4 g, 1.9 mmol), t-butyl phosphine (0.6 g, 2.9 mmol) and cesium carbonate (18.6 g, 57.0 mmol) were dissolved in toluene, and heated to reflux for 10 hours under a nitrogen atmosphere. The solvent was evaporated off in vacuo. To the residue was added pentane and stirred. The resulting mixture was filtered and purified by silica gel chromatography column to give a solid Compound 80 (3.3 g, yield of 23%).

ESI-MS (m/z) was obtained by Liquid Chromatograph-Mass Spectrometer analysis: 751.1[M+H]$^+$.

Example 24: Synthesis of Compound 84

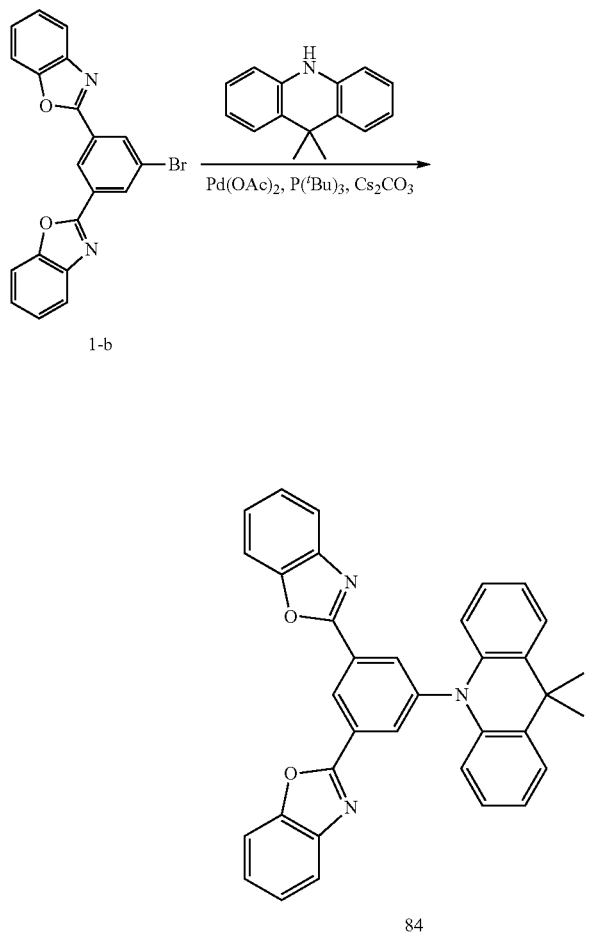

Step 1: Synthesis of Compound 84

The intermediate 1-b (5.0 g, 12.8 mmol), 9,9-dimethyl-acridan (5.4 g, 25.6 mmol), palladium acetate (0.3 g, 1.3 mmol), t-butyl phosphine (0.4 g, 1.9 mmol) and cesium carbonate (12.5 g, 38.4 mmol) were dissolved in toluene, and heated to reflux for 8 hours under a nitrogen atmosphere. The solvent was evaporated off in vacuo. To the residue was added pentane and stirred. The resulting mixture was filtered and purified by silica gel chromatography column to give a solid Compound 84 (1.9 g, yield of 28%). ESI-MS (m/z) was obtained by Liquid Chromatograph-Mass Spectrometer analysis: 520.1[M+H]$^+$.

Example 25: Synthesis of Compound 91

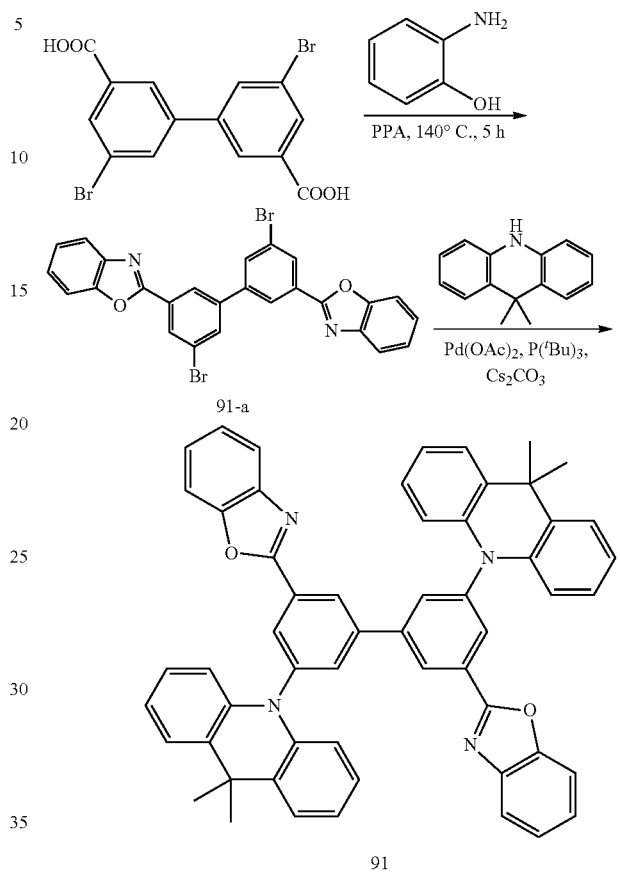

Step 1: Synthesis of Compound 91-a 3,3'-dicarboxy-5,5'-dibromobiphenyl (20 g, 50.0 mmol), 2-hydroxyaniline (10.9 g, 100.0 mmol) and 100.0 g of polyphosphoric acid (PPA) were heated at 140° C. for 5 h with stirring, and then naturally cooled to room temperature. 100.0 mL of deionized water was slowly added for full hydrolyzation. After filtration, the filter residue was fully dissolved with dichloromethane and filtered. Then the filtrate was pumped to remove the solvent under vacuum, and purified using silica gel chromatography column to give the intermediate 91-a (10.1 g, yield of 37%).

Step 2: Synthesis of Compound 91

The above intermediate 91-a (10.1 g, 18.5 mmol), 9,9-dimethylacridan (7.7 g, 37.0 mmol), palladium acetate (0.4 g, 1.9 mmol), t-butyl phosphine (0.6 g, 2.8 mmol) and cesium carbonate (18.1 g, 55.5 mmol) were dissolved in toluene, and heated to reflux for 10 hours under a nitrogen atmosphere. The solvent was evaporated off in vacuo. To the residue was added pentane and stirred. The resulting mixture was filtered and purified by silica gel chromatography column to give a solid Compound 91 (4.2 g, yield of 28%). ESI-MS (m/z) was obtained by Liquid Chromatograph-Mass Spectrometer analysis: 803.2[M+H]$^+$.

Example 26: Synthesis of Compound 103

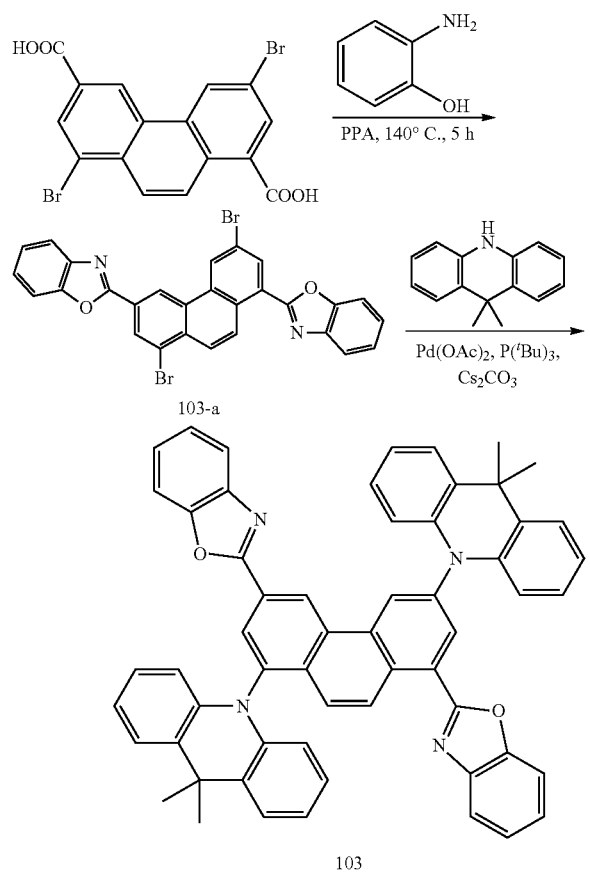

Step 1: Synthesis of Compound 103-a 4,9-dibromophenanthrene-2,7-dicarboxylic acid (20 g, 47.2 mmol), 2-hydroxyaniline (10.3 g, 94.4 mmol) and 100.0 g of polyphosphoric acid (PPA) were heated at 140° C. for 5 h with stirring, and then naturally cooled to room temperature. 100.0 mL of deionized water was slowly added for full hydrolyzation. After filtration, the filter residue was fully dissolved with dichloromethane and filtered. Then the filtrate was pumped to remove the solvent under vacuum and purified using silica gel chromatography column to give the intermediate 103-a (5.7 g, yield of 21%).

Step 2: Synthesis of Compound 103

The above intermediate 103-a (5.7 g, 9.9 mmol), 9,9-dimethylacridan (4.1 g, 19.8 mmol), palladium acetate (0.2 g, 1.0 mmol), t-butyl phosphine (0.3 g, 1.5 mmol) and cesium carbonate (9.7 g, 29.7 mmol) were dissolved in toluene, and heated to reflux for 10 hours under a nitrogen atmosphere. The solvent was evaporated off in vacuo. To the residue was added pentane and stirred. The resulting mixture was filtered and purified by silica gel chromatography column to give a solid Compound 103 (2.2 g, yield of 27%).

ESI-MS (m/z) was obtained by Liquid Chromatograph-Mass Spectrometer analysis: 827.3[M+H]$^+$.

Example 27: Synthesis of Compound 6

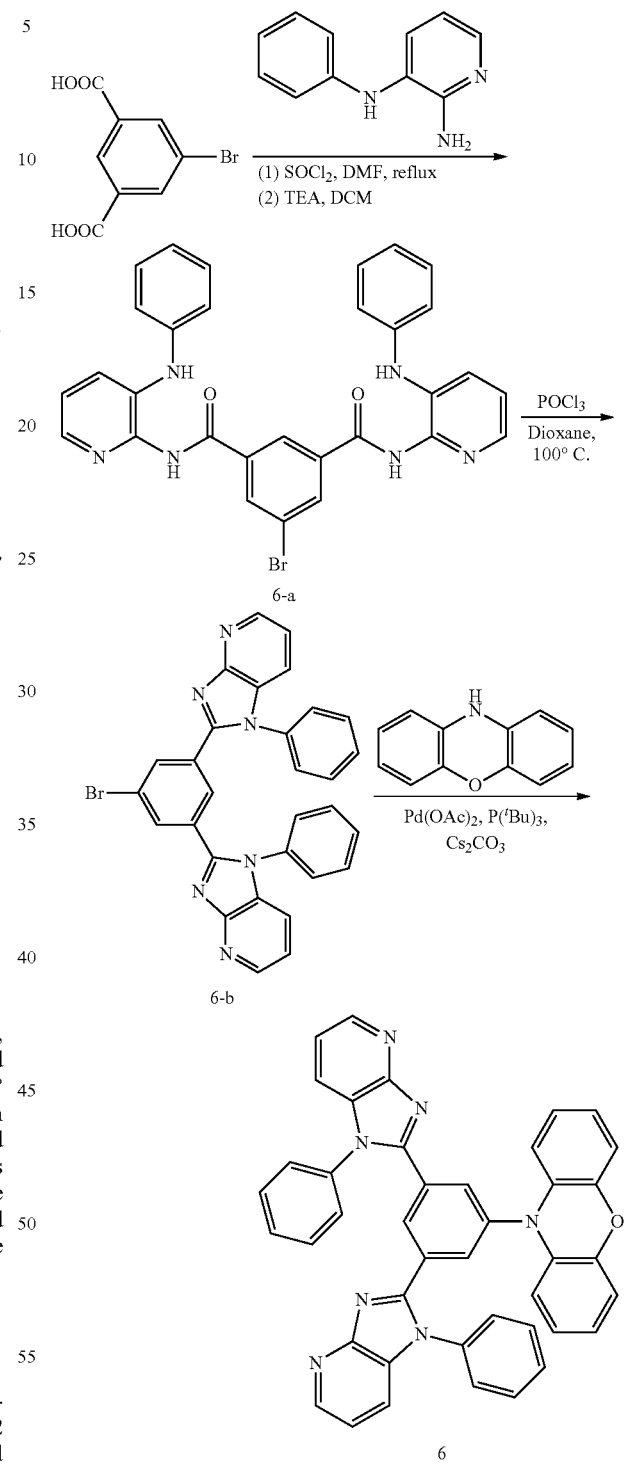

Step 1: Synthesis of a Intermediate 6-a 5-bromoisophthalic acid (10 g, 40.8 mmol) was dissolved in 50 mL of thionyl chloride. A few drops of DMF was added dropwise as catalyst, and heated to reflux overnight under an argon condition. After the residual thionyl chloride was evaporated off in vacuo, the resulting mixture was dissolved in 150 mL of dichloromethane. After being cooled in an ice bath, N'-3'-phenyl-2,3-diaminopyridine (15.1 g, 81.6 mmol) was added, and 15 mL of triethylamine was slowly added dropwise. After the addition, the mixture was stirred overnight at room temperature. The reaction suspension was filtered, and washed with dichloromethane twice to give the intermediate 6-a (19.6 g, yield of 83%).

Step 2: Synthesis of a Intermediate 6-b

POCl$_3$ (20.8 g, 135.6 mmol) was slowly added to the intermediate 6-a (19.6 g, 33.9 mmol) solution in dioxane when being cooled in a water bath. The mixture was heated to 100° C. and stirred overnight. Ice cubes were added after the mixture was cooled to room temperature, and the mixture was neutralized to be neutral with Na$_2$CO$_3$ solution. The resulting mixture was extracted twice with dichloromethane, and dried over anhydrous Na$_2$SO$_4$. The organic phase was concentrated, and then purified using silica gel chromatography column to give the intermediate 6-b (13.6 g, yield of 74%).

Step 3: Synthesis of Compound 6

The above intermediate 6-b (13.6 g, 25.1 mmol), phenoxazine (5.1 g, 27.6 mmol), palladium acetate (0.3 g, 1.3 mmol), t-butyl phosphine (0.4 g, 1.9 mmol) and cesium carbonate (12.3 g, 37.7 mmol) were dissolved in toluene, and heated to reflux for 8 hours under an argon atmosphere. The solvent was evaporated off in vacuo. To the residue was added pentane and stirred. The resulting mixture was filtered and purified by silica gel chromatography column to give a solid Compound 6 (6.0 g, yield of 37%). ESI-MS (m/z) was obtained by Liquid Chromatograph-Mass Spectrometer analysis: 646.1[M+H]$^+$.

Example 28: Synthesis of Compound 12

Except that 3-amino-4-hydroxypyridine was replaced with 3-aminopyridine-2-thiol and 2,2'-dibromo-4,4'-dicarboxybiphenyl was replaced with 5-bromoisophthalic acid, the other synthetic procedures are the same as those in Example 22. Purification was carried out by silica gel chromatography column to give a solid Compound 12 (9.0 g, yield of 21%).
ESI-MS (m/z) was obtained by Liquid Chromatograph-Mass Spectrometer analysis: 528.1[M+H]$^+$.

Example 29: Synthesis of Compound 17

Except that 5-bromoisophthalic acid was replaced with 3,5-dibromobenzoic acid and N'-3'-phenyl-2,3-diaminopyridine was replaced with N'-2'-phenyl-2,3-diaminopyridine, the other synthetic procedures are the same as those in Example 27. Purification was carried out by silica gel chromatography column to give a solid Compound 17 (5.4 g, yield of 24%).
ESI-MS (m/z) was obtained by Liquid Chromatograph-Mass Spectrometer analysis: 634.2[M+H]$^+$.

Example 30: Synthesis of Compound 24

Except that 3-aminopyridine-2-thiol was replaced with 2-amino-3-hydroxypyridine and 5-bromoisophthalic acid was replaced with 3,5-dibromobenzoic acid, the other synthetic procedures are the same as those in Example 22. Purification was carried out by silica gel chromatography column to give a solid Compound 24 (7.6 g, yield of 19%).
ESI-MS (m/z) was obtained by Liquid Chromatograph-Mass Spectrometer analysis: 559.1[M+H]$^+$.

Example 31: Synthesis of Compound 51

Except that 5-bromoisophthalic acid was replaced with 3,3'-dibromo-5,5'-dicarboxybiphenyl and N'-3'-phenyl-2,3-diaminopyridine was replaced with N'-2'-phenyl-2,3-diaminopyridine, the other synthetic procedures are the same as those in Example 27. Purification was carried out by silica gel chromatography column to give a solid Compound 51 (3.8 g, yield of 17%).
ESI-MS (m/z) was obtained by Liquid Chromatograph-Mass Spectrometer analysis: 903.2[M+H]$^+$.

Example 32: Synthesis of Compound 76

Except that 2,9-dibromophenanthrene-4,7-dicarboxylic acid was replaced with 4,7-dibromophenanthrene-2,9-dicarboxylic acid and 2-hydroxyaniline was replaced with 2-amino-3-hydroxypyridine, the other synthetic procedures are the same as those in Example 21. Purification was carried out by silica gel chromatography column to give a solid Compound 76 (8.8 g, yield of 24%).
ESI-MS (m/z) was obtained by Liquid Chromatograph-Mass Spectrometer analysis: 777.2[M+H]$^+$.

Example 33: Synthesis of Compound 128

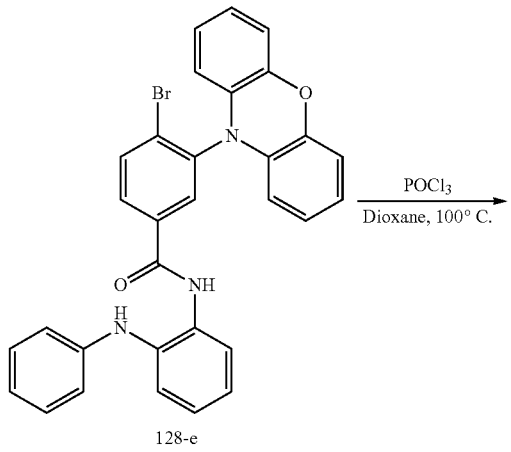

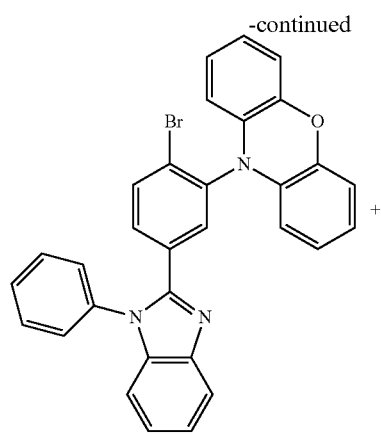

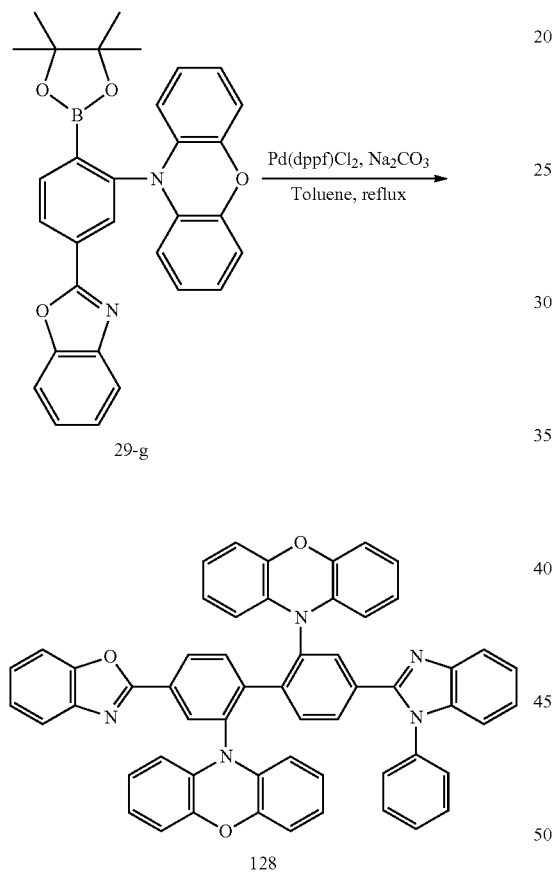
29-g

128 to 100° C. and stirred overnight. Ice cubes were added after the mixture was cooled to room temperature, and the mixture was neutralized to be neutral with $Na_2CO_3$ solution. The resulting mixture was extracted twice with dichloromethane, and dried over anhydrous magnesium sulfate. The organic phase was concentrated, and then purified using silica gel chromatography column to give the intermediate 128-f (7.4 g, yield of 79%).

Step 3: Synthesis of Compound 128

The intermediate 29-g (7.0 g, 14.0 mmol), intermediate 128-f (7.4 g, 14.0 mmol), Pd(dppf)Cl$_2$ (0.2 g, 0.3 mmol), and 50 mL of 2M $Na_2CO_3$ aqueous solution were mixed into 200 mL of toluene under an argon stream, and heated to reflux for 10 hours. The resulting mixture was extracted with dichloromethane after being cooled. The organic phase was washed with water for several times, dried over anhydrous magnesium sulfate and filtered. After evaporation, purification was carried out by silica gel column chromatography to give a solid Compound 128 (3.0 g, yield of 26%). ESI-MS (m/z) was obtained by Liquid Chromatograph-Mass Spectrometer analysis: 826.2[M+H]$^+$.

Example 34: Synthesis of Compound 138

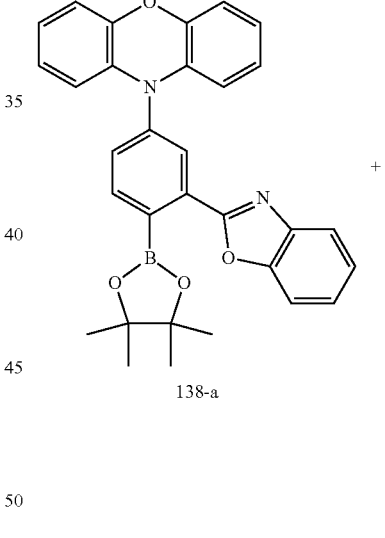
138-a

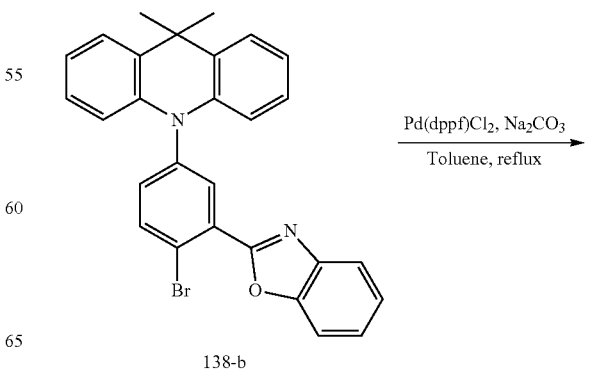
138-b

Step 1: Synthesis of a Intermediate 128-e

Except that 2-hydroxyaniline was replaced with N-phenylbenzene-1,2-diamine, the other synthetic procedures are the same as those of the intermediate 29-e in Example 16. A solid intermediate 128-e (9.7 g, yield of 23%) was obtained after purification.

Step 2: Synthesis of a Intermediate 128-f

POCl$_3$ (5.4 g, 35.4 mmol) was slowly added to the intermediate 128-e (9.7 g, 17.7 mmol) solution in dioxane when being cooled in a water bath. The mixture was heated -continued

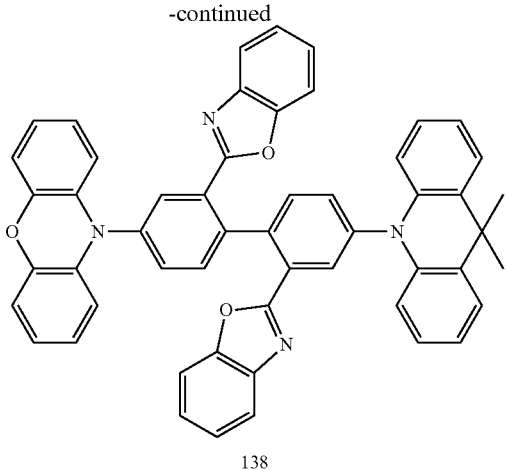

138

Step 1: Synthesis of a Intermediate 138-a

Methyl 3-bromo-4-nitrobenzoate was replaced with methyl 2-nitro-5-bromobenzoate, the other synthetic procedures are the same as those of the intermediate 29-g in Example 16. Purification was carried out by silica gel chromatography column to give a solid intermediate 138-a (3.1 g, yield of 8%).

Step 2: Synthesis of a Intermediate 138-b

Methyl 3-bromo-4-nitrobenzoate was replaced with methyl 2-nitro-5-bromobenzoate, and phenoxazine was replaced with 9,9-dimethylacridan, the other synthetic procedures are the same as those of the intermediate 29-f in Example 16. Purification was carried out by silica gel chromatography column to give a solid intermediate 138-b (5.9 g, yield of 16%).

Step 3: Synthesis of Compound 138

The intermediate 138-a (3.1 g, 6.1 mmol), intermediate 138-b (2.9 g, 6.1 mmol), Pd(dppf)Cl$_2$ (0.08 g, 0.11 mmol), and 25 mL of 2M Na$_2$CO$_3$ aqueous solution were mixed into 150 mL of toluene under an argon stream, and heated to reflux for 10 hours. The resulting mixture was extracted with dichloromethane after being cooled. The organic phase was washed with water for several times, dried over anhydrous magnesium sulfate and filtered. After evaporation, purification was carried out by silica gel column chromatography to give a solid Compound 138 (1.3 g, yield of 27%). ESI-MS (m/z) was obtained by Liquid Chromatograph-Mass Spectrometer analysis: 777.1[M+H]$^+$.

Example 35: Synthesis of Compound 162

Except that 2,9-dibromophenanthrene-4,7-dicarboxylic acid was replaced with 1,5-dinitro-3,7-dibromonaphthalene, the other synthetic procedures are the same as those of Example 21. Purification was carried out by silica gel chromatography column to give a solid Compound 162 (6.2 g, yield of 16%).

ESI-MS (m/z) was obtained by Liquid Chromatograph-Mass Spectrometer analysis: 725.1[M+H]$^+$.

Example 36: Manufacture of Organic Optoelectronic Device

The anode substrate of ITO film with a film thickness of 100 nm was ultrasonically washed with distilled water, acetone and isopropanol, and placed in an oven to be dried. The surface thereof was treated by UV for 30 minutes, and then moved to the vacuum evaporation chamber. Each film was began to be evaporated at a vacuum degree of 2×10$^{-6}$ Pa, diphenyl naphthyl diamine (NPD) with a thickness of 60 nm and then 4,4',4''-tris(N-carbazolyl)triphenylamine (TCTA) with a thickness of 10 nm were evaporated to form a hole transport layer (HTL). 6 wt % of Ir(ppy)$_3$ was used as a green phosphorescent dopant material and 94 wt % of Compound 29 was used as a host material on the hole transport layer. The green phosphorescent dopant material and the host material were evaporated simultaneously to form a luminescent layer with a thickness of 30 nm. Then a thick bis(8-hydroxy-2-methylquinoline)aluminum diphenolate (BAlq) layer with a thickness of 5 nm was evaporated on the luminescent layer to form a hole blocking layer (HBL). 4,7-diphenyl-1,10-phenanthroline (Bphen) was evaporated on the hole blocking layer to form an electron transport layer (ETL) with a thickness of 20 nm. LiF with a thickness of 1 nm and Al with a thickness of 100 nm were evaporated in sequence on the electron transport layer as an electron injection layer (EIL) and a cathode. Thereby an organic optoelectronic device was produced.

The organic optoelectronic device has a structure of ITO(100 nm)/NPD(60 nm)/TCTA(10 nm)/Ir(ppy)$_3$: Compound 29(6 wt %:94 wt %,30 nm)/BAlq(5 nm)/Bphen(20 nm)/LiF(1 nm)/Al(100 nm).

Example 37: Manufacture of Organic Optoelectronic Device

Except that Compound 29 was replaced with Compound 30 as the host material, the organic optoelectronic device was manufactured according to the same method as that in Example 36.

Example 38: Manufacture of Organic Optoelectronic Device

Except that Compound 29 was replaced with Compound 55 as the host material, the organic optoelectronic device was manufactured according to the same method as that in Example 36.

Example 39: Manufacture of Organic Optoelectronic Device

Except that Compound 29 was replaced with Compound 40 as the host material, the organic optoelectronic device was manufactured according to the same method as that in Example 36.

Example 40: Manufacture of Organic Optoelectronic Device

Except that Compound 29 was replaced with Compound 1 as the host material, the organic optoelectronic device was manufactured according to the same method as that in Example 36.

Example 41: Manufacture of Organic Optoelectronic Device

Except that Compound 29 was replaced with Compound 33 as the host material, the organic optoelectronic device was manufactured according to the same method as that in Example 36.

Example 42: Manufacture of Organic Optoelectronic Device

Except that Compound 29 was replaced with Compound 80 as the host material, the organic optoelectronic device was manufactured according to the same method as that in Example 36.

Example 43: Manufacture of Organic Optoelectronic Device

Except that Compound 29 was replaced with Compound 84 as the host material, the organic optoelectronic device was manufactured according to the same method as that in Example 36.

Example 44: Manufacture of Organic Optoelectronic Device

Except that Compound 29 was replaced with Compound 91 as the host material, the organic optoelectronic device was manufactured according to the same method as that in Example 36.

Example 45: Manufacture of Organic Optoelectronic Device

Except that Compound 29 was replaced with Compound 6 as the host material, the organic optoelectronic device was manufactured according to the same method as that in Example 36.

Example 46: Manufacture of Organic Optoelectronic Device

Except that Compound 29 was replaced with Compound 12 as the host material, the organic optoelectronic device was manufactured according to the same method as that in Example 36.

Example 47: Manufacture of Organic Optoelectronic Device

Except that Compound 29 was replaced with Compound 17 as the host material, the organic optoelectronic device was manufactured according to the same method as that in Example 36.

Example 48: Manufacture of Organic Optoelectronic Device

Except that Compound 29 was replaced with Compound 24 as the host material, the organic optoelectronic device was manufactured according to the same method as that in Example 36.

Example 49: Manufacture of Organic Optoelectronic Device

Except that Compound 29 was replaced with Compound 51 as the host material, the organic optoelectronic device was manufactured according to the same method as that in Example 36.

Example 50: Manufacture of Organic Optoelectronic Device

Except that Compound 29 was replaced with Compound 76 as the host material, the organic optoelectronic device was manufactured according to the same method as that in Example 36.

Example 51: Manufacture of Organic Optoelectronic Device

Except that Compound 29 was replaced with Compound 128 as the host material, the organic optoelectronic device was manufactured according to the same method as that in Example 36.

Example 52: Manufacture of Organic Optoelectronic Device

Except that Compound 29 was replaced with Compound 138 as the host material, the organic optoelectronic device was manufactured according to the same method as that in Example 36.

Example 53: Manufacture of Organic Optoelectronic Device

Except that Compound 29 was replaced with Compound 162 as the host material, the organic optoelectronic device was manufactured according to the same method as that in Example 36.

Example 54: Manufacture of Organic Optoelectronic Device

Except that the co-evaporated layer (wherein 1 wt % TBRb was used as the doped material, 25 wt % Compound 29 was used as the co-doped material and 74 wt % CBP was used as the host material) with a thickness of 30 nm was used as the luminescent layer, the organic optoelectronic device was manufactured according to the same method as that in Example 36.

The organic optoelectronic device has a structure of ITO(100 nm)/NPD(60 nm)/TCTA(10 nm)/TBRb: Compound 29:CBP(1 wt %:25 wt %:74 wt %, 30 nm)/BAlq(5 nm)/Bphen(20 nm)/LiF(1 nm)/Al(100 nm).

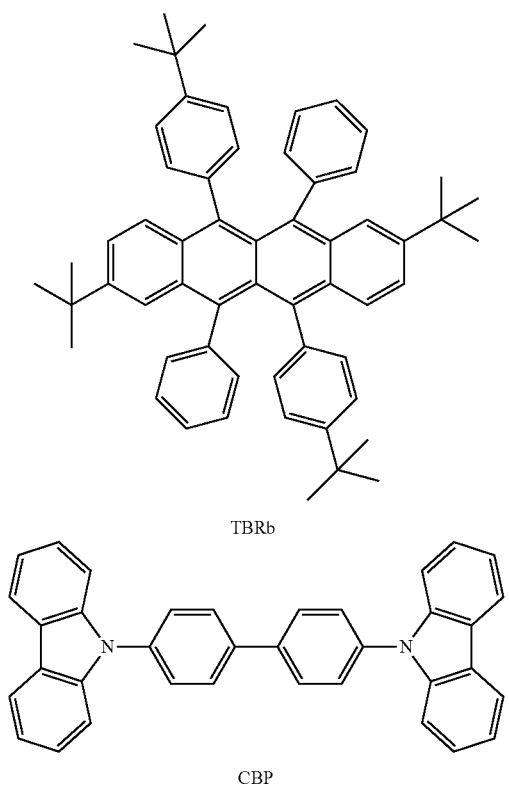

TBRb

CBP

Example 55: Manufacture of Organic Optoelectronic Device

Except that Compound 29 was replaced with Compound 30 as the host material, the organic optoelectronic device was manufactured according to the same method as that in Example 54.

Example 56: Manufacture of Organic Optoelectronic Device

Except that Compound 29 was replaced with Compound 1 as the host material, the organic optoelectronic device was manufactured according to the same method as that in Example 54.

Example 57: Manufacture of Organic Optoelectronic Device

Except that Compound 29 was replaced with Compound 33 as the host material, the organic optoelectronic device was manufactured according to the same method as that in Example 54.

Example 58: Manufacture of Organic Optoelectronic Device

Except that Compound 29 was replaced with Compound 103 as the host material, the organic optoelectronic device was manufactured according to the same method as that in Example 54.

Comparative Example 1: Manufacture of Organic Optoelectronic Device

Except that the co-evaporated layer (wherein 1 wt % TBRb was used as the doped material and 99 wt % CBP was used as the host material) with a thickness of 30 nm was used as the luminescent layer, the organic optoelectronic device was manufactured according to the same method as that in Example 54.

Performance Evaluation of the Organic Optoelectronic Devices

Currents of the organic optoelectronic devices manufactured in Examples 36-58 and Comparative Example 1 were tested at different voltages using Keithley 2365A digital nanovoltmeter, and then the current density of the organic optoelectronic devices at different voltages were obtained by dividing the currents by luminescence areas. Brightness and radiant energy flux density of the organic optoelectronic devices manufactured in Examples 36-58 and Comparative Example 1 were tested at different voltages using Konicaminolta CS-2000 Spectroradiometer. Current efficiency (Cd/A) and external quantum efficiency (EQE) at the same current density (10 mA/cm$^2$) were obtained according to the current density and brightness of the organic optoelectronic devices at different voltages.

As shown in the experiments, as for the compounds in Examples 36-53, the test voltage is less than 5V, the current efficiency is higher than or equal to 39 Cd/A and EQE is higher than 15, which indicates that the tested compounds have a function as a host material. The results of Examples 36-44 are shown in Table 2.

The results of Examples 54-58 and Comparative Example 1 are shown in Table 3.

TABLE 2

| The tested compounds used as a host material | | |
|---|---|---|
| Voltage (V) | Current efficiency (Cd/A) | EQE |
| Example 36 | 4.5 | 42.8 | 17.2 |
| Example 37 | 4.6 | 43.1 | 16.9 |
| Example 38 | 4.0 | 48.6 | 18.8 |
| Example 39 | 4.2 | 45.1 | 17.9 |
| Example 40 | 4.4 | 46.2 | 17.4 |
| Example 41 | 4.3 | 47.8 | 18.4 |
| Example 42 | 4.7 | 41.4 | 16.7 |
| Example 43 | 4.7 | 40.9 | 15.8 |
| Example 44 | 4.9 | 39.0 | 15.2 |

TABLE 3

| The tested compounds used as the co-doped material | | |
|---|---|---|
| Voltage (V) | Current efficiency (Cd/A) | EQE |
| Example 54 | 6.9 | 35.4 | 9.5 |
| Example 55 | 8.2 | 25.2 | 8.1 |
| Example 56 | 7.6 | 32.2 | 9.3 |
| Example 57 | 7.4 | 38.9 | 10.7 |
| Example 58 | 8.5 | 19.2 | 7.2 |
| Comparative Example 1 | 9.3 | 7.9 | 2.5 |

According to the test results of the compounds in Examples 36-53, at the same current density of 10 mA/cm$^2$, the driving voltages of these compounds are less than 5V, the current efficiencies are higher than 39 Cd/A, and EQEs are higher than 15. Therefore, all the compounds tested in Examples 36-53 have a lower driving voltage, higher current efficiency and higher external quantum efficiency, which indicates that the compounds of the present application have a function as a host material.

The test results in Table 3 show that the compounds tested in Examples 54-58 have lower driving voltage, higher current efficiency and higher external quantum efficiency with respect to comparative Example 1, which indicates that the compounds of the present application have a function as a co-doped material or a doped material.

In view of the above, the organic photoelectric devices comprising the compounds of the present application have excellent luminescence performance.

The above general description of the technical solutions involved in present application and the description of the specific embodiments thereof should not be construed as constituting any limitation to the technical solutions of the present application. According to the present application, one of ordinary skill in the art could add, delete or combine the technical features disclosed in the above general description or/and the specific embodiments (comprising the examples) to form other technical solutions belonging to the present application without departing from the inventive concept involved.

What is claimed is:

1. A compound of Formula (I):

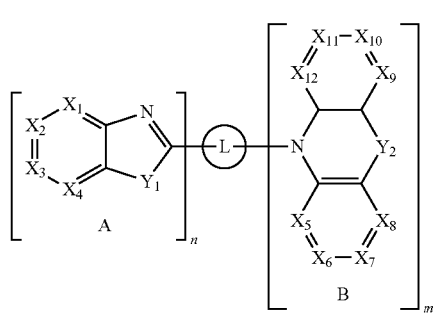

wherein
$X_1$ to $X_{12}$ are each independently $CR_1$ or N;
$Y_1$ is O, S or $NR_2$;
$Y_2$ is O, S, $CR_3R_4$, $NR_5$ or $SiR_6R_7$;
$R_1$ to $R_7$ are each independently hydrogen, deuterium, $C_{1-30}$ alkyl, $C_{6-30}$ aryl or $C_{2-20}$ heteroaryl;
L is a linking moiety which enables the structure of Formula (I) to form a conjugated system;
when n is 1, 2 or 3, m is 2 or 3; when n is 2 or 3, m is 1, 2 or 3;
if n is greater than 1, each Moiety A in Formula (I) is the same as each other or different from each other; and
if m is greater than 1, each Moiety B in Formula (I) is the same as each other or different from each other.

2. The compound according to claim 1, wherein said L is $C_{6-30}$ aryl or $C_{2-30}$ heteroaryl.

3. The compound according to claim 1, wherein said L is selected from the following structures:

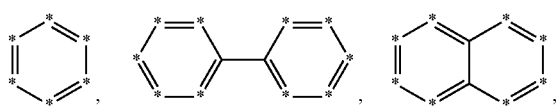

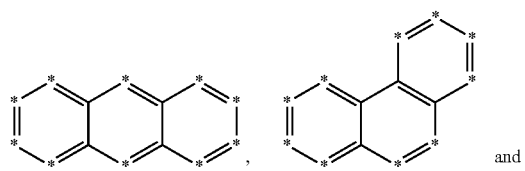

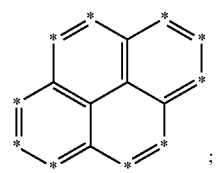

wherein, * represents $CR_8$, N or a site linked to said Moiety A or said Moiety B, and said $R_8$ is each independently hydrogen, deuterium, $C_{1-6}$ alkyl, $C_{6-16}$ aryl or $C_{2-6}$ heteroaryl.

4. The compound according to claim 3, wherein substitution positions of said Moiety A and said Moiety B on said L are spaced by at least one atom.

5. The compound according to claim 1, wherein said Moiety A is selected from the following groups:

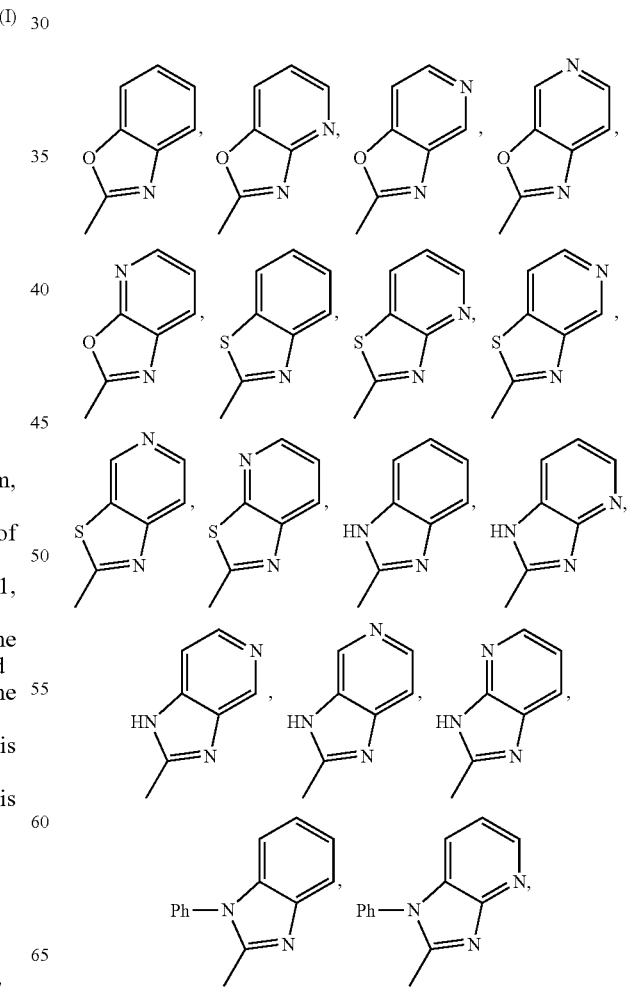

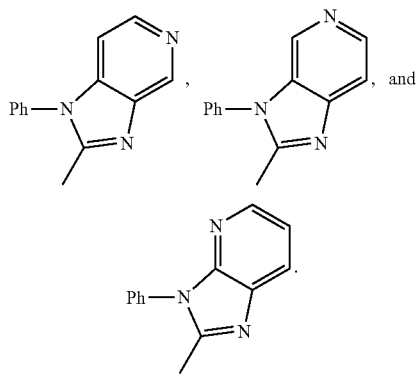

6. The compound according to claim 1, wherein said Moiety B is selected from the following groups:

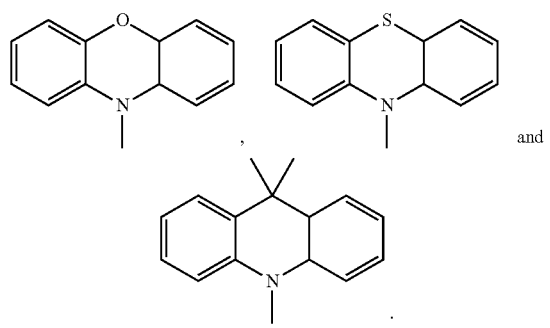

7. The compound according to claim 1, wherein the energy gap $\Delta E_{st}$ between the lowest singlet state and the lowest triplet state of said compound is less than or equal to 0.30 eV.

8. The compound according to claim 7, wherein the energy gap $\Delta E_{st}$ between the lowest singlet state and the lowest triplet state of said compound is less than or equal to 0.25 eV.

9. The compound according to claim 7, wherein the energy gap $\Delta E_{st}$ between the lowest singlet state and the lowest triplet state of said compound is less than or equal to 0.15 eV.

10. The compound according to claim 7, wherein the energy gap $\Delta E_{st}$ between the lowest singlet state and the lowest triplet state of said compound is less than or equal to 0.1 eV.

11. The compound according to claim 7, wherein the energy gap $\Delta E_{st}$ between the lowest singlet state and the lowest triplet state of said compound is less than or equal to 0.05 eV.

12. The compound according to claim 7, wherein the energy gap $\Delta E_{st}$ between the lowest singlet state and the lowest triplet state of said compound is less than or equal to 0.02 eV.

13. The compound according to claim 7, wherein the energy gap $\Delta E_{st}$ between the lowest singlet state and the lowest triplet state of said compound is less than or equal to 0.01 eV.

14. The compound according to claim 1, selected from:

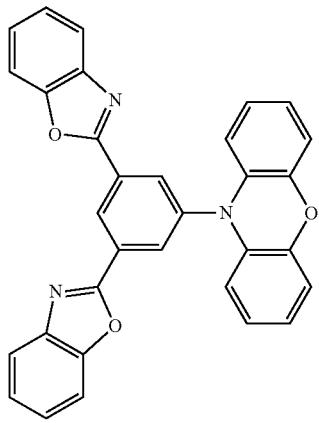

1

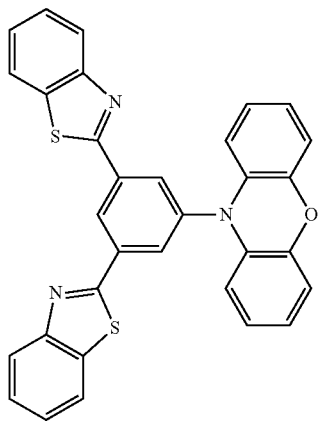

2

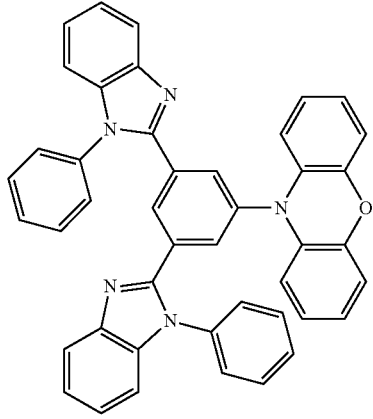

3

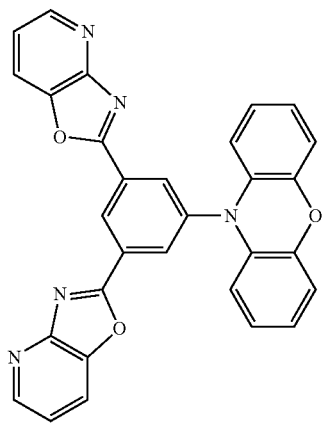
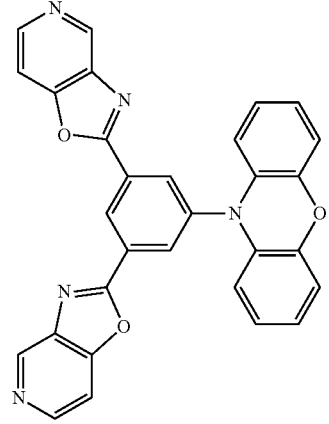
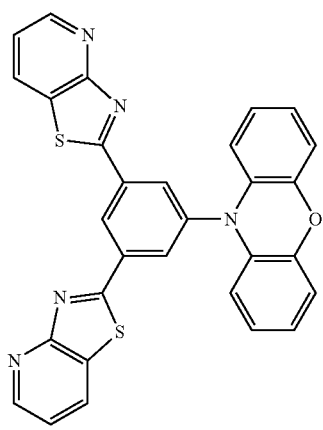
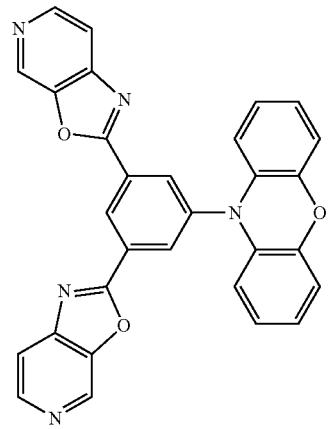
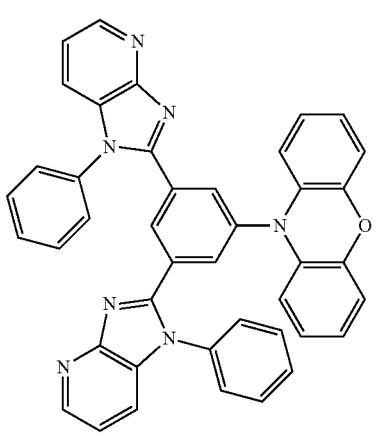
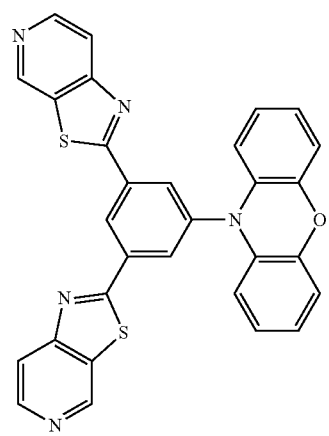

97
-continued
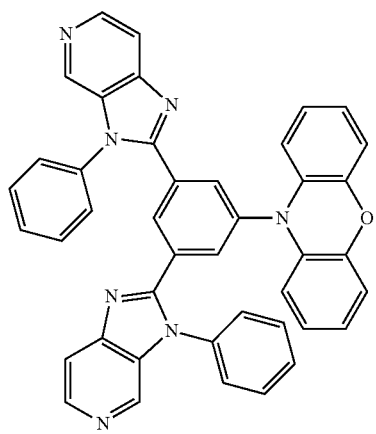
10
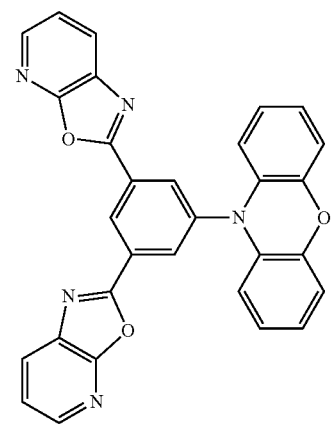
11
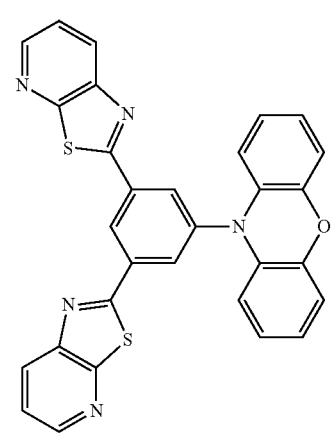
12
98
-continued
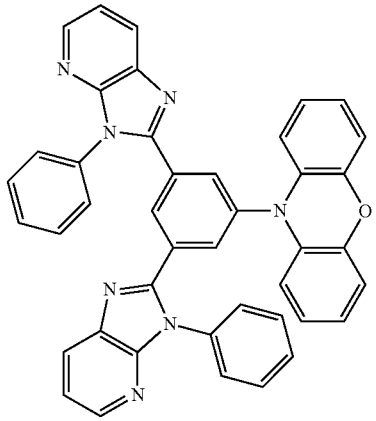
13
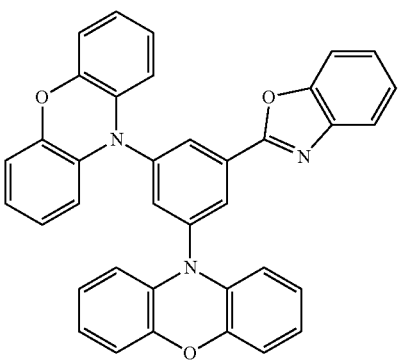
14
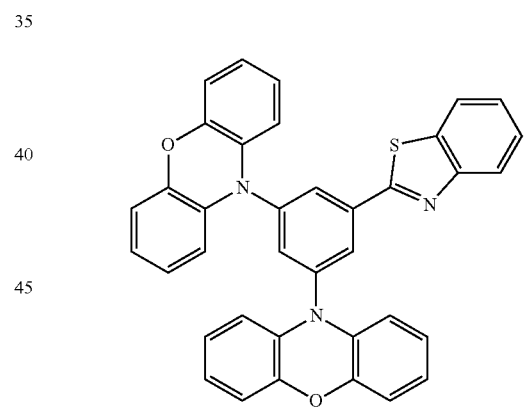
15
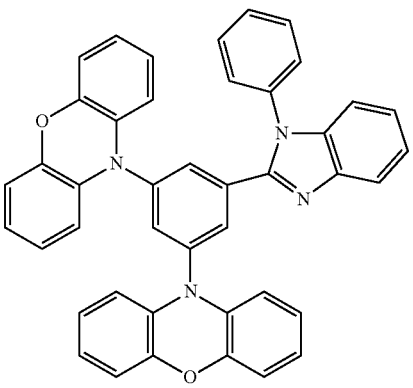
16

17
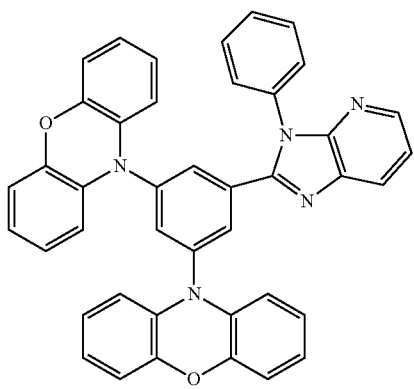
18
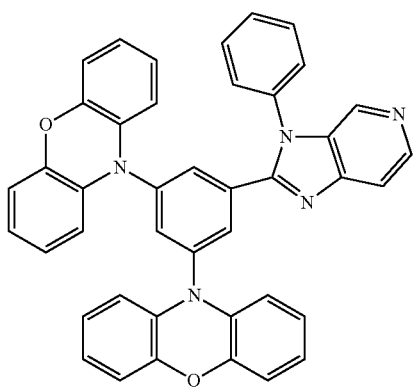
19
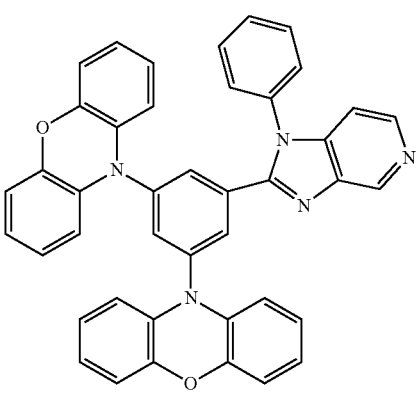
20
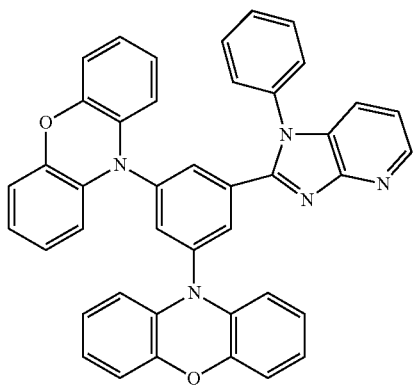
21
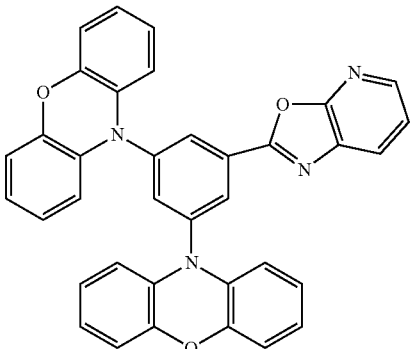
22
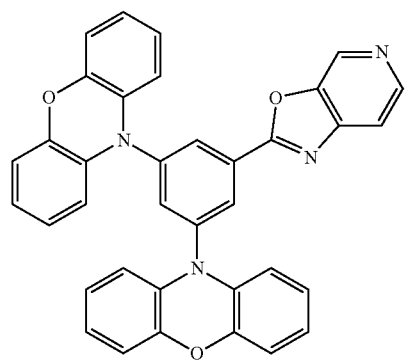
23
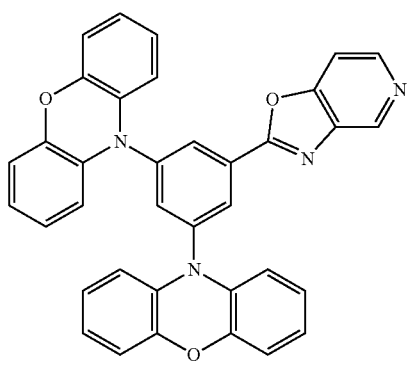
24
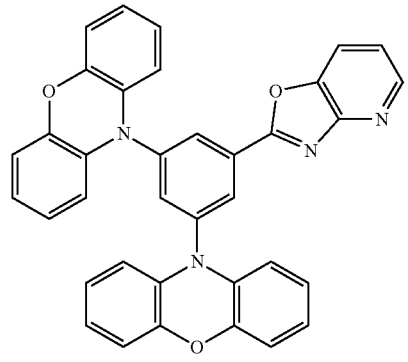

101
25
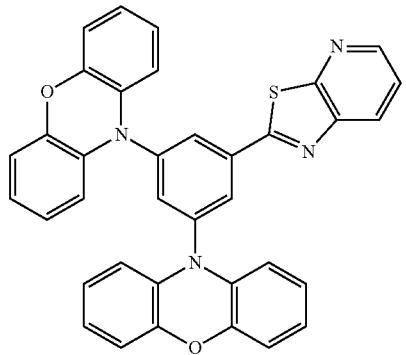
26
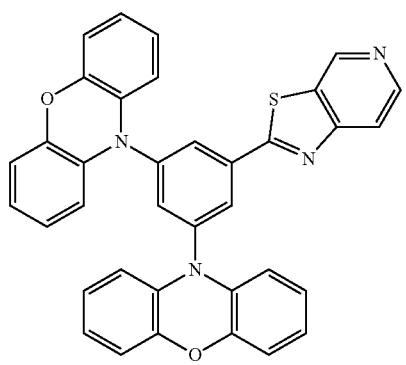
27
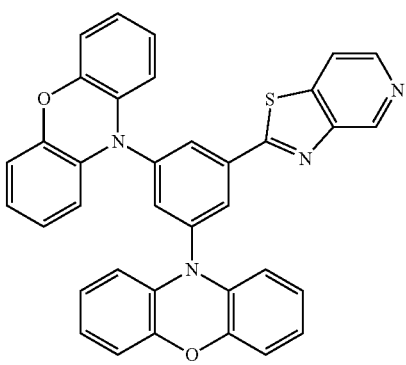
28
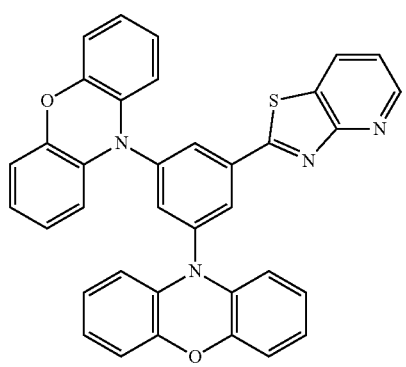
102
29
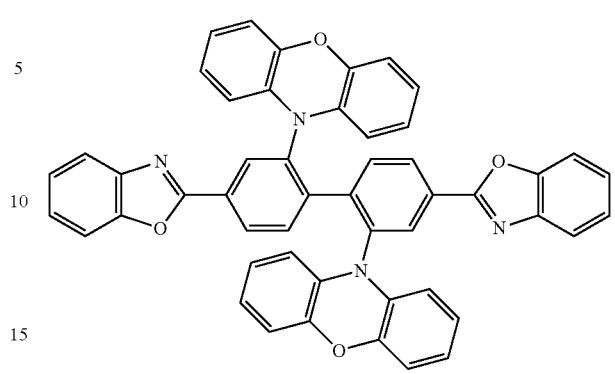
30
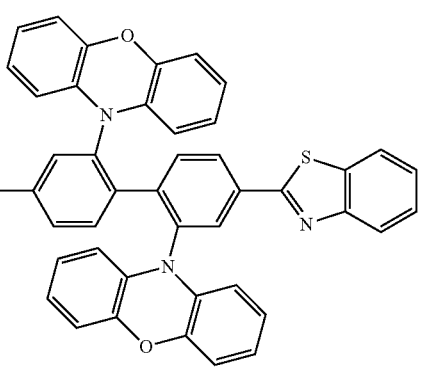
31
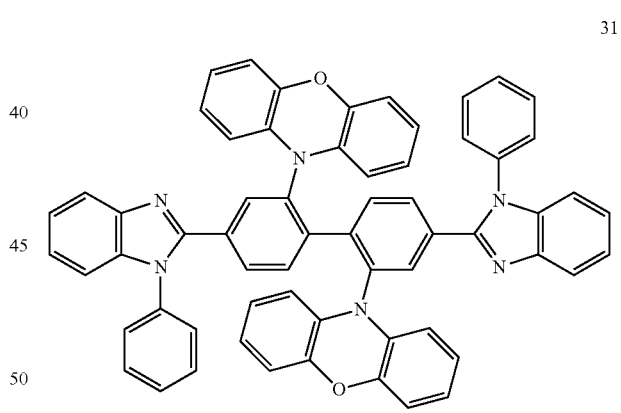
32
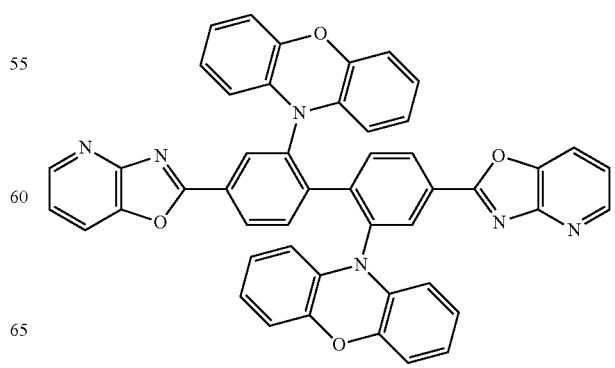

-continued
33
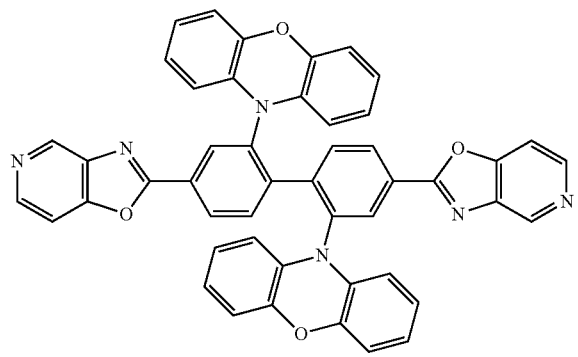
34
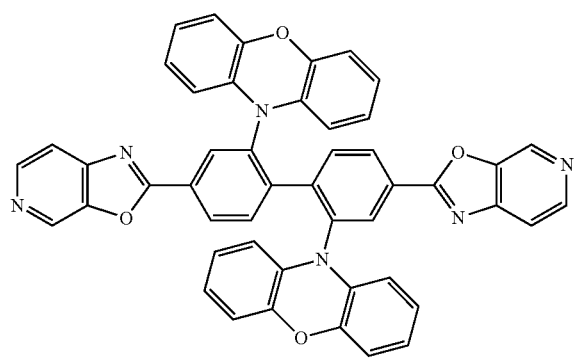
35
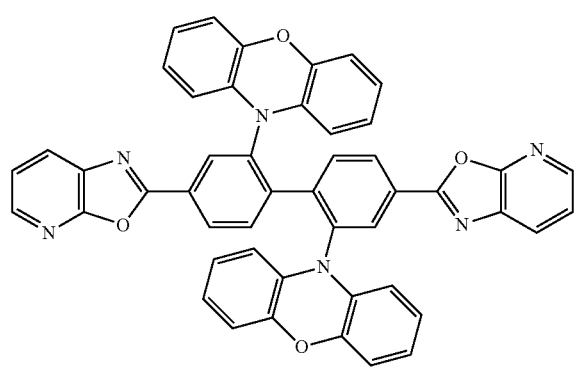
36
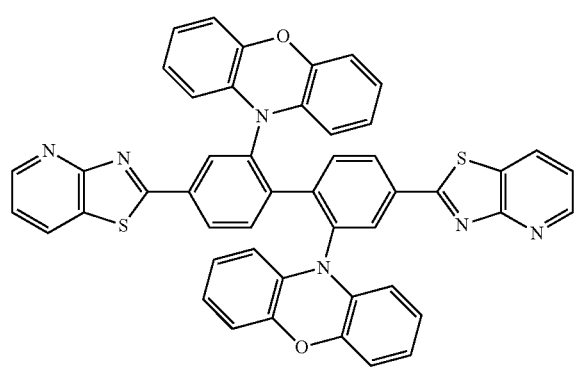
-continued
37
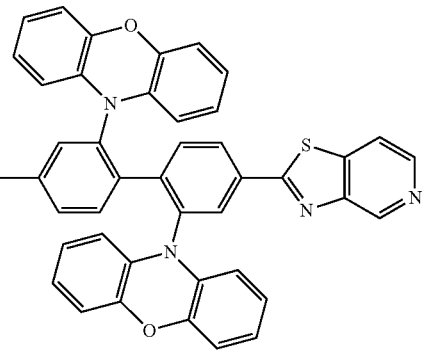
38
39
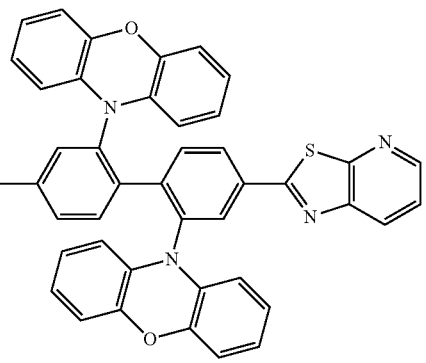
40
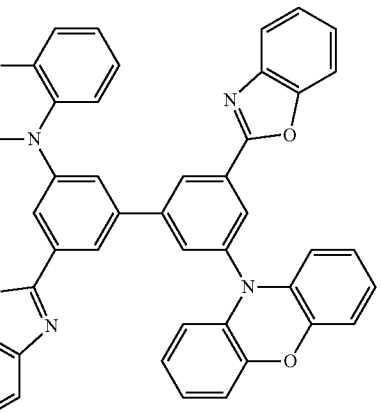

41
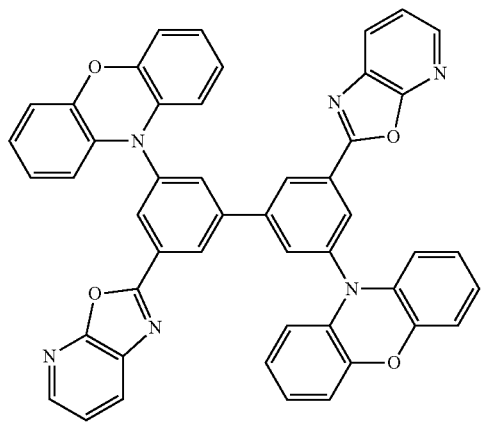
42
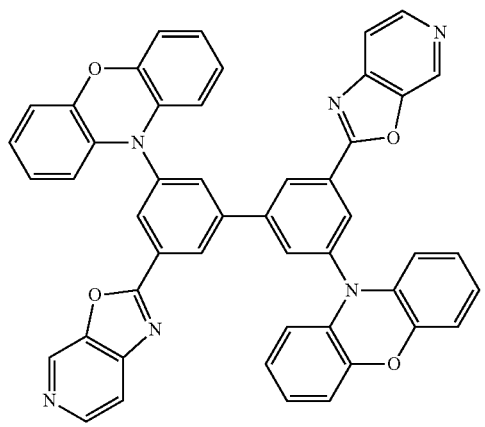
43
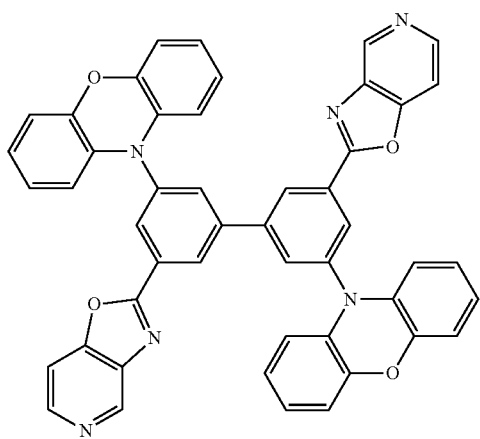
44
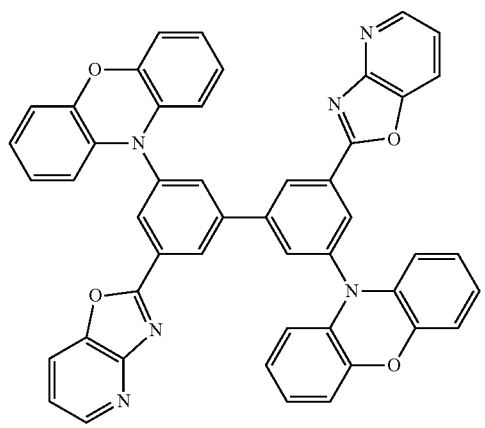
45
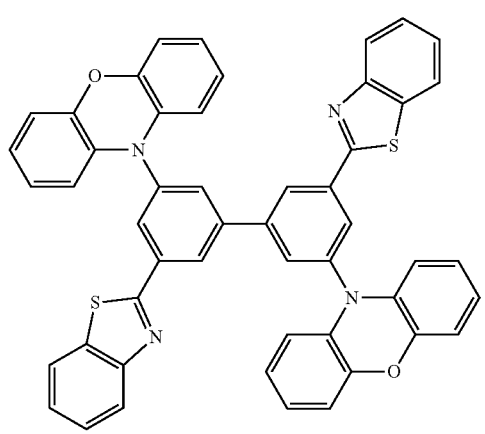
46
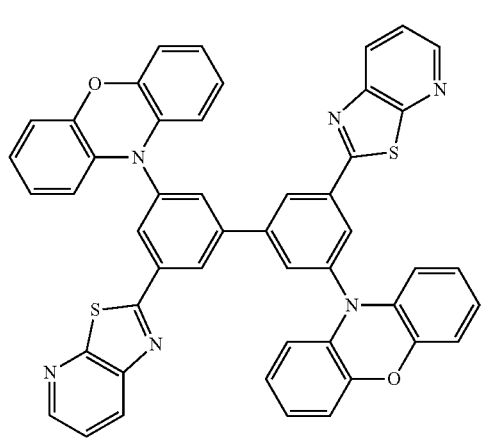

47
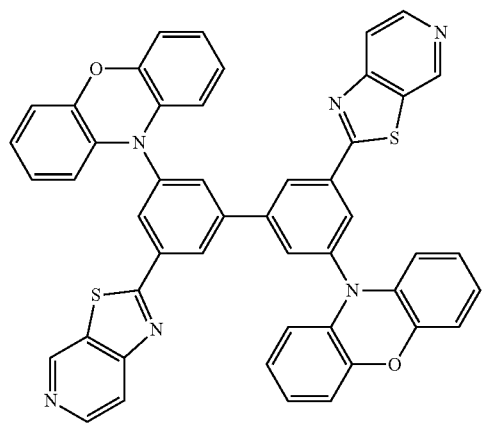
48
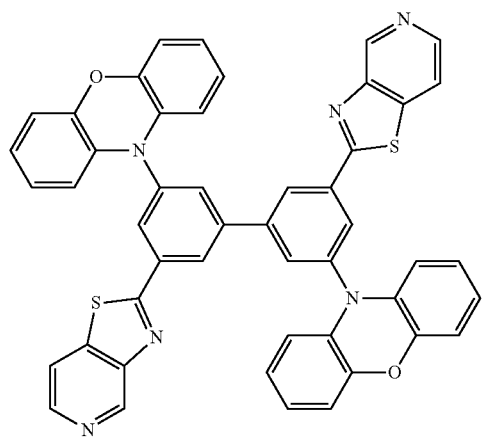
49
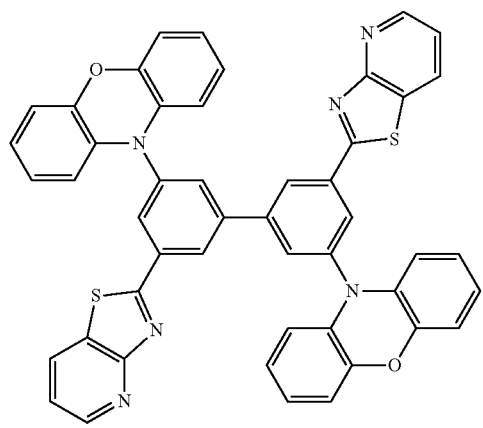
50
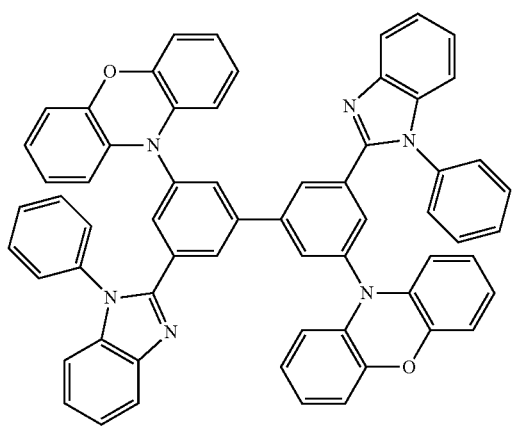
51
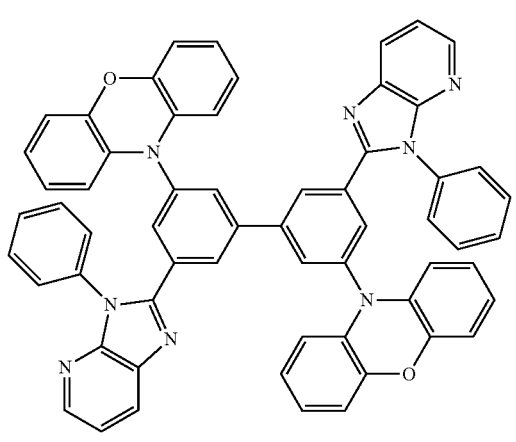
52
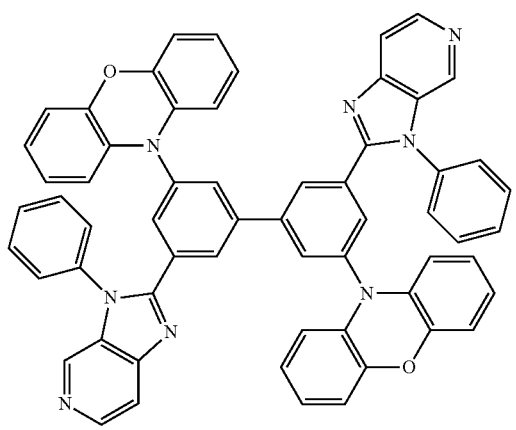

53
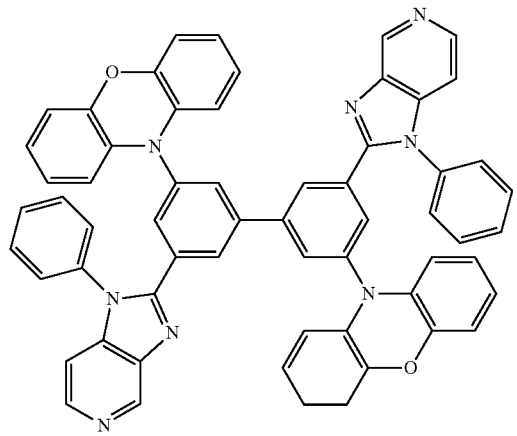
54
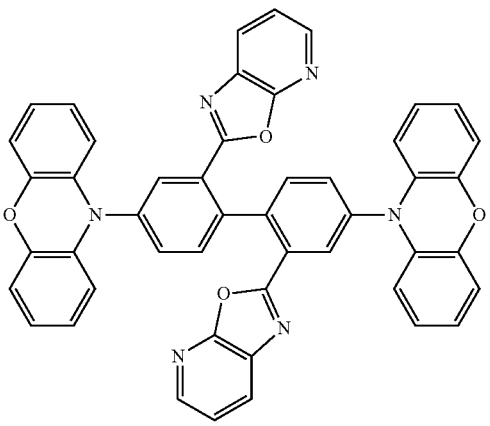
55
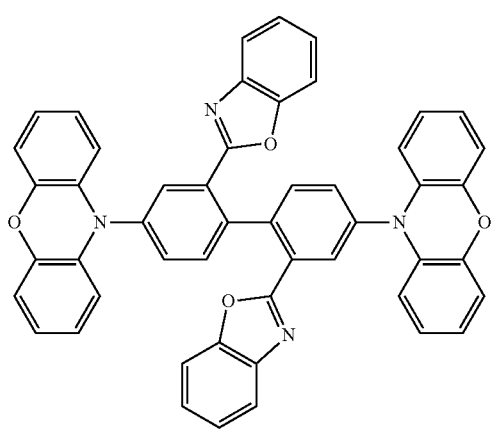
56
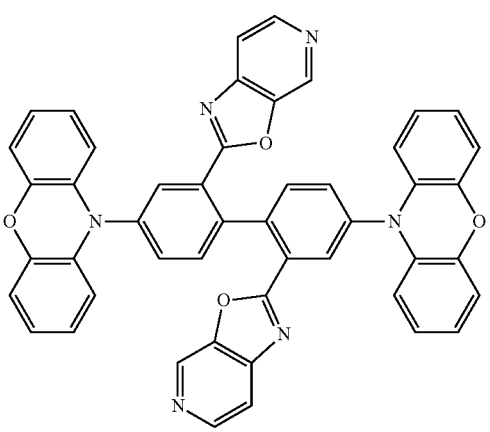
57
58
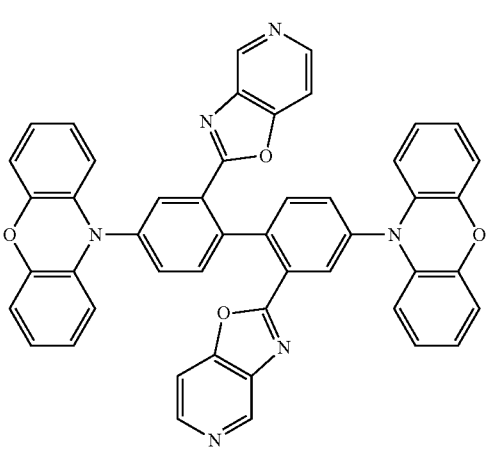

111
-continued
59
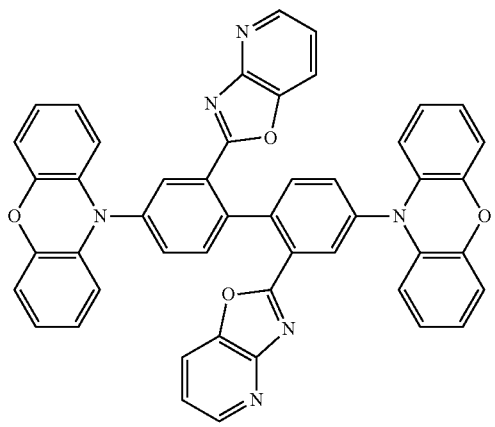
60
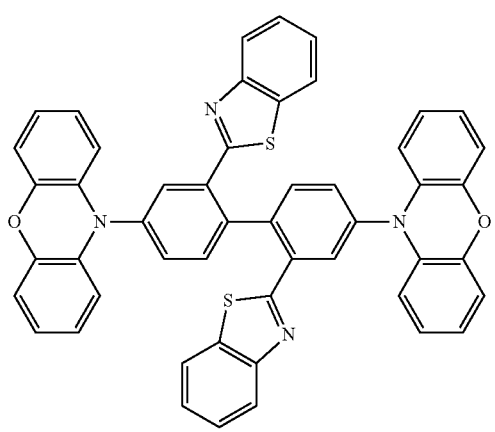
61
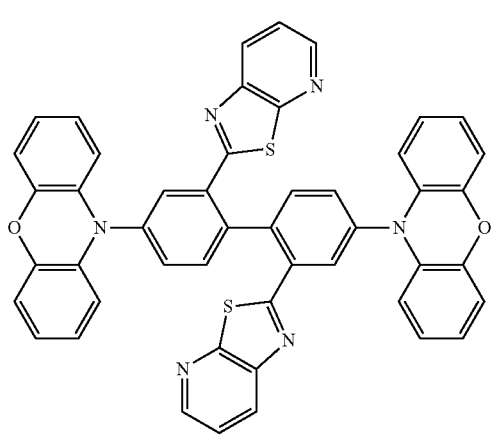
112
-continued
62
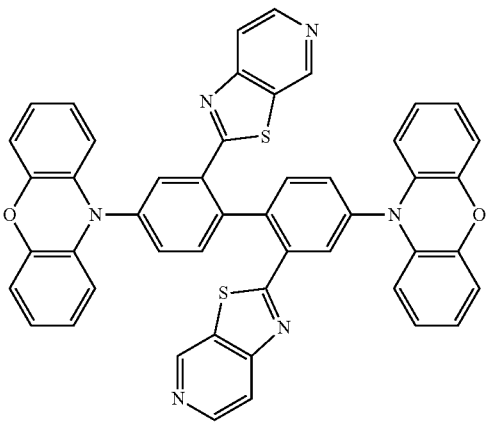
63
64
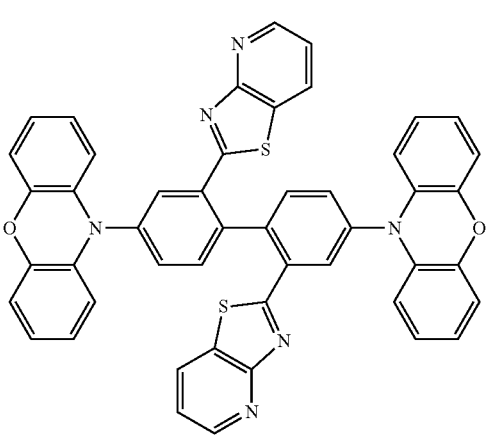

65
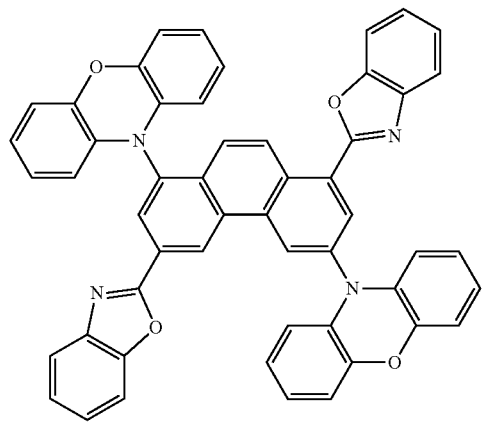
66
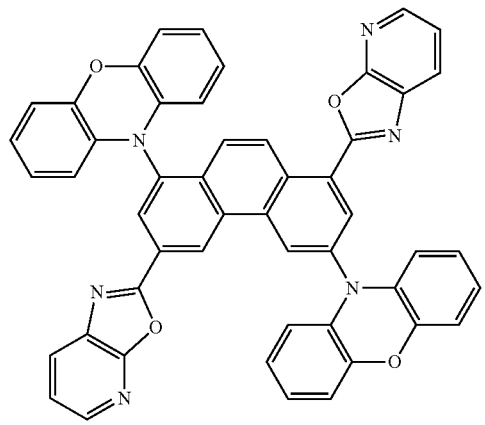
67
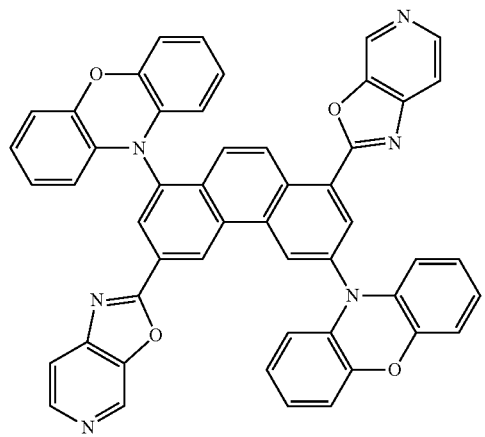
68
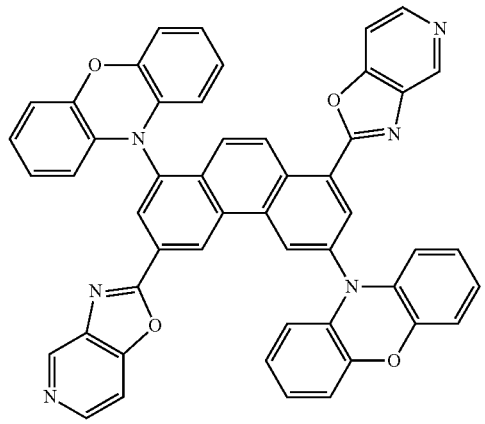
69
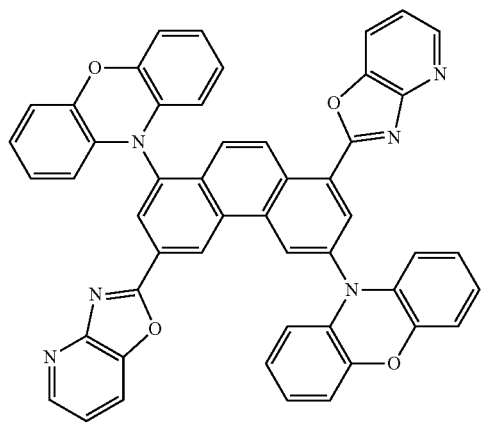
70
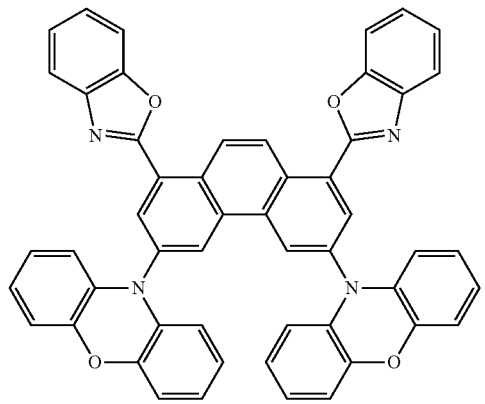
71
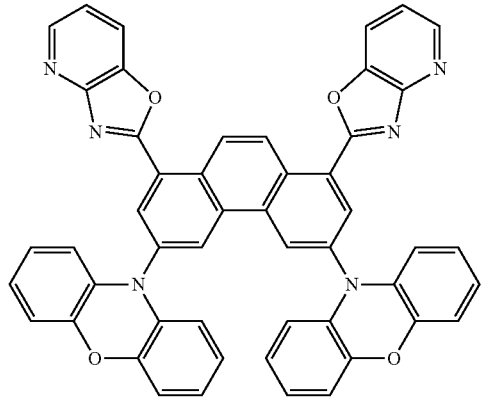

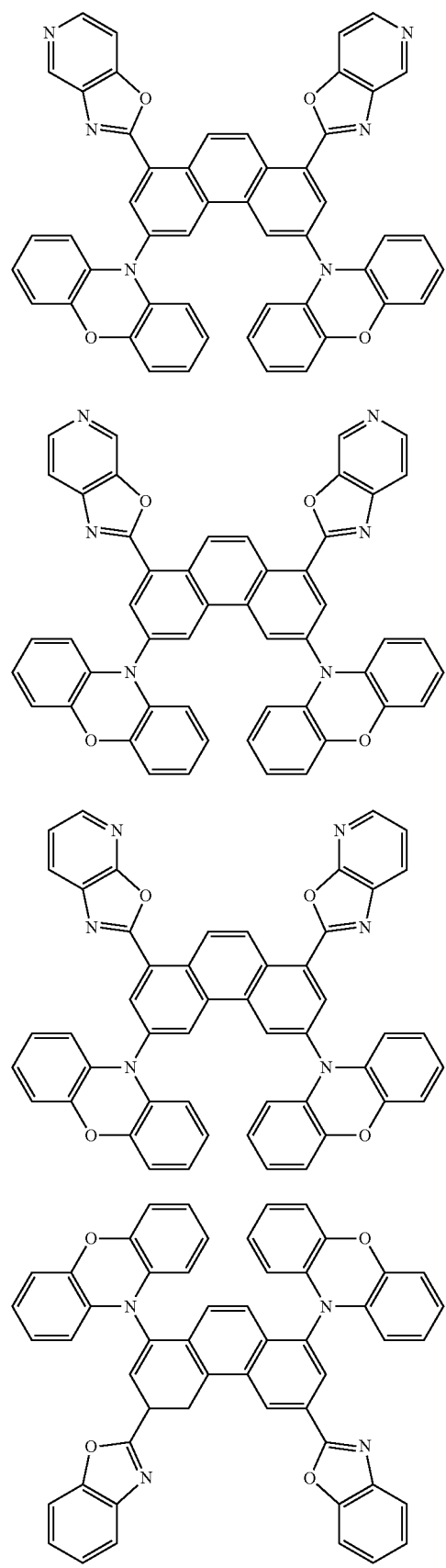
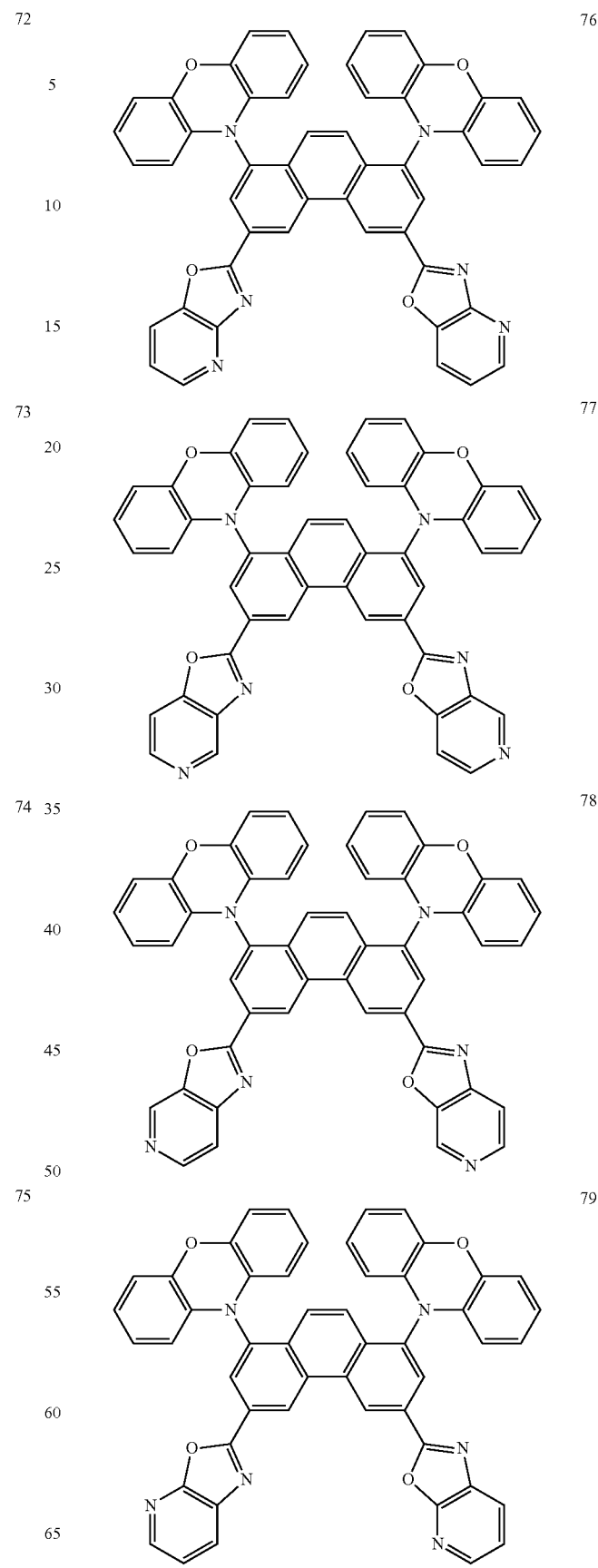

80
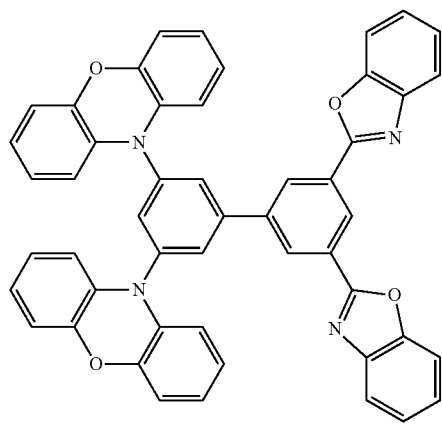
81
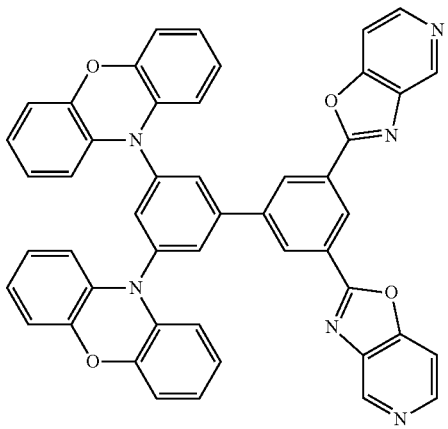
82
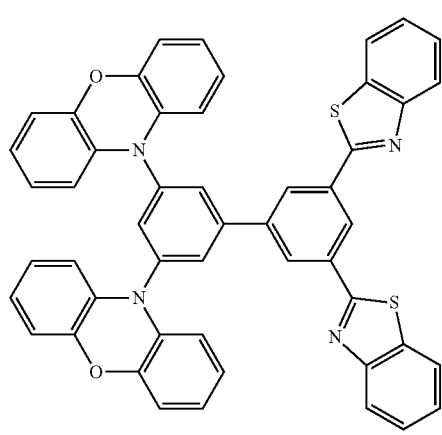
83
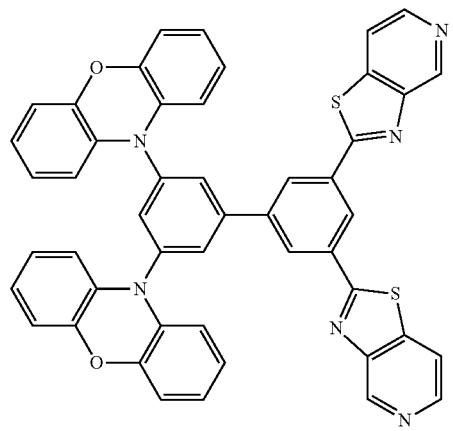
84
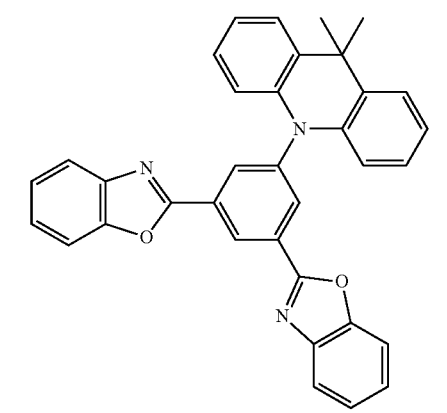
85
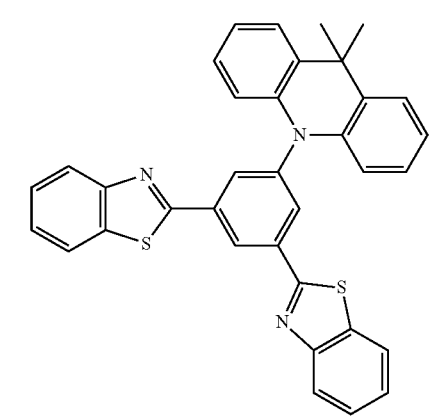
86
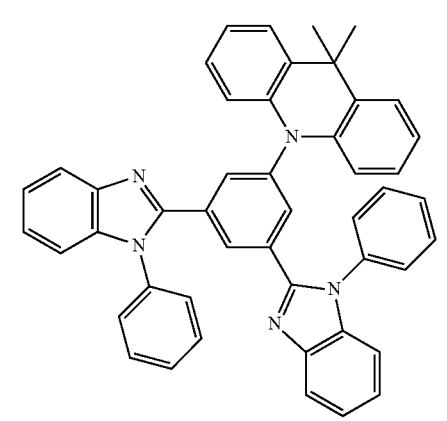

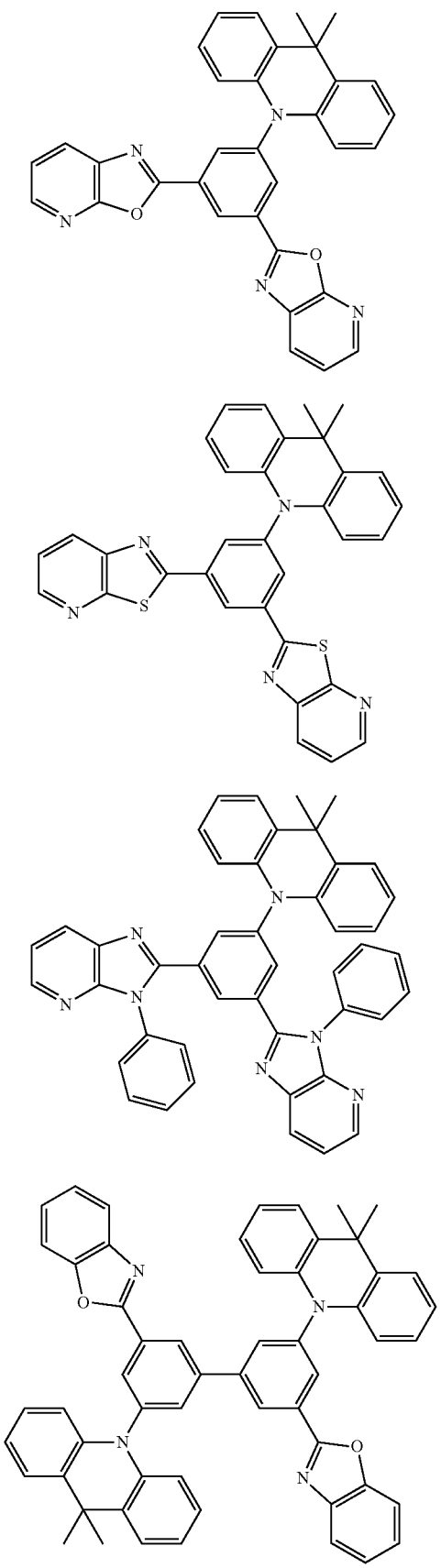

95
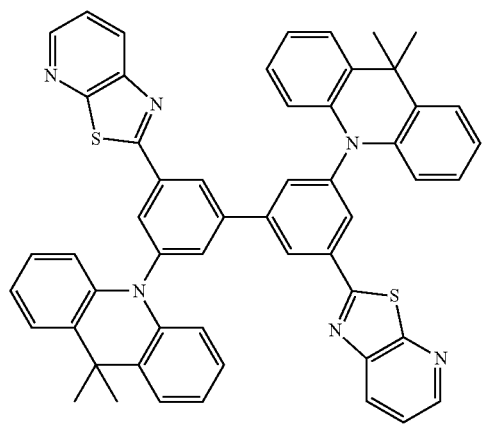
96
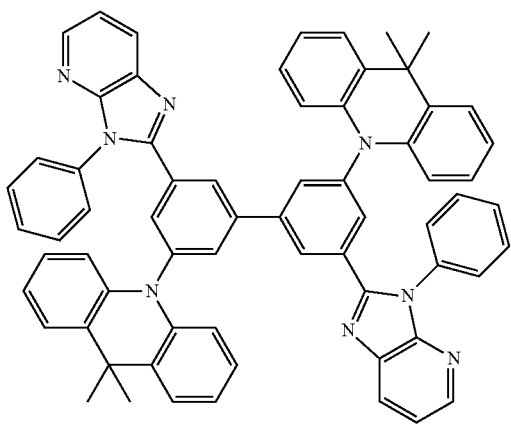
97
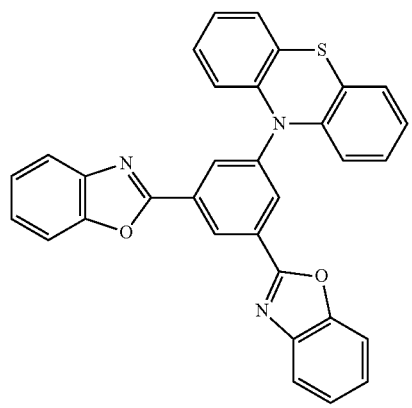
98
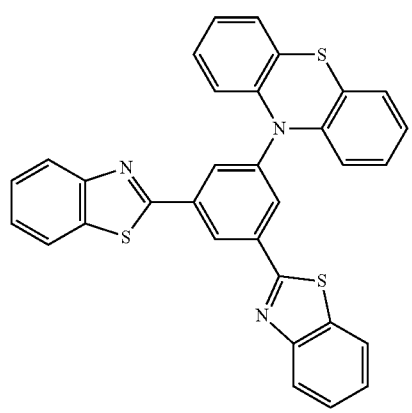
99
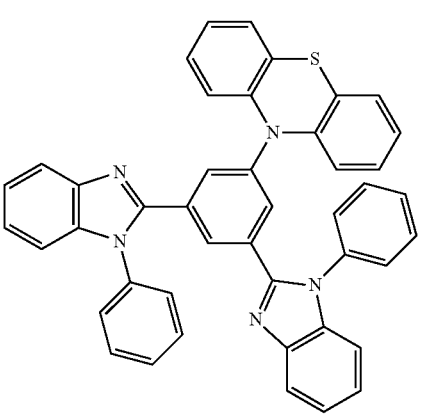
100
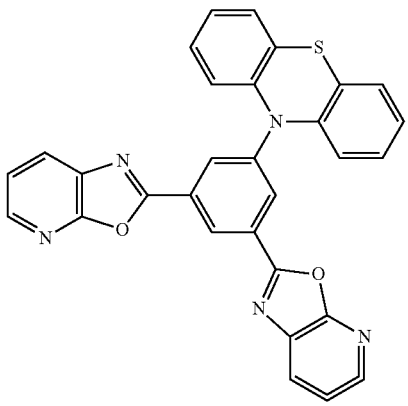
101
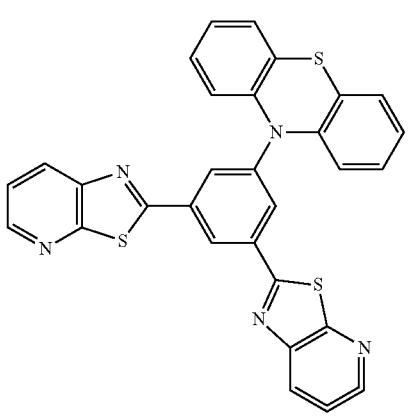
102
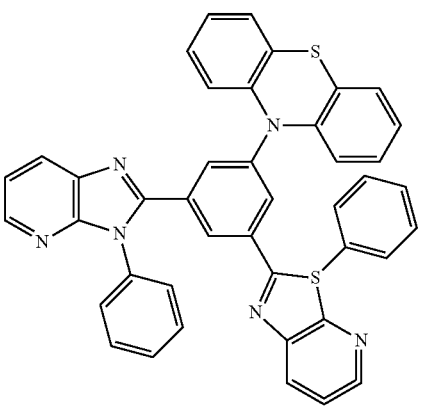

123
-continued
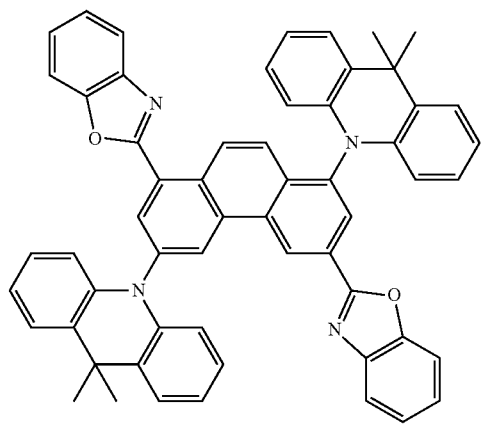
103
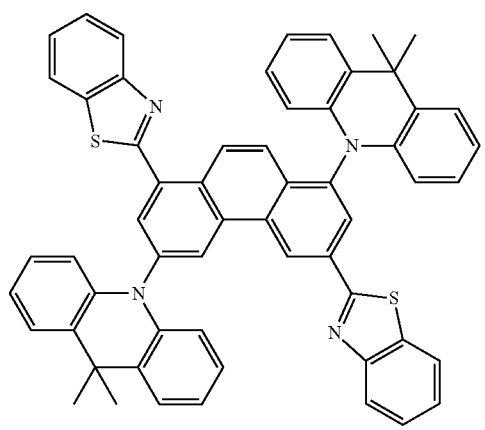
104
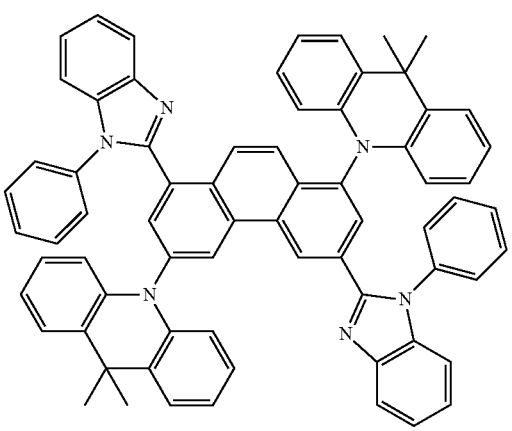
105
124
-continued
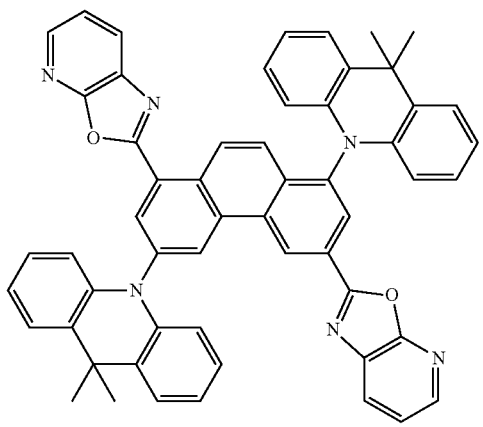
106
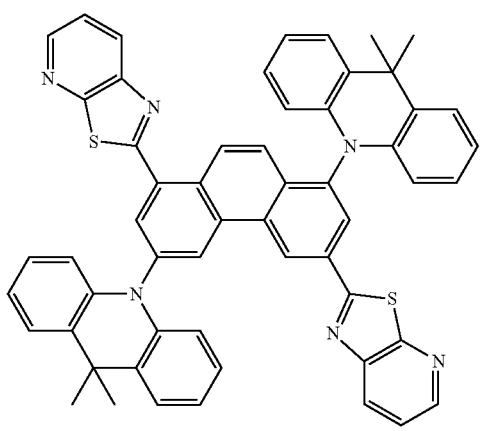
107
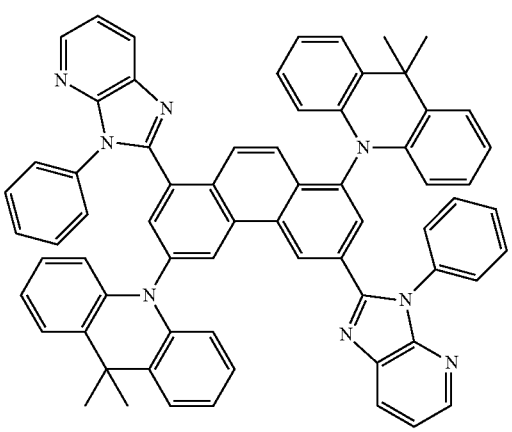
108

125
-continued
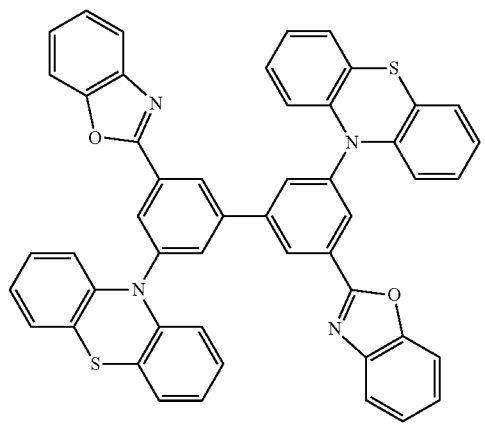
109
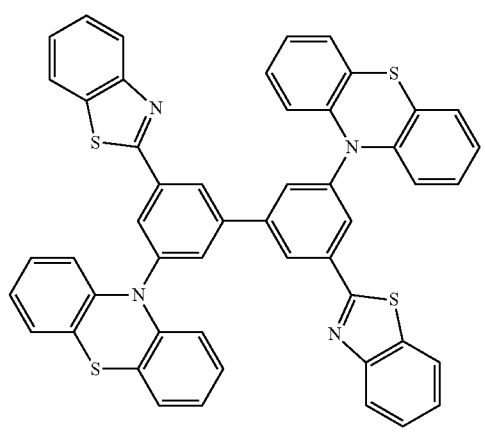
110
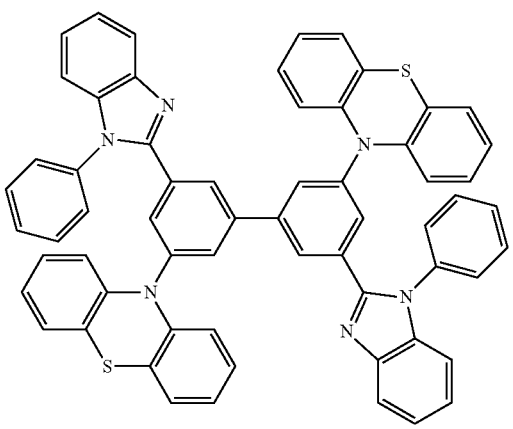
111
126
-continued
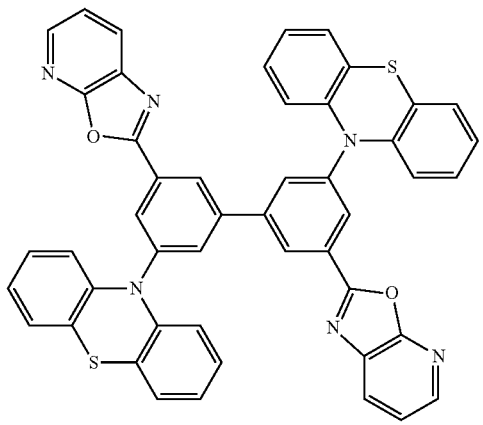
112
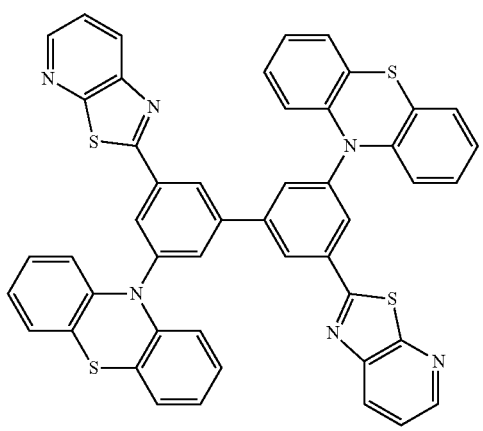
113
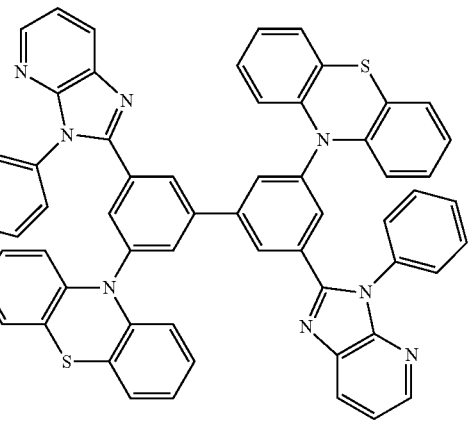
114

-continued
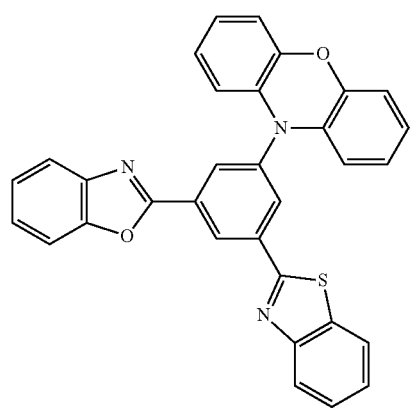 115
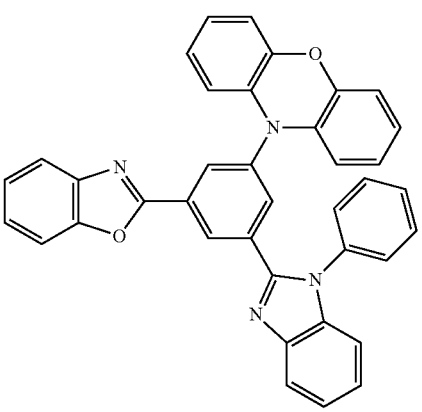 116
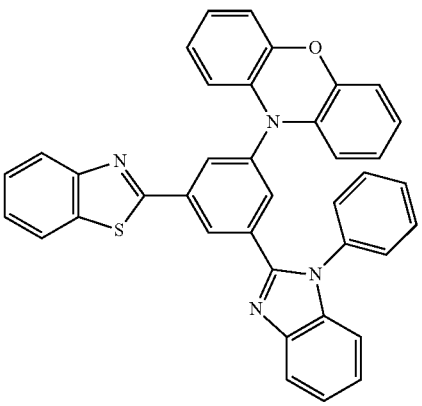 117
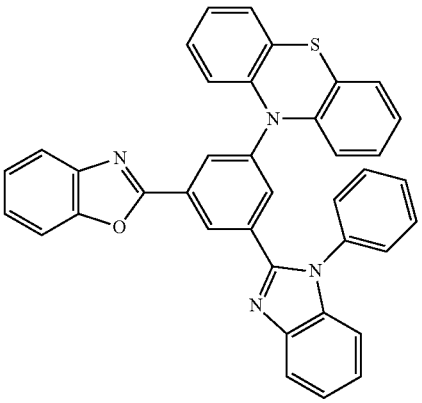 118
-continued
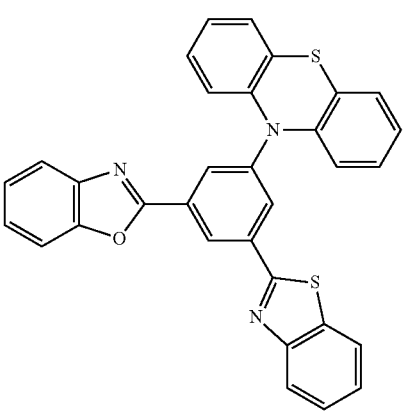 119
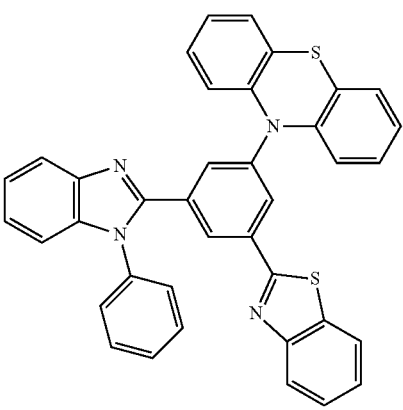 120
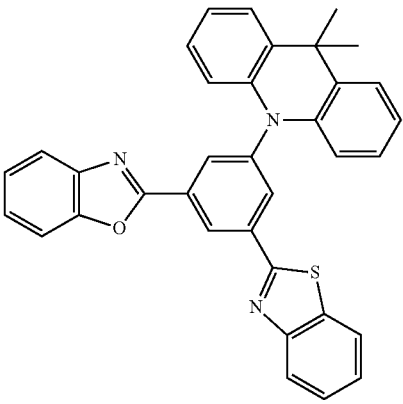 121
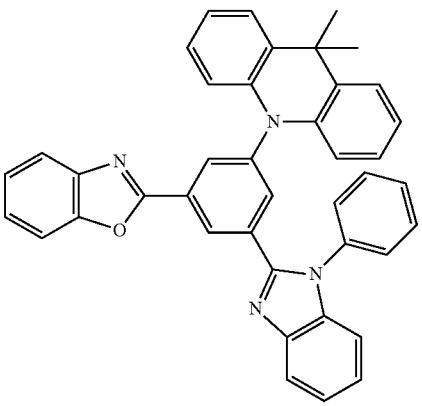 122

-continued
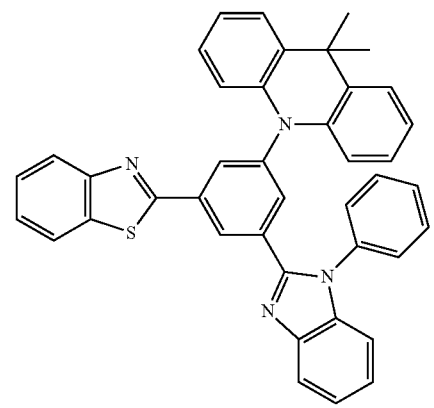
123
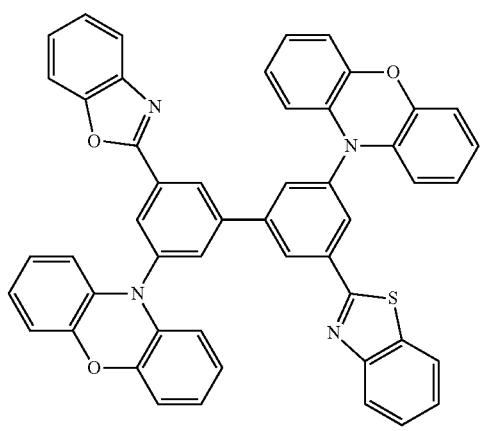
124
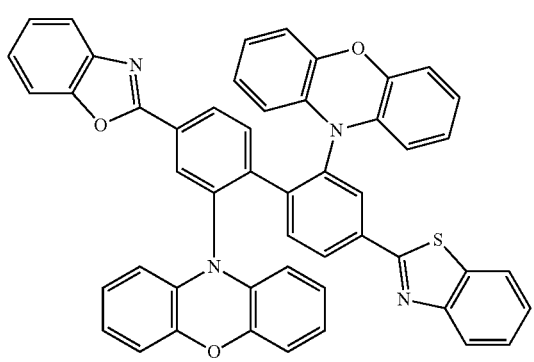
125
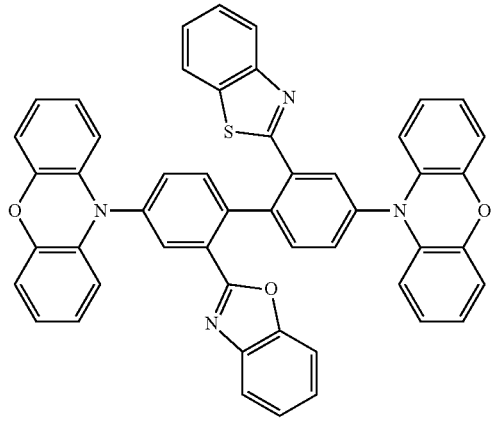
126
-continued
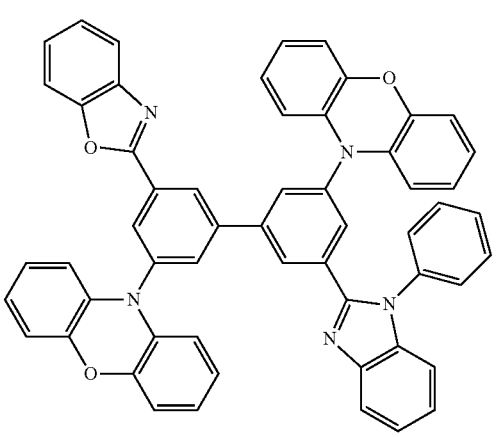
127
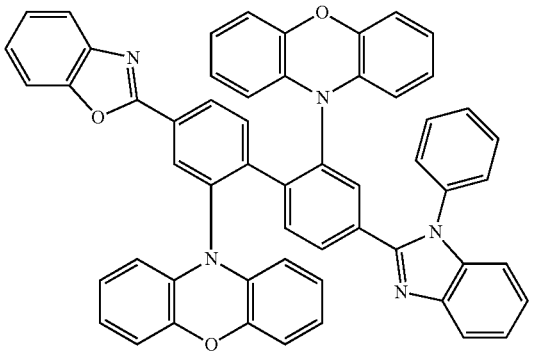
128
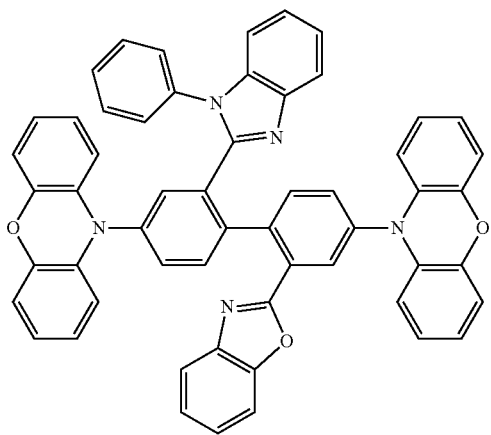
129

-continued
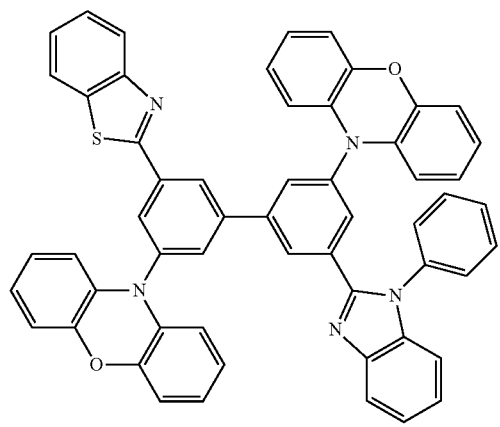
130
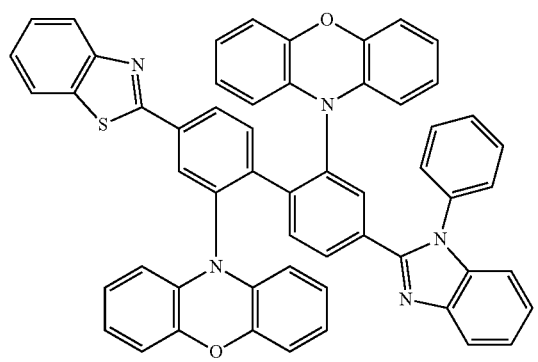
131
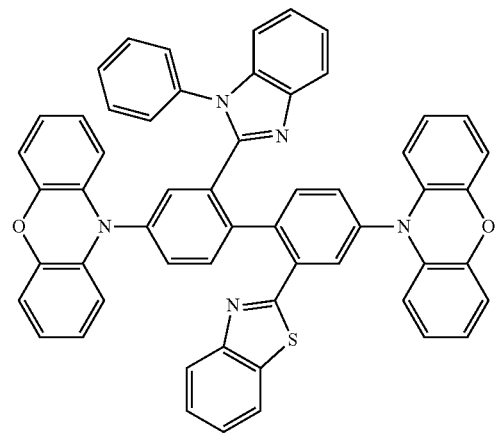
132
-continued
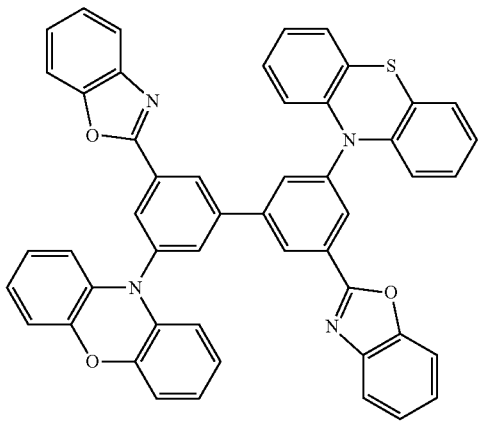
133
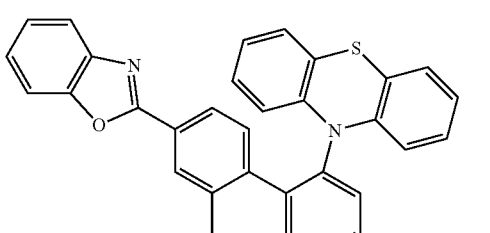
134
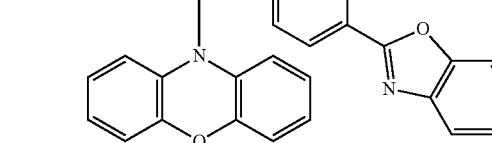
135
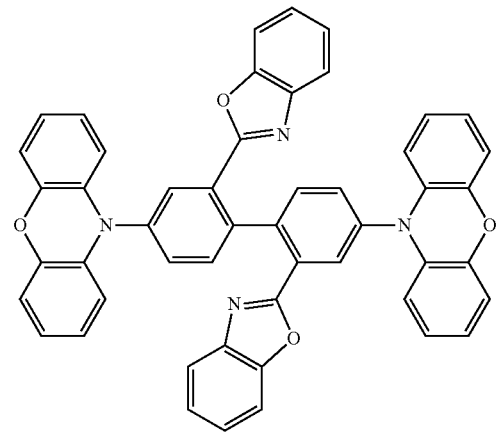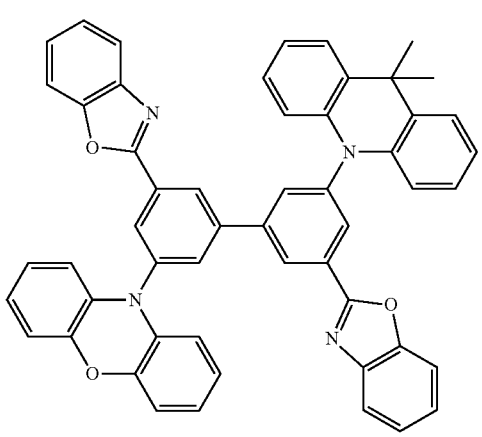
136

133
-continued
137
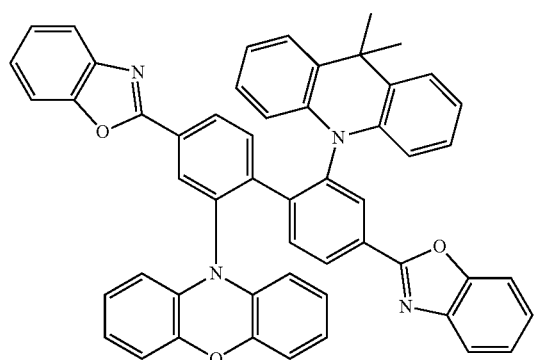
138
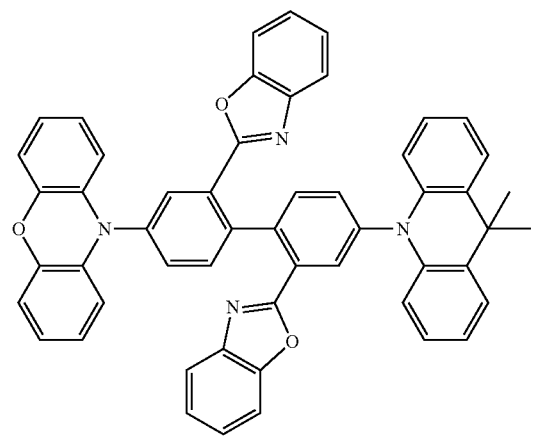
139
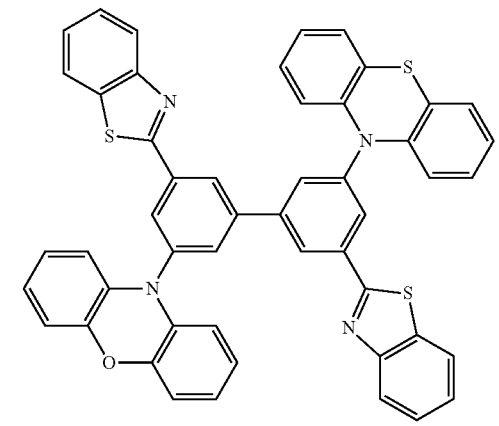
140
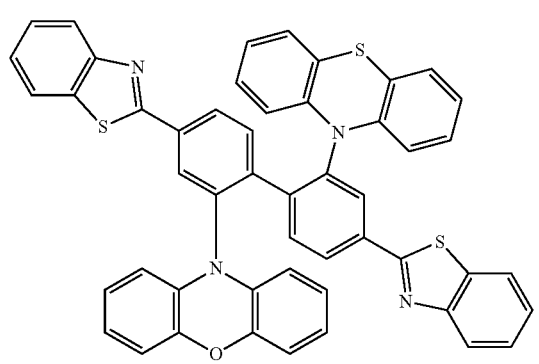
134
-continued
141
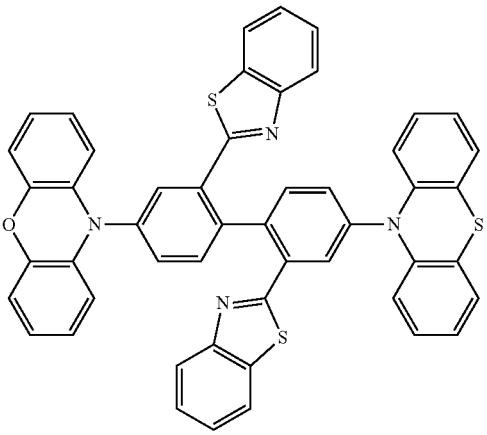
142
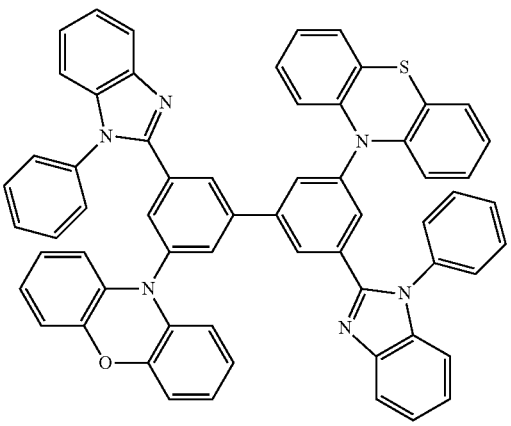
143
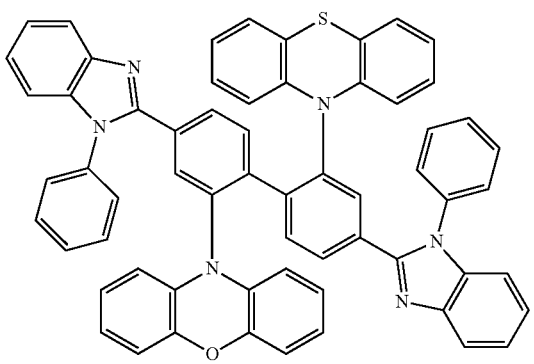

144
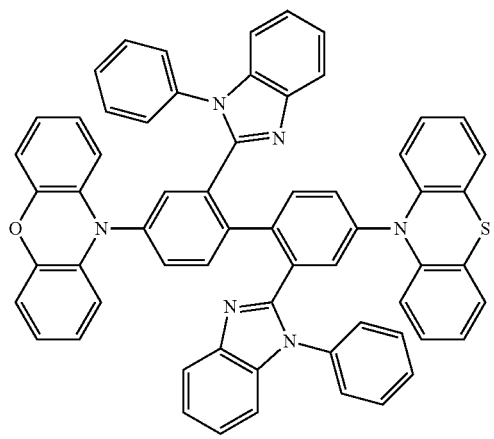
147
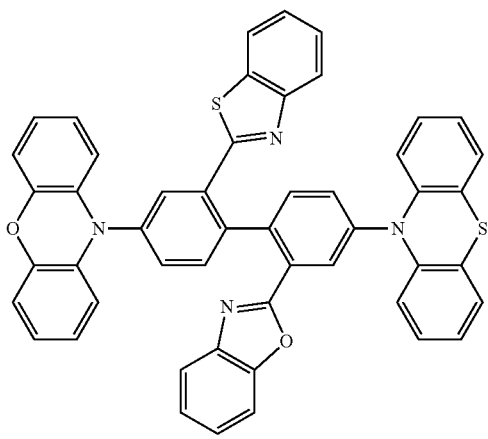
145
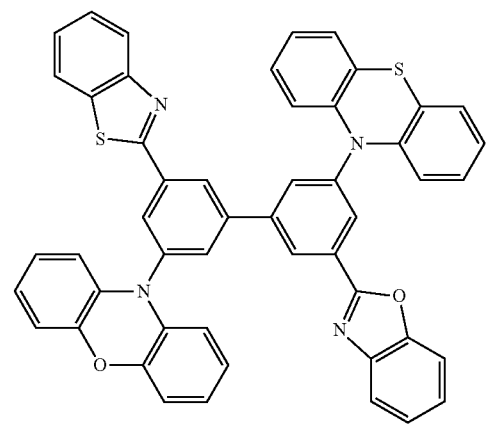
148
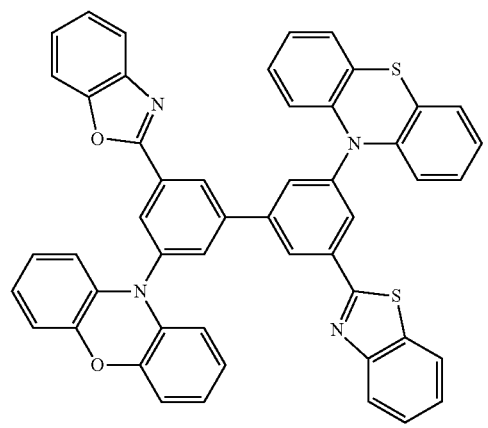
146
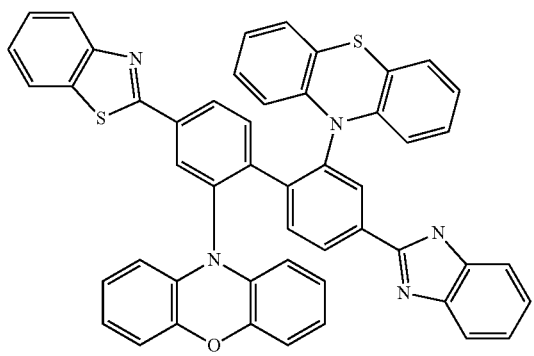
149
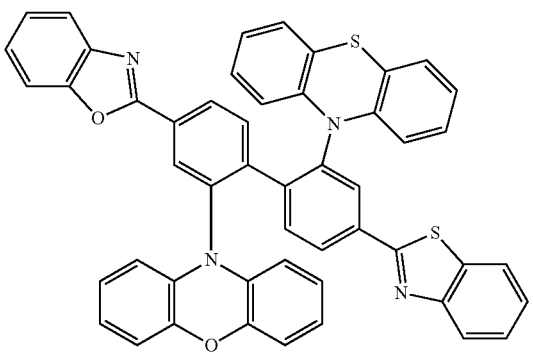

150
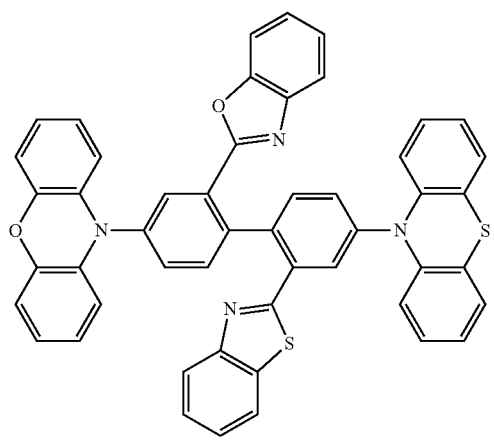
151
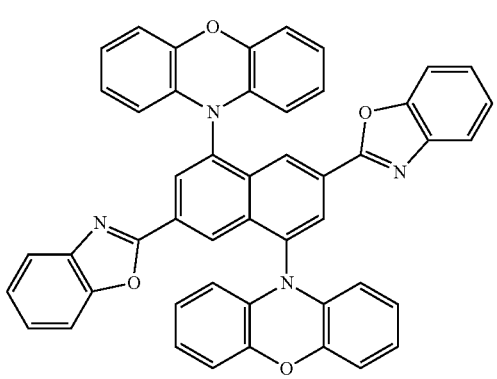
152
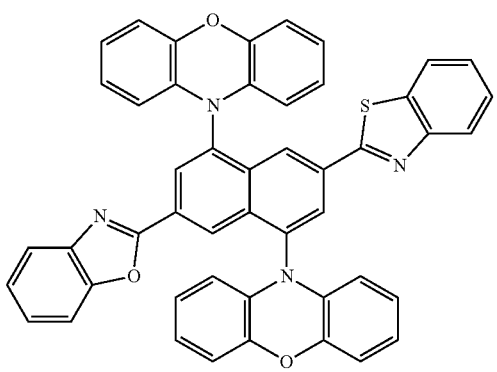
153
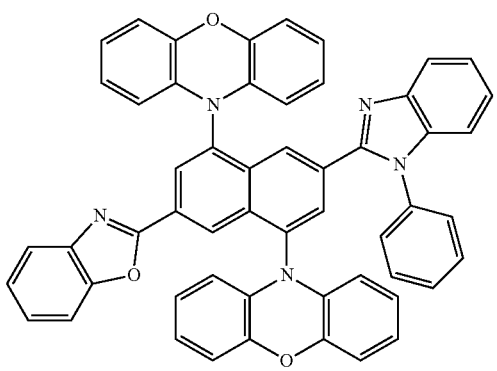
154
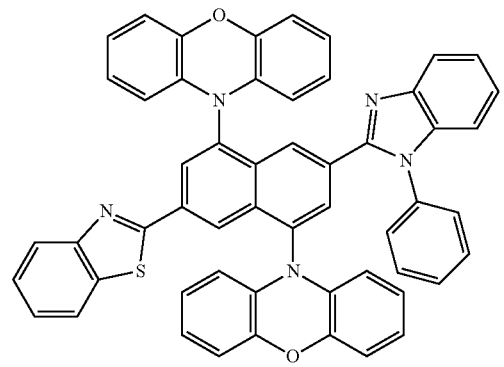
155
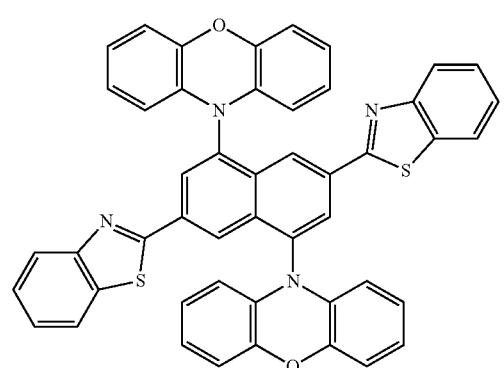
156
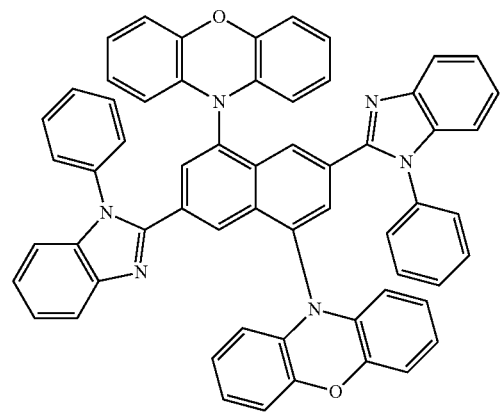
157
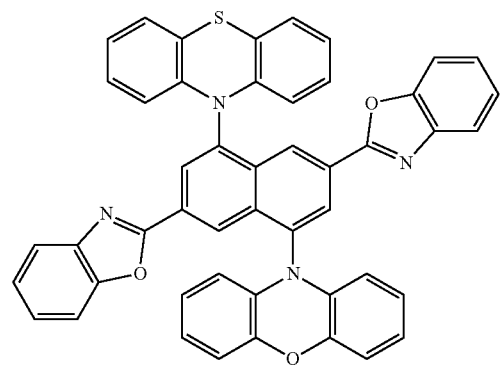

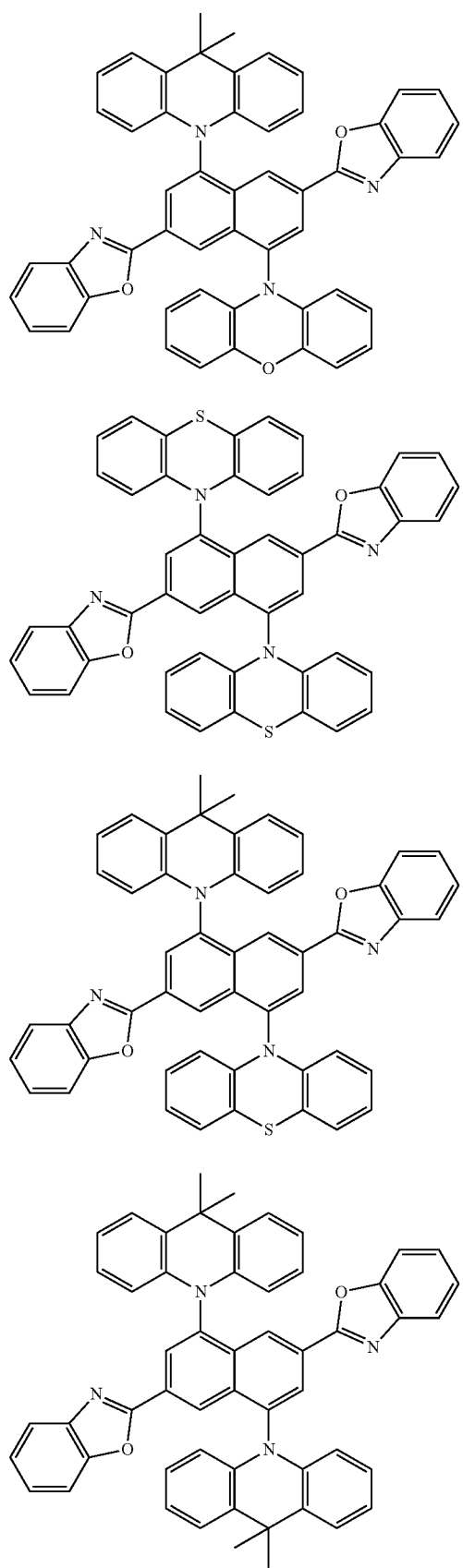
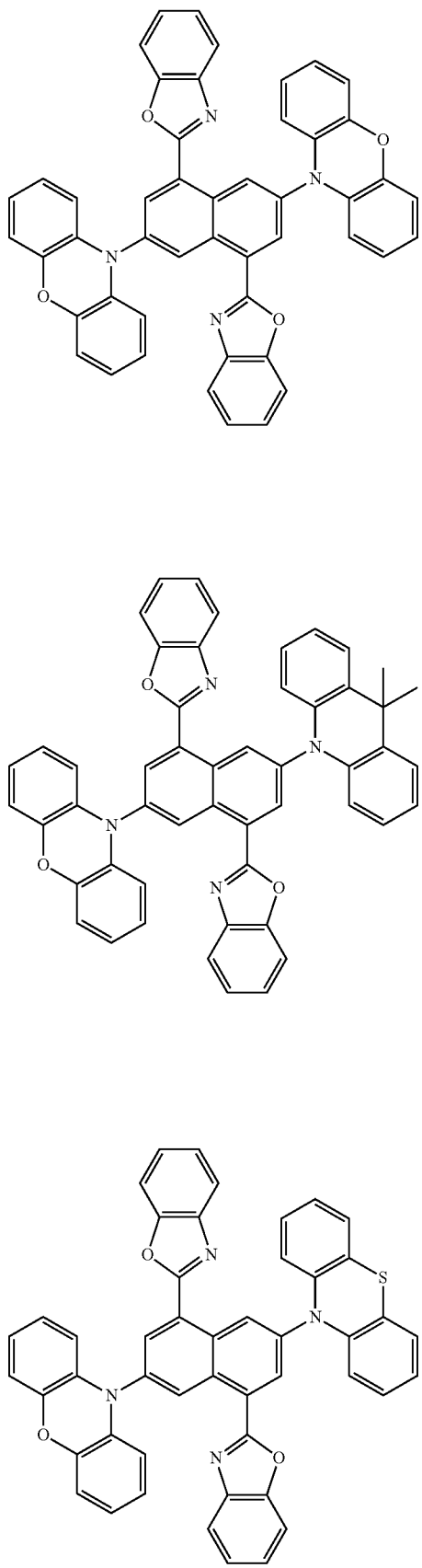

165
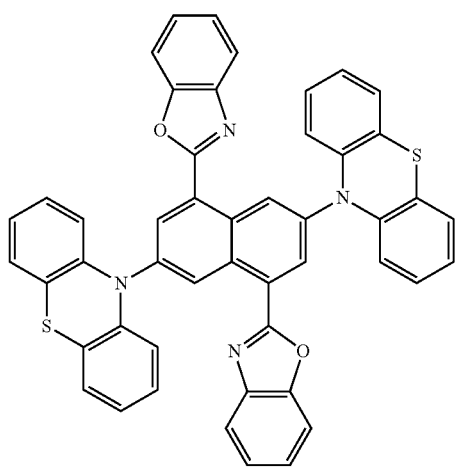
166
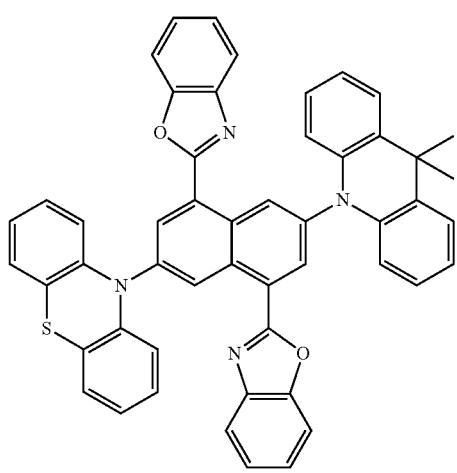
167
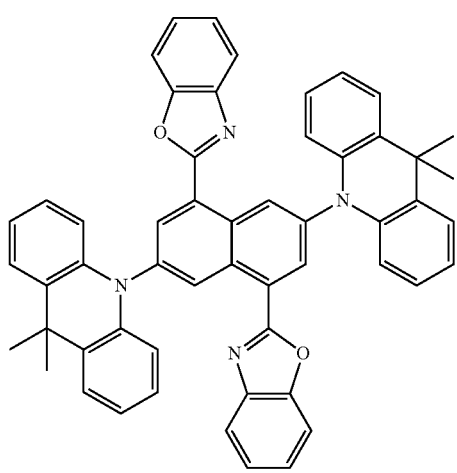
168
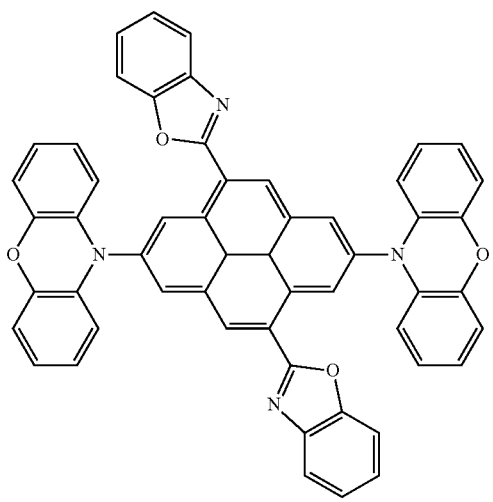
169
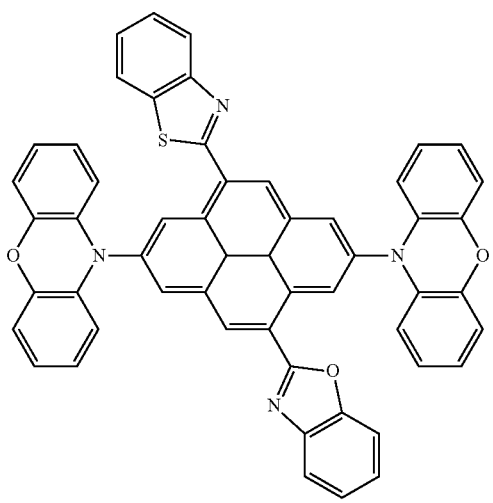
170
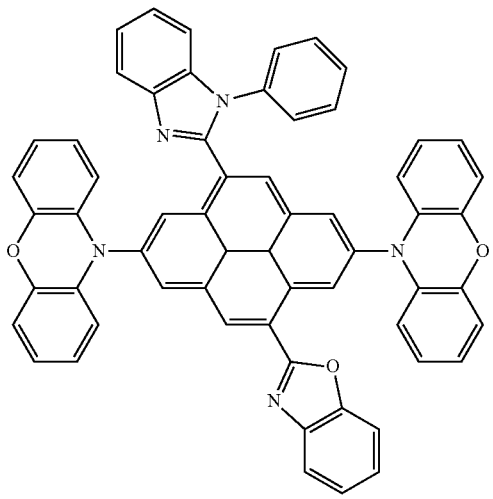

-continued

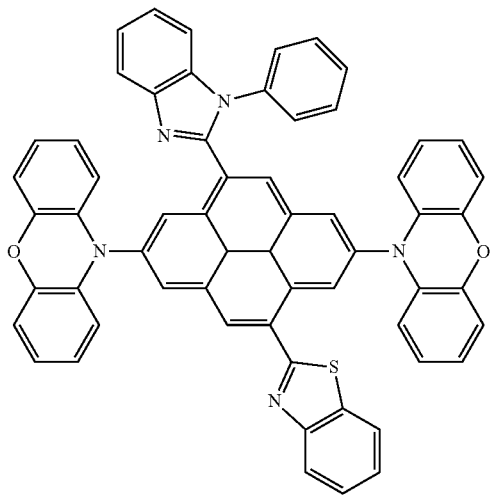

171

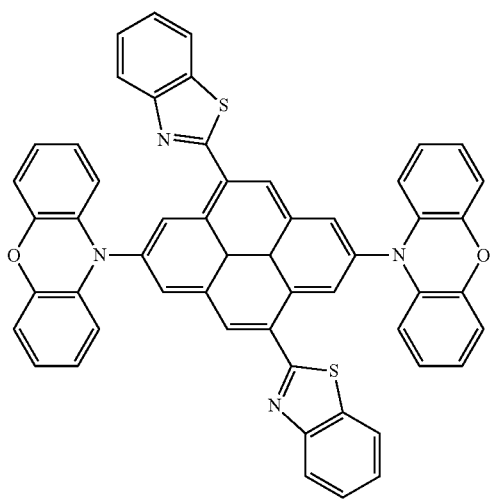

172

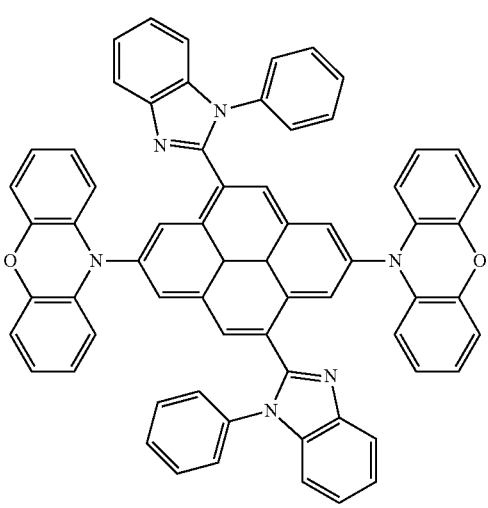

173 and

-continued

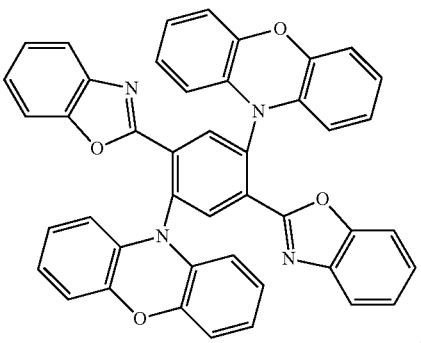

174

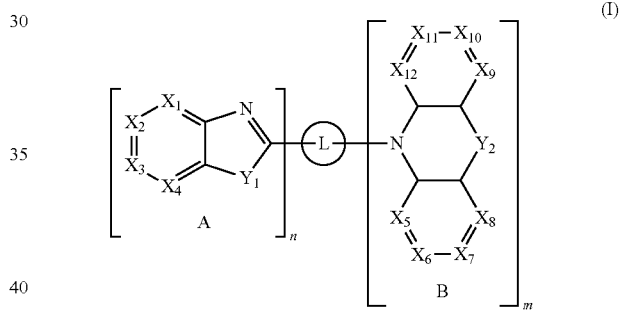

15. A process for manufacturing an organic optoelectronic device, comprising providing an anode, a cathode and one or more organic layers located between the anode and the cathode, wherein at least one layer of the organic layers comprises a compound of claim 1.

16. An organic optoelectronic device, comprising an anode, a cathode and one or more organic layers located between the anode and the cathode, wherein at least one layer of the organic layers comprises a compound of Formula (I):

$$\left[\begin{array}{c} X_2 \!\!\stackrel{X_1}{\underset{X_3}{\Vert}}\!\! \stackrel{N}{\underset{X_4}{\Vert}} \\ A \end{array}\right]_n \!\!-\!\!(L)\!\!-\!\! N \left[\begin{array}{c} X_{11}\!\!-\!\!X_{10} \\ X_{12} \phantom{xx} X_9 \\ \phantom{xx} \phantom{xx} Y_2 \\ X_5 \phantom{xx} X_8 \\ X_6\!\!-\!\!X_7 \\ B \end{array}\right]_m \quad (I)$$

wherein
$X_1$ to $X_{12}$ are each independently $CR_1$ or N;
$Y_1$ is O, S or $NR_2$;
$Y_2$ is O, S, $CR_3R_4$, $NR_5$ or $SiR_6R_7$;
$R_1$ to $R_7$ are each independently hydrogen, deuterium, $C_{1-30}$ alkyl, $C_{6-30}$ aryl or $C_{2-20}$ heteroaryl;
L is a linking moiety which enables the structure of Formula (I) to form a conjugated system;
when n is 1, 2 or 3, m is 2 or 3; when n is 2 or 3, m is 1, 2 or 3;
if n is greater than 1, each Moiety A in Formula (I) is the same as each other or different from each other; and
if m is greater than 1, each Moiety B in Formula (I) is the same as each other or different from each other.

17. The organic optoelectronic device according to claim 16, wherein at least one layer of the organic layers is a luminescent layer and the luminescent layer comprises the compound of the compound of Formula (I).

18. The organic optoelectronic device according to claim 16, wherein the organic layer further comprises a hole transport layer, a hole injection layer, an electron blocking layer, a hole blocking layer, an electron transport layer, an electron injection layer, or a combination thereof.

19. The organic optoelectronic device according to claim 17, wherein the organic layer further comprises a hole transport layer, a hole injection layer, an electron blocking layer, a hole blocking layer, an electron transport layer, an electron injection layer, or a combination thereof.

20. The organic optoelectronic device according to claim 17, wherein the compound of Formula (I) is present in the luminescent layer as a doped material, a co-doped material or a host material.

* * * * *